(12) United States Patent
Klaus et al.

(10) Patent No.: US 11,642,346 B2
(45) Date of Patent: May 9, 2023

(54) COMBINATION THERAPY FOR TREATING CANCER

(71) Applicant: Epizyme, Inc., Cambridge, MA (US)

(72) Inventors: Christine Klaus, Waban, MA (US); Maria Alejandra Raimondi, Jamaica Plain, MA (US)

(73) Assignee: Epizyme, Inc., Cambridge, MA (US)

( * ) Notice: Subject to any disclaimer, the term of this patent is extended or adjusted under 35 U.S.C. 154(b) by 150 days.

(21) Appl. No.: 16/499,476

(22) PCT Filed: Mar. 30, 2018

(86) PCT No.: PCT/US2018/025455
§ 371 (c)(1),
(2) Date: Sep. 30, 2019

(87) PCT Pub. No.: WO2018/183885
PCT Pub. Date: Oct. 4, 2018

(65) Prior Publication Data
US 2021/0100810 A1 Apr. 8, 2021

Related U.S. Application Data

(60) Provisional application No. 62/480,248, filed on Mar. 31, 2017.

(51) Int. Cl.
| | | |
|---|---|---|
| *A61K 31/5377* | (2006.01) | |
| *A61K 31/282* | (2006.01) | |
| *A61K 31/4184* | (2006.01) | |
| *A61K 31/436* | (2006.01) | |
| *A61K 31/4406* | (2006.01) | |
| *A61K 31/4745* | (2006.01) | |
| *A61K 31/475* | (2006.01) | |
| *A61K 31/506* | (2006.01) | |
| *A61K 31/519* | (2006.01) | |
| *A61K 31/55* | (2006.01) | |
| *A61K 31/704* | (2006.01) | |
| *A61K 31/7048* | (2006.01) | |
| *A61K 31/7068* | (2006.01) | |
| *A61K 31/445* | (2006.01) | |
| *A61K 31/496* | (2006.01) | |
| *A61K 31/4412* | (2006.01) | |
| *A61K 38/15* | (2006.01) | |
| *A61N 5/10* | (2006.01) | |
| *A61P 35/00* | (2006.01) | |

(52) U.S. Cl.
CPC ........ *A61K 31/5377* (2013.01); *A61K 31/282* (2013.01); *A61K 31/4184* (2013.01); *A61K 31/436* (2013.01); *A61K 31/4406* (2013.01); *A61K 31/475* (2013.01); *A61K 31/4745* (2013.01); *A61K 31/506* (2013.01); *A61K 31/519* (2013.01); *A61K 31/55* (2013.01); *A61K 31/704* (2013.01); *A61K 31/7048* (2013.01); *A61K 31/7068* (2013.01); *A61K 38/15* (2013.01); *A61N 5/10* (2013.01); *A61P 35/00* (2018.01)

(58) Field of Classification Search
CPC .............. A61K 31/5377; A61K 31/282; A61K 31/4184; A61K 31/436; A61K 31/4406; A61K 31/4745; A61K 31/475; A61K 31/506; A61K 31/519; A61K 38/15; A61N 5/10; A61P 35/00
USPC ...................................................... 514/19.9
See application file for complete search history.

(56) References Cited

U.S. PATENT DOCUMENTS

| | | | |
|---|---|---|---|
| 4,522,811 A | 6/1985 | Eppstein et al. | |
| 8,536,179 B2 | 9/2013 | Miller et al. | |
| 8,765,732 B2* | 7/2014 | Kuntz | A61K 31/4412 514/210.18 |
| 9,889,138 B2* | 2/2018 | Keilhack | A61P 35/00 |
| 10,369,155 B2* | 8/2019 | Keilhack | A61P 35/00 |
| 10,456,407 B2* | 10/2019 | Keilhack | A61K 31/506 |
| 10,463,671 B2* | 11/2019 | Keilhack | A61K 31/4965 |
| 10,946,024 B2* | 3/2021 | Keilhack | A61K 31/453 |
| 11,026,949 B2* | 6/2021 | Keilhack | A61P 35/00 |
| 2012/0264734 A1 | 10/2012 | Kuntz et al. | |
| 2015/0141362 A1* | 5/2015 | Copeland | A61P 43/00 514/45 |
| 2015/0368229 A1 | 12/2015 | Albrecht et al. | |
| 2016/0346293 A1 | 12/2016 | Keilhack | |

FOREIGN PATENT DOCUMENTS

| | | |
|---|---|---|
| WO | WO 2011/140324 A1 | 11/2011 |
| WO | WO 2012/034132 A2 | 3/2012 |
| WO | WO 2012/118812 A2 | 9/2012 |
| WO | WO 2012/142504 A1 | 10/2012 |
| WO | WO 2012/142513 A1 | 10/2012 |

(Continued)

OTHER PUBLICATIONS

Muscat et al. (Clin Cancer Res, Jul. 15, 2016, 22(14): 3560-70).*
Knipstein et al. (Neuro-Oncology 14(2):175-183, 2012).*
Entinostat—MeSH—NCBI (Mar. 28, 2022, p. 1).*
Alimova, I. et al. (2013) "Inhibition of EZH2 Suppresses Self-Renewal and Induces Radiation Sensitivity in Atypical Rhabdoid Teratoid Tumor Cells" *Neuro-Oncology*, 15(2):149-160.

(Continued)

*Primary Examiner* — Yan Xiao
(74) *Attorney, Agent, or Firm* — Cooley LLP; Heidi A. Erlacher; Christine E Dunne

(57) ABSTRACT

The present disclosure relates to methods of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by using an EZH2 inhibitor in combination with one or more additional treatment modalities.

8 Claims, 15 Drawing Sheets

(56) References Cited

FOREIGN PATENT DOCUMENTS

| WO | WO 2013/120104 A2 | 8/2013 |
|---|---|---|
| WO | WO 2013/138361 A1 | 9/2013 |
| WO | WO 2013/155317 A1 | 10/2013 |
| WO | WO 2013/155464 A1 | 10/2013 |
| WO | WO 2014/062720 A2 | 4/2014 |
| WO | WO 2014/062732 A1 | 4/2014 |
| WO | WO 2014/062733 A2 | 4/2014 |
| WO | WO 2014/100646 A1 | 6/2014 |
| WO | WO 2014/100665 A1 | 6/2014 |
| WO | WO 2014/124418 A1 | 8/2014 |
| WO | WO 2014/144747 A1 | 9/2014 |
| WO | WO 2014/172044 A1 | 10/2014 |
| WO | WO 2015/010049 A1 | 1/2015 |
| WO | WO 2015/010078 A2 | 1/2015 |
| WO | WO 2015/057859 A1 | 4/2015 |
| WO | WO 2015/058125 A1 | 4/2015 |
| WO | WO 2015/085325 A1 | 6/2015 |
| WO | WO 2015/195848 A1 | 12/2015 |
| WO | WO 2015/200650 A9 | 12/2015 |
| WO | WO 2016/061507 A1 | 4/2016 |
| WO | WO 2016/081523 A1 | 5/2016 |
| WO | WO 2016/172199 A1 | 10/2016 |
| WO | WO 2016/201328 A1 | 12/2016 |
| WO | WO 2017/035234 A1 | 3/2017 |
| WO | WO 2017/053930 A2 | 3/2017 |
| WO | WO 2017/062495 A2 | 4/2017 |
| WO | WO 2017/079757 A1 | 5/2017 |
| WO | WO 2017/100362 A2 | 6/2017 |
| WO | WO 2017/13 9404 A1 | 8/2017 |
| WO | WO 2017/132518 A1 | 8/2017 |
| WO | WO 2017/210395 A1 | 12/2017 |
| WO | WO 2017/218953 A1 | 12/2017 |
| WO | WO 2018/102687 A2 | 6/2018 |
| WO | WO 2018/144798 A1 | 8/2018 |

OTHER PUBLICATIONS

Cahn, R.S. (1964) "An Introduction to the Sequence Rule: A system for the specification of absolute configuration," *J Chem Educ*, 41(3):116-125.

Cahn, R.S. et al. (1951) "Specification of Configmation about Quadricovalent Asymmeric Atoms," *J Chem Soc*, pp. 612-622.

Cahn, R.S. et al. (1956) "The Specification of Asymmetric Configuration in Organic Chemistry," *Experientia*, vol. 12, pp. 81-94.

Cahn, R.S. et al. (1966) "Specification of Molecular Chirality," *Angew. Chem. Inter. Edit.*, 5(4):385-415, with Errata, p. 511.

Eisenhauer, E. A. et al. (Jan. 2009) "New response evaluation criteria in solid tumors: Revised RECIST guideline (version 1.1)" *Eur J Cancer*, 45:228-247.

Garapaty-Rao, S. et al. (Nov. 2013) "Identification of EZH2 and EZHI Small Molecule Inhibitors with Selective Impact on Diffuse Large B Cell Lymphoma Cell Growth" *Chem Biol*, 20:1329-1339.

Kleer, C.G. et al. (Sep. 30, 2003) "EZH2 is a marker of aggressive breast cancer and promotes neoplastic transformation of breast epithelial cells" *Proc Natl Acad Sci USA*, 100(20):11606-11611.

Knutson, S.K. et al. (2012) "A Selective Inhibitor of EZH2 Blocks H3K27 Methylation and Kills Mutant Lymphoma Cells" *Nat Chem Biol*, 8:890-896.

Knutson, S.K. et al. (2013) "Durable tumor regression in genetically altered malignant rhabdoid tumors by inhibition of methyltransferase EZH2" *Proc Natl Acad Sci USA*, 110(19):7922-7927.

Li, Y. et al. (Mar. 4, 2003) "Selective killing of cancer cells by β-lapachone: Direct checkpoint activation as a strategy against cancer" *PNAS*, 100(5):2674-2678.

Patani, G.A et al., "Bioisosterism: A Rational Approach in Drug Design," *Chem. Rev.* (1996), vol. 96, No. 8, pp. 3147-3176.

Prokopuk, L. et al. (2018) "Pharmacological inhibition of EZH2 disrupts the female germline epigenome" *Clin Epigenetics*, 10:33, https://doi.org/10.1186/s13148-018-0465-4; 12 pages.

Qi, W. et al. (Dec. 2012) "Selective inhibition of EZH2 by a small molecule inhibitor blocks tumor cells proliferation" *Proc Natl Acad Sci USA*, 109(52):21360-21365.

Richardson, E. A. et al. (May 1, 2018) "Atypical Teratoid Rhabdoid Tumour: From Tumours to Therapies" *J Korean Neurosurg Soc*, 61(3):302-311.

Varambally, S. et al. (Oct. 2002) "The Polycomb Group Protein EZH2 Is Involved in Progression of Prostate Cancer" *Nature*, 419:624-629.

Wilson, B.G. et al. (Oct. 2010) "Epigenetic Antagonism between Polycomb and SWI/SNF Complexes during Oncogenic Transformation" *Cancer Cell*, 18(4):316-328.

\* cited by examiner

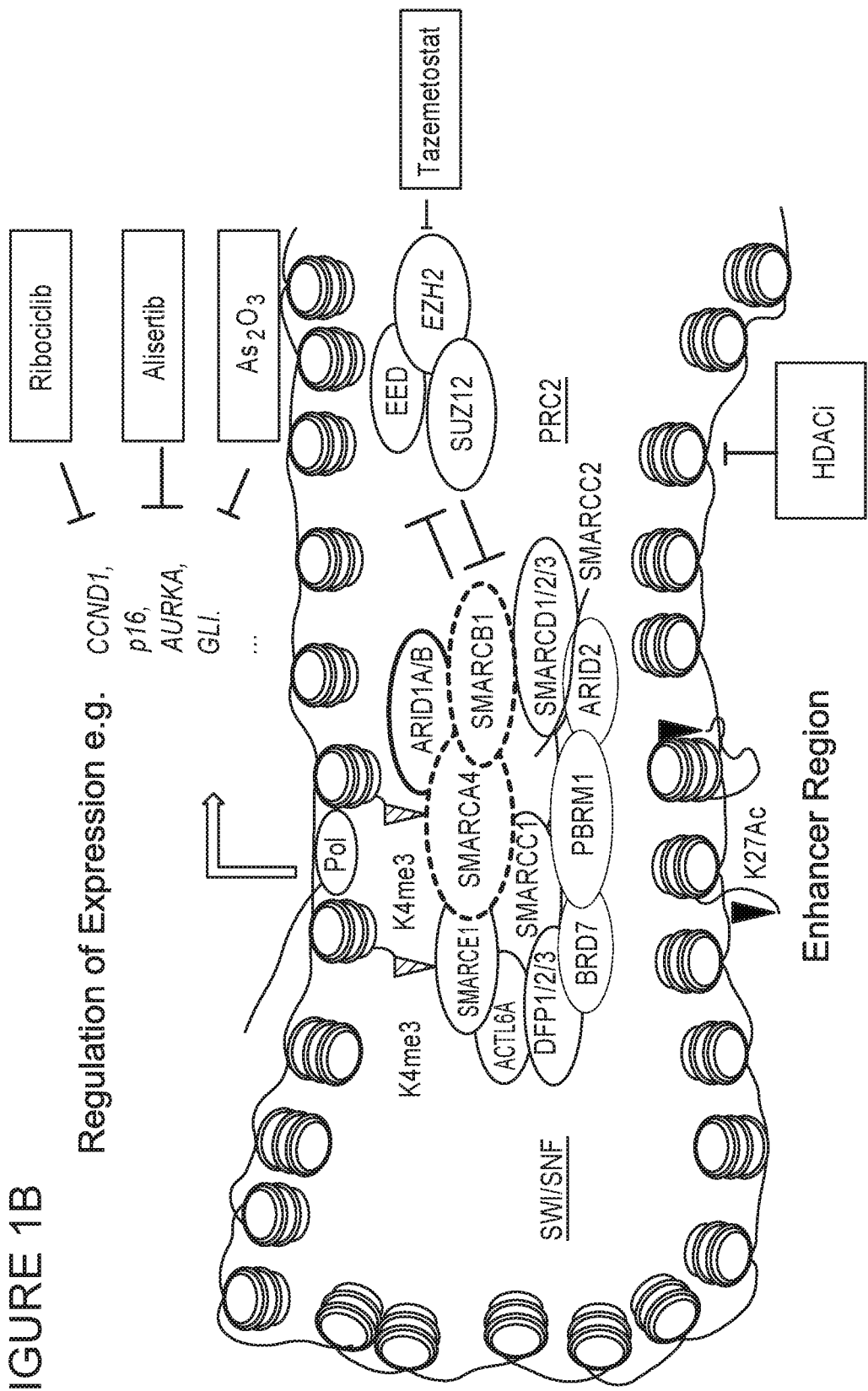

Positive Control: INI1

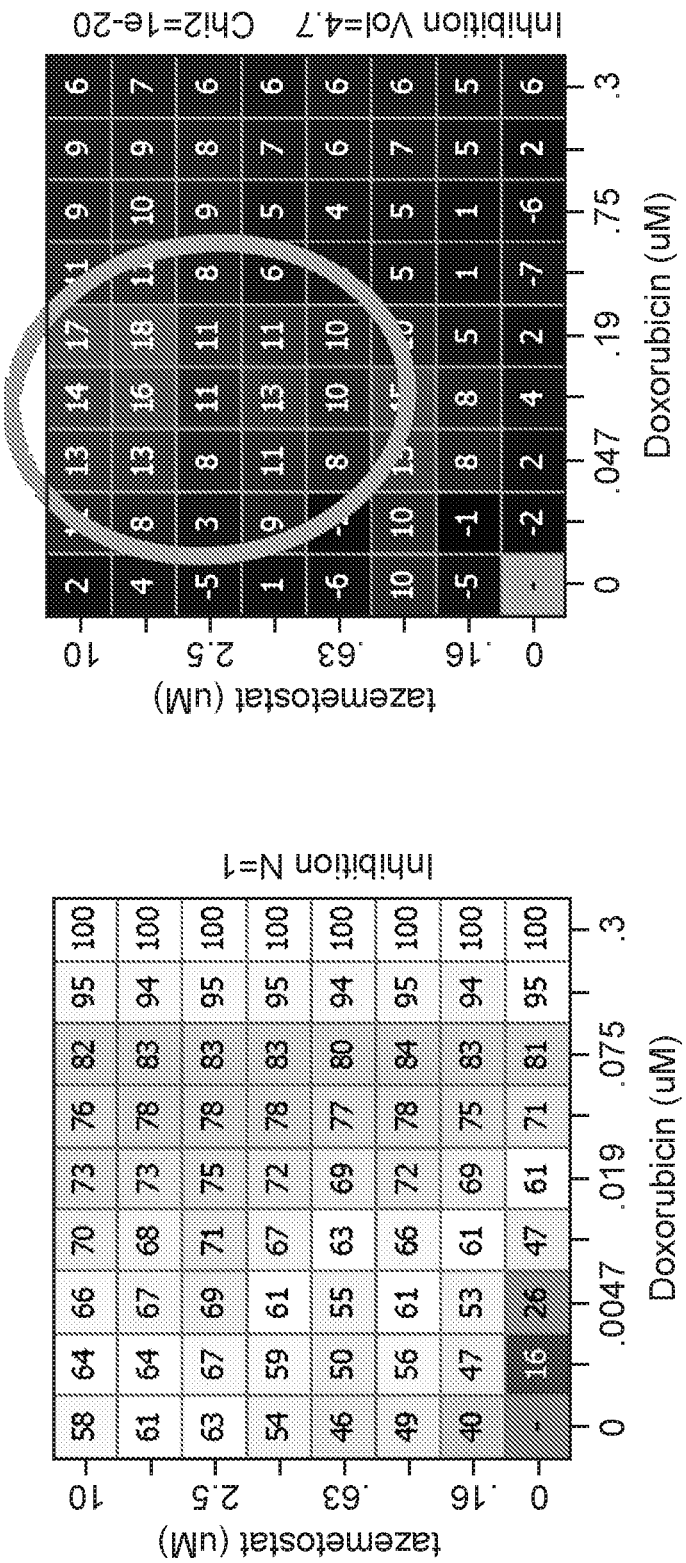

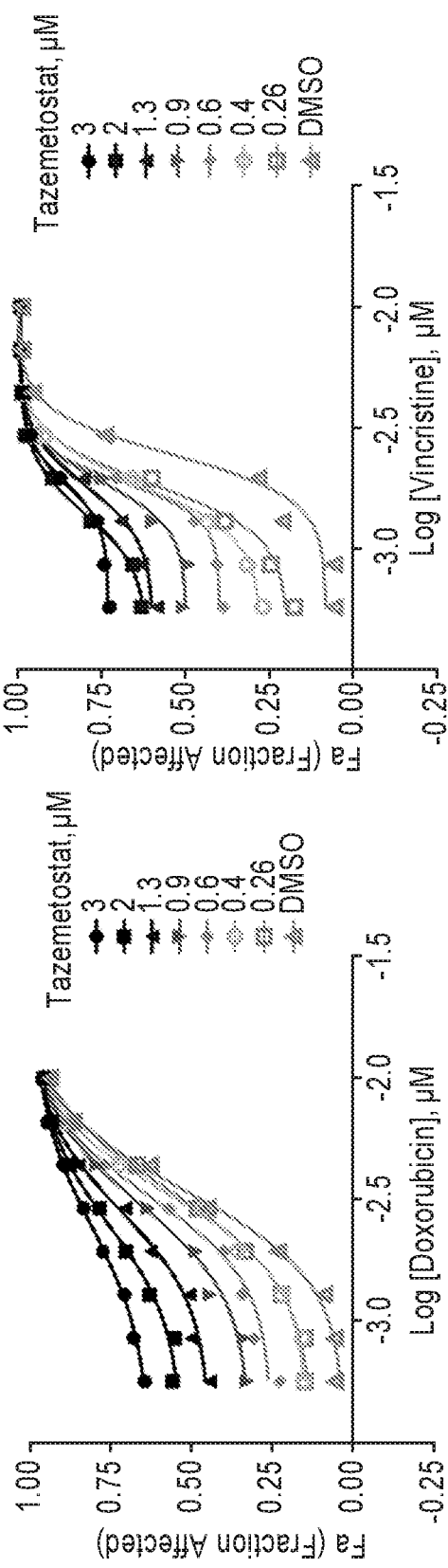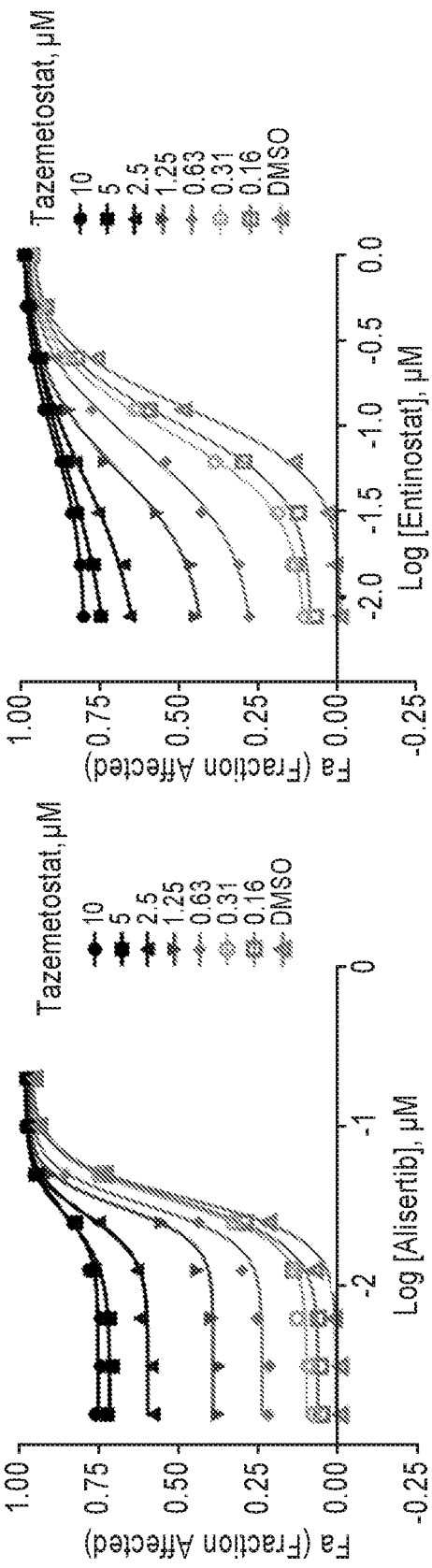

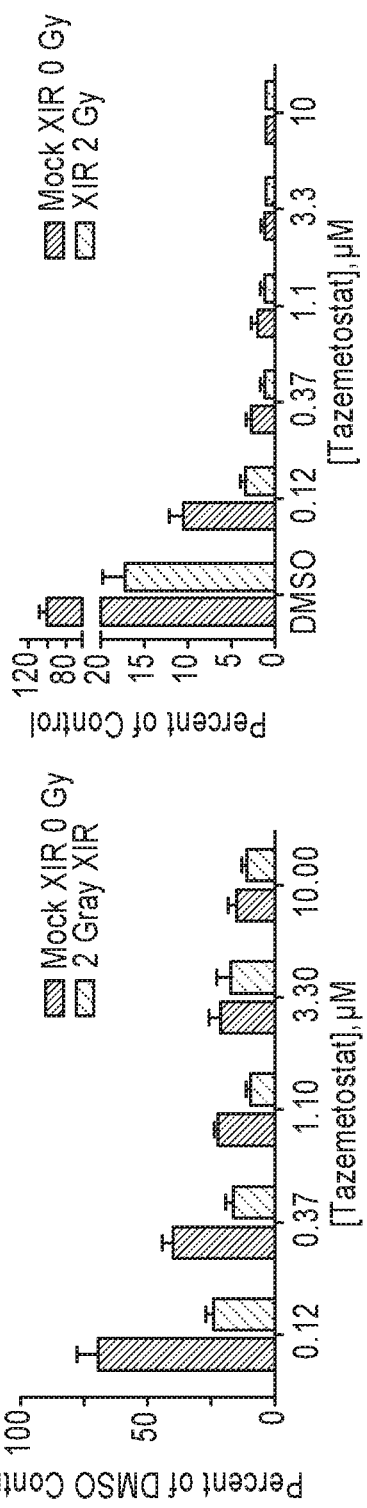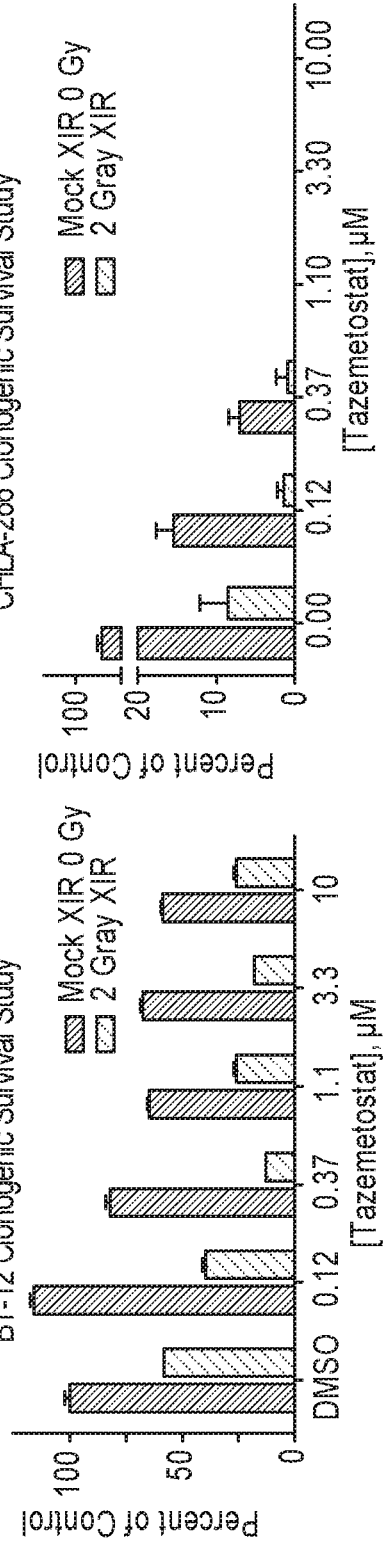
FIGURE 12A FIGURE 12B FIGURE 12C FIGURE 12D

COMBINATION THERAPY FOR TREATING CANCER

RELATED APPLICATIONS

This application is a U.S. National Phase application, filed under 35 U.S.C. § 371, of International Application No. PCT/US2018/025455, filed Mar. 30, 2018, which claims priority to, and the benefit of, U.S. Provisional Application No. 62/480,248, filed Mar. 31, 2017, the contents of each of which are incorporated herein by reference in their entireties.

SUMMARY OF THE DISCLOSURE

Some aspects of the present disclosure relate to strategies, methods, compositions, compounds, uses, medicaments, products, kits and combinations for treating certain cancers, e.g., malignant rhabdoid tumors (MRT), rhabdoid tumors of the kidney (RTK), atypical teratoid/rhabdoid tumors (AT/RT), epithelioid malignant peripheral nerve sheath tumors, myoepithelial carcinomas, and/or renal medullary carcinomas with a combination of an EZH2 inhibitor and a second treatment modality, e.g., a standard-of care treatment, such as, e.g., radiation therapy and/or one or more chemotherapeutic drug. In some embodiments, the cancer treated with the strategies, methods, compositions, and combinations provided herein is an INI1-negative cancer.

Some aspects of the present disclosure provide methods, compounds, medicaments, products, or kits for treatment or prevention of a certain cancers, e.g., of malignant rhabdoid tumors (MRT), rhabdoid tumors of the kidney (RTK), atypical teratoid/rhabdoid tumors (AT/RT), epithelioid malignant peripheral nerve sheath tumors, myoepithelial carcinomas, and/or renal medullary carcinomas. In some embodiments, the method comprises administering to a subject in need thereof (a) a first agent in a therapeutically effective amount, wherein the first agent comprises an EZH2 inhibitor, and (b) one or more additional treatment modalities in a therapeutically effective amount. In some embodiments, the method includes one or more of the following features. In some embodiments, the malignant rhabdoid tumor (MRT) is an INI1-negative tumor. In some embodiments, the rhabdoid tumor of the kidney (RTK) is an INI1-negative tumor. In some embodiments, the atypical teratoid/rhabdoid tumor (ATRT) is an INI1-negative tumor. In some embodiments, the epithelioid malignant peripheral nerve sheath tumor is an INI1-negative tumor. In some embodiments, the myoepithelial carcinoma is an INI1-negative tumor. In some embodiments, the EZH2 inhibitor is administered orally. In some embodiments, the subject is a human being. In some embodiments, the subject is younger than 18 years.

In certain embodiments of the disclosure, the EZH2 inhibitor is a compound of Formula (VIa) below.

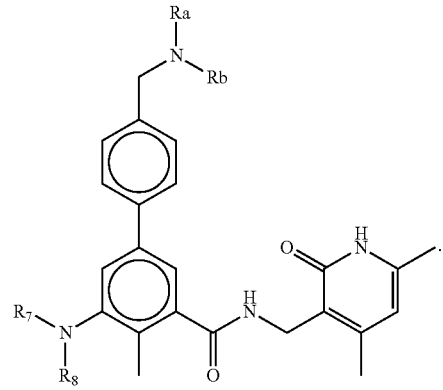

In some embodiments, compounds of Formula (VIa) can include one or more of the following features:

In some embodiments, each of $R_a$ and $R_b$, independently is H or $C_1$-$C_6$ alkyl.

In some embodiments, $R_a$ and $R_b$, together with the N atom to which they are attached, is a 4 to 7-membered heterocycloalkyl ring having 0 or 1 additional heteroatom, the $C_1$-$C_6$ alkyl and the 4 to 12-membered (e.g., 4 to 7-membered) heterocycloalkyl ring being optionally substituted with one or more -$Q_3$-$T_3$.

In some embodiments, $Q_3$ is a bond or unsubstituted or substituted $C_1$-$C_3$ alkyl linker.

In some embodiments, $T_3$ is H, halo, 4 to 7-membered heterocycloalkyl, $C_1$-$C_3$ alkyl, $OR_d$, $COOR_d$, —$S(O)_2R_d$, or —$NR_dR_e$, each of $R_d$ and $R_e$ independently being H or $C_1$-$C_6$ alkyl.

In some embodiments, $R_7$ is $C_1$-$C_6$ alkyl, $C_3$-$C_8$ cycloalkyl or 4 to 12-membered (e.g., 4 to 7-membered) heterocycloalkyl, each optionally substituted with one or more -$Q_5$-$T_5$. For example, $R_7$ is not H.

In some embodiments, $R_7$ is 4 to 7-membered heterocycloalkyl optionally substituted with one or more -$Q_5$-$T_5$.

In some embodiments, $R_7$ is piperidinyl, tetrahydropyran, cyclopentyl, or cyclohexyl, each optionally substituted with one -$Q_5$-$T_5$.

In some embodiments, $T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 12-membered (e.g., 4 to 7-membered) heterocycloalkyl.

In some embodiments, $Q_5$ is a bond and $T_5$ is $C_1$-$C_6$ alkyl, $C_3$-$C_8$ cycloalkyl, or 4 to 12-membered (e.g., 4 to 7-membered) heterocycloalkyl.

In some embodiments, $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 12-membered (e.g., 4 to 7-membered) heterocycloalkyl.

In some embodiments, $Q_5$ is $C_1$-$C_3$ alkyl linker and $T_5$ is H or $C_6$-$C_{10}$ aryl.

In some embodiments, $Q_5$ is $C_1$-$C_3$ alkyl linker and $T_5$ is $C_3$-$C_8$ cycloalkyl, 4 to 7-membered heterocycloalkyl, or $S(O)_qR_q$.

In some embodiments, $R_7$ is cyclopentyl or cyclohexyl, each optionally substituted with one -$Q_5$-$T_5$.

In some embodiments, $Q_5$ is NHC(O) and $T_5$ is $C_1$-$C_6$ alkyl or $C_1$-$C_6$ alkoxy.

In some embodiments, $R_7$ is isopropyl.

In some embodiments, each of $R_2$ and $R_4$, independently is H or $C_1$-$C_6$ alkyl optionally substituted with amino, mono-$C_1$-$C_6$ alkylamino, di-$C_1$-$C_6$ alkylamino, or $C_6$-$C_{10}$ aryl.

In some embodiments, $R_8$ is H, methyl, or ethyl.

In some embodiments, $R_8$ is methyl.

In some embodiments, $R_8$ is ethyl.

In some embodiments, $R_8$ is 4 to 7-heterocycloalkyl, e.g., tetrahydropyran.

In certain embodiments of the disclosure, the compound of Formula (VIa) is tazemetostat (also referred to herein as compound (A), and also known as Compound 44, EPZ-6438, and E7438) having the following formula:

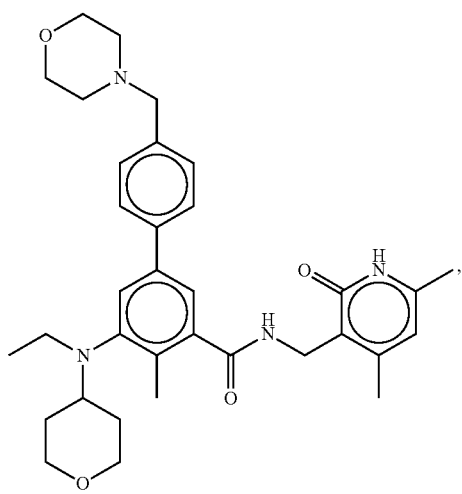

(A)

or a pharmaceutically acceptable salt thereof.

As used herein, the expressions "Compound (A)," "tazemetostat," "EPZ-6438," and "EPZ-6438" all refer to the same Compound (A) and can be used interchangeably.

In some embodiments, the EZH2 inhibitor is administered to the subject at a dose of about 100 mg to about 3200 mg daily.

In some embodiments, the EZH2 inhibitor is administered to the subject at a dose of about 100 mg BID to about 1600 mg BID.

In some embodiments, the EZH2 inhibitor is administered to the subject at a dose of about 100 mg BID, 200 mg BID, 400 mg BID, 800 mg BID, or about 1600 mg BID.

In some embodiments, the EZH2 inhibitor is administered to the subject at a dose of 800 mg BID.

In some embodiments, the EZH2 inhibitor is selected from the group consisting of:

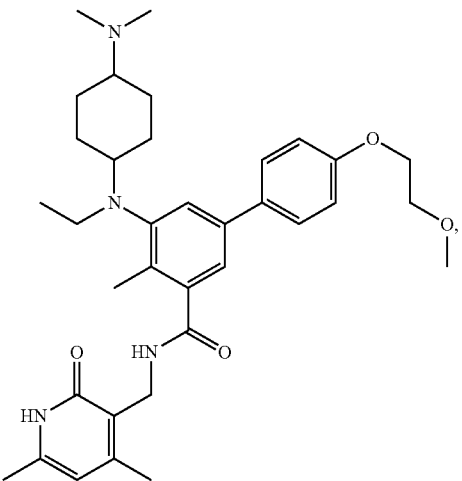

(B)

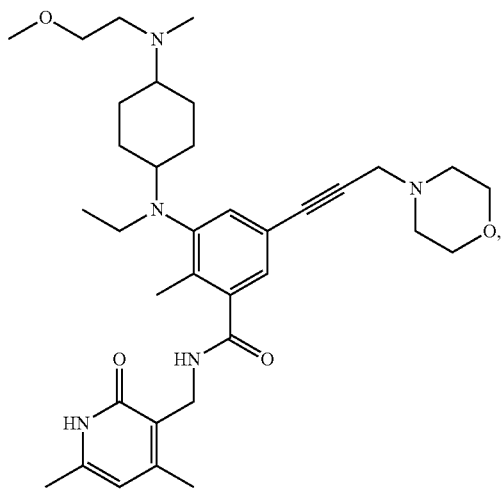

(C)

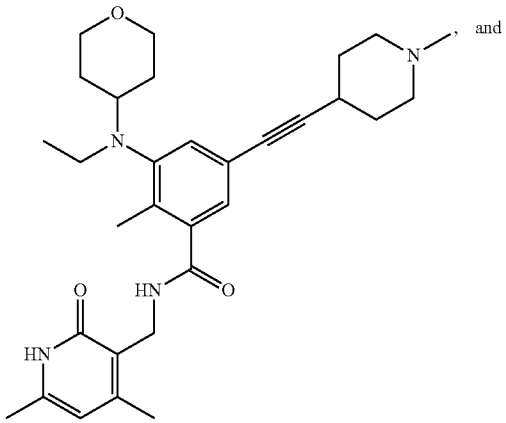

(D)

and

-continued (E)

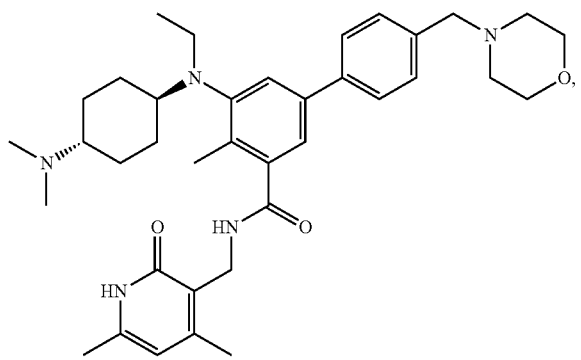

and pharmaceutically acceptable salts thereof.

In some embodiments, the EZH2 inhibitor is:

(B)

or a pharmaceutically acceptable salt thereof.

In certain embodiments, the additional treatment modalities comprises a radiation therapy, e.g., an X-ray radiation. In some embodiments the additional treatment modalities comprises one or more second agents.

In certain embodiments the first agent and/or the second agent are included in a pharmaceutical composition comprising a pharmaceutically acceptable carrier. The pharmaceutically acceptable carrier may be the same for the first and second agents or may be distinct between the first and second agents.

In some embodiments, the one or more second agents comprise two or more second agents (e.g., two, three, four, or five, or more, different second agents).

Typically, the second agent(s) comprise therapeutic agents, such as chemotherapeutic agents, immunooncology agents, and standard of care agents or combinations of such agents.

Some embodiments of the methods, uses, medicaments, products, or kits provided herein include treating a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma with an EZH2 inhibitor, e.g., with tazemetostat or a pharmaceutically acceptable salt thereof, and with one or more second agents (e.g., one, two, three, four, or five different second agents). Some embodiments of the methods, uses, medicaments, products, or kits provided herein include treating a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma with an EZH2 inhibitor, e.g., with tazemetostat or a pharmaceutically acceptable salt thereof, and with two or more second agents (e.g., two, three, four, or five different second agents). Some embodiments of the methods, uses, medicaments, products, or kits provided herein include treating a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma with an EZH2 inhibitor, e.g., with tazemetostat or a pharmaceutically acceptable salt thereof, in combination with an X-ray irradiation. Some embodiments of the methods, uses, medicaments, products, or kits provided herein include treating a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma with an EZH2 inhibitor, e.g., with tazemetostat or a pharmaceutically acceptable salt thereof, in combination with an X-ray irradiation and one or more second therapeutic agents, e.g., one or more standard-of-care agent, such as, e.g., one or more chemotherapeutic drugs.

In certain embodiments of the disclosure, e.g., those in which the cancer is malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, the one or more second agents may comprise a general chemotherapeutic agent. Exemplary second agents that are a general chemotherapeutic agent include, but are not limited to, doxorubicin.

In certain embodiments of the disclosure, e.g., those in which the cancer is malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, the one or more second agents may comprise an anti-metabolite. Exemplary second agents that are an anti-metabolite include, but are not limited to, cytarabine.

In certain embodiments of the disclosure, e.g., those in which the cancer is malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, the one or more second agents may comprise a microtubule targeting drug. Exemplary second agents that are a microtubule targeting drug include, but are not limited to, paclitaxel, docetaxel, and vincristine.

In certain embodiments of the disclosure, e.g., those, in which the cancer is malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, the one or more second agents may comprise a serine/threonine kinase inhibitor. Exemplary second agents that are a serine/threonine kinase inhibitor include, but are not limited to, everolimus.

In certain embodiments of the disclosure, e.g., those in which the cancer is malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, the one or more second agents may comprise an aurora A kinase inhibitor. Exemplary second agents that are an aurora A kinase inhibitor include, but are not limited to, alisertib.

In certain embodiments of the disclosure, e.g., those in which the cancer is malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, the one or more second agents may comprise a topoisomerase inhibitor. Exemplary second agents that are a topoisomerase inhibitor include, but are not limited to, topotecan and etoposide.

In certain embodiments of the disclosure, e.g., those in which the cancer is malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, the one or more second agents may comprise DNA binding or crosslinking agent. Exemplary second agents that are a DNA binding or crosslinking agent include, but are not limited to carboplatin.

In certain embodiments of the disclosure, e.g., those in which the cancer is malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, the one or more second agents may comprise an HDAC inhibitor. Exemplary second agents that are an HDAC inhibitor include, but are not limited to, entinostat, panobinostat, and romidepsin.

In certain embodiments of the disclosure, e.g., those in which the cancer is malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, the one or more second agents may comprise a CDK inhibitor. Exemplary second agents that are a CDK inhibitor include, but are not limited to palbociclib and abemaciclib.

In certain embodiments of the disclosure, e.g., those in which the cancer is malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, the one or more second agents may comprise a MEK inhibitor. Exemplary second agents that are a MEK inhibitor include, but are not limited to, selumetinib and trametinib.

In some embodiments, the second agent of the disclosure is administered at a dosage of 0.01 mg/kg per day to about 1000 mg/kg per day.

In some embodiments, the therapeutically effective amount of the EZH2 inhibitor and the additional treatment modalities are administered simultaneously. Alternatively, the therapeutically effective amount of the EZH2 inhibitor and the one or more additional treatment modalities are administered sequentially. In certain embodiments, the EZH2 inhibitor is administered prior to the one or more additional treatment modalities. In certain embodiments, the one or more additional treatment modalities are administered prior to the EZH2 inhibitor.

In some embodiments, the therapeutically effective amount of the EZH2 inhibitor, e.g., tazemetostat or a pharmaceutically acceptable salt thereof, and the one or more additional treatment modalities are administered simultaneously. Alternatively, the therapeutically effective amount of the EZH2 inhibitor, e.g., tazemetostat or a pharmaceutically acceptable salt thereof, and the one or more second one or more additional treatment modalities are administered sequentially. In certain embodiments, the EZH2 inhibitor, e.g., tazemetostat or a pharmaceutically acceptable salt thereof, are administered prior to the one or more additional treatment modalities. In certain embodiments, the one or more additional treatment modalities are administered prior to the EZH2 inhibitor, e.g., tazemetostat or a pharmaceutically acceptable salt thereof.

In some embodiments, the therapeutically effective amount of the EZH2 inhibitor, e.g., tazemetostat or a pharmaceutically acceptable salt thereof, and the second agent are administered simultaneously. Alternatively, the therapeutically effective amount of the EZH2 inhibitor, e.g., tazemetostat or a pharmaceutically acceptable salt thereof, and the one or more second agents are administered sequentially. In certain embodiments, the EZH2 inhibitor, e.g., tazemetostat or a pharmaceutically acceptable salt thereof, are administered prior to the one or more second agents. In certain embodiments, the EZH2 inhibitor, e.g., tazemetostat or a pharmaceutically acceptable salt thereof, are administered prior to a co-treatment with the one or more second agents and the EZH2 inhibitor. In certain embodiments, the one or more second agents are administered prior to the EZH2 inhibitor, e.g., tazemetostat or a pharmaceutically acceptable salt thereof.

In some embodiments, the therapeutically effective amount of the EZH2 inhibitor, e.g., tazemetostat or a pharmaceutically acceptable salt thereof, and the radiation therapy are administered simultaneously. Alternatively, the therapeutically effective amount of the EZH2 inhibitor, e.g., tazemetostat or a pharmaceutically acceptable salt thereof, and the radiation therapy are administered sequentially. In certain embodiments, the EZH2 inhibitor, e.g., tazemetostat or a pharmaceutically acceptable salt thereof, are administered prior to the radiation therapy. In certain embodiments, the radiation therapy are administered prior to the EZH2 inhibitor, e.g., tazemetostat or a pharmaceutically acceptable salt thereof.

In certain embodiments of the disclosure, the radiation therapy comprises exposing the subject to X-ray irradiation.

Therapeutic agents of the disclosure (including a first and/or one or more second agents) are administered by any appropriate route including, but not limited to, enteral routes, and parenteral routes, e.g., oral routes, intravenous routes, intramuscular routes, and direct absorption through mucous membrane tissues. The therapeutic agents can be administered by the same route or by different routes.

The methods of combination therapy featured in the disclosure may result in a synergistic effect, wherein the effect of a combination of therapeutic agents (e.g. an EZH2 inhibitor, e.g. tazemetostat or a pharmaceutically acceptable salt thereof, and one or more second anti-cancer agents, or and EZH2 inhibitor (e.g., tazemetostat or a pharmaceutically acceptable salt thereof) and radiation therapy) is greater than the sum of the effects resulting from administration of any of the therapeutic agents as single agents. A synergistic effect may also be an effect that cannot be achieved by administration of any of the therapeutic agents as single agents. The synergistic effect may include, but is not limited to, an effect of treating cancer, e.g., multiple myeloma or mantle cell lymphoma, by reducing tumor size, reducing the number or frequency of malignant cells in a subject or a sample obtained from a subject, inhibiting tumor growth, inhibiting growth, survival, or proliferation of malignant cells, or increasing survival of the subject. The synergistic effect may also include reducing cancer cell viability, inducing cancer cell death, and inhibiting or delaying cancer cell growth.

In some embodiments, a subject of a method provided by the disclosure has cancer, including, but not limited to, an INI1-negative tumor. In some embodiments, a subject of a method provided by the disclosure has a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

The subject may be of any species; however, subjects are preferably human. In some embodiments, the subject may have cancer characterized by any stage, including, but not limited to, stage 0, I, II, III, and IV. In some embodiments, the subject's cancer is a primary or secondary tumor. The subject's cancer may be metastatic. The subject's cancer may have metastasized to a secondary location from another primary location. In some embodiments, the subject's a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma may migrate, or may have migrated, from one region of the body to another. For example, a malignant rhabdoid tumor may start out in the kidney and later migrate into the brain and/or other soft tissues.

In some embodiments, a subject provided herein, e.g., a subject having an INI-1 negative tumor, or a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, may express a wild type EZH2.

In some embodiments, a subject provided herein, e.g., a subject having an INI-1 negative tumor, or a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, may express a mutant EZH2. For example, a mutant EZH2 comprises one or more mutations, wherein the mutation is a substitution, a point mutation, a nonsense mutation, a missense mutation, a deletion, or an insertion. A mutant EZH2 of the disclosure may comprise a mutation in the substrate pocket domain. A mutant EZH2 may have a substitution at amino acid Y641. In some embodiments, the mutant EZH2 has one of the following mutations: substitution of phenylalanine (F) for the wild type residue tyrosine (Y) at amino acid position 641 (Y641F); a substitution of histidine (H) for the wild type residue tyrosine (Y) at amino acid position 641 (Y641H); a substitution of asparagine (N) for the wild type residue tyrosine (Y) at amino acid position 641 (Y641N); a substitution of serine (S) for the wild type residue tyrosine (Y) at amino acid position 641 (Y641S); and a substitution of cysteine (C) for the wild type residue tyrosine (Y) at amino acid position 641 (Y641C).

In some embodiments, of the EZH2 mutation may include, but is not limited to: a substitution of glycine (G) for the wild type residue alanine (A) at amino acid position 677 (A677G); a substitution of valine (V) for the wild type residue alanine (A) at amino acid position 687 (A687V); a substitution of methionine (M) for the wild type residue valine (V) at amino acid position 674 (V674M); a substitution of histidine (H) for the wild type residue arginine (R) at amino acid position 685 (R685H); a substitution of cysteine (C) for the wild type residue arginine (R) at amino acid position 685 (R685C); a substitution of serine (S) for the wild type residue asparagine (N) at amino acid position 322 (N322S), a substitution of glutamine (Q) for the wild type residue arginine (R) at amino acid position 288 (R288Q), a substitution of isoleucine (I) for the wild type residue threonine (T) at amino acid position 573 ($T_{573}I$), a substitution of glutamic acid (E) for the wild type residue aspartic acid (D) at amino acid position 664 (D664E), a substitution of glutamine (Q) for the wild type residue arginine (R) at amino acid position 458 (R458Q), a substitution of lysine (K) for the wild type residue glutamic acid (E) at amino acid position 249 (E249K), a substitution of cysteine (C) for the wild type residue arginine (R) at amino acid position 684 (R684C), a substitution of histidine (H) for the wild type residue arginine (R) at amino acid position 628 (R628H), a substitution of histidine (H) for the wild type residue glutamine (Q) at amino acid position 501 (Q501H), a substitution of asparagine (N) for the wild type residue aspartic acid (D) at amino acid position 192 (D192N), a substitution of valine (V) for the wild type residue aspartic acid (D) at amino acid position 664 (D664V), a substitution of leucine (L) for the wild type residue valine (V) at amino acid position 704 (V704L), a substitution of serine (S) for the wild type residue proline (P) at amino acid position 132 (P132S), a substitution of lysine (K) for the wild type residue glutamic acid (E) at amino acid position 669 (E669K), a substitution of threonine (T) for the wild type residue alanine (A) at amino acid position 255 (A255T), a substitution of valine (V) for the wild type residue glutamic acid (E) at amino acid position 726 (E726V), a substitution of tyrosine (Y) for the wild type residue cysteine (C) at amino acid position 571 (C571Y), a substitution of cysteine (C) for the wild type residue phenylalanine (F) at amino acid position 145 (F145C), a substitution of threonine (T) for the wild type residue asparagine (N) at amino acid position 693 (N693T), a substitution of serine (S) for the wild type residue phenylalanine (F) at amino acid position 145 (F145S), a substitution of histidine (H) for the wild type residue glutamine (Q) at amino acid position 109 (Q109H), a substitution of cysteine (C) for the wild type residue phenylalanine (F) at amino acid position 622 (F622C), a substitution of arginine (R) for the wild type residue glycine (G) at amino acid position 135 (G135R), a substitution of glutamine (Q) for the wild type residue arginine (R) at amino acid position 168 (R168Q), a substitution of arginine (R) for the wild type residue glycine (G) at amino acid position 159 (G159R), a substitution of cysteine (C) for the wild type residue arginine (R) at amino acid position 310 (R310C), a substitution of histidine (H) for the wild type residue arginine (R) at amino acid position 561 (R561H), a substitution of histidine (H) for the wild type residue arginine (R) at amino acid position 634 ($R_{634}H$), a substitution of arginine (R) for the wild type residue glycine (G) at amino acid position 660 (G660R), a substitution of cysteine (C) for the wild type residue tyrosine (Y) at amino acid position 181 (Y181C), a substitution of arginine (R) for the wild type residue histidine (H) at amino acid position 297 (H297R), a substitution of serine (S) for the wild type residue cysteine (C) at amino acid position 612 (C612S), a substitution of tyrosine (Y) for the wild type residue histidine (H) at amino acid position 694 (H694Y), a substitution of alanine (A) for the wild type residue aspartic acid (D) at amino acid position 664 (D664A), a substitution of threonine (T) for the wild type residue isoleucine (I) at amino acid position 150 (I150T), a substitution of arginine (R) for the wild type residue isoleucine (I) at amino acid position 264 (I264R), a substitution of leucine (L) for the wild type residue proline (P) at amino acid position 636 (P636L), a substitution of threonine (T) for the wild type residue isoleucine (I) at amino acid position 713 (I713T), a substitution of proline (P) for the wild type residue glutamine (Q) at amino acid position 501 (Q501P), a substitution of glutamine (Q) for the wild type residue lysine (K) at amino acid position 243 (K243Q), a substitution of aspartic acid (D) for the wild type residue glutamic acid (E) at amino acid position 130 (E130D), a substitution of glycine (G) for the wild type residue arginine (R) at amino acid position 509 (R509G), a substitution of histidine (H) for the wild type residue arginine (R) at amino acid position 566 (R566H), a substitution of histidine (H) for the wild type residue aspartic acid (D) at amino acid position 677 (D677H), a substitution of asparagine (N) for the wild type residue lysine (K) at amino acid position 466 (K466N), a substitution of histidine (H) for the wild type residue arginine (R) at amino acid position 78 (R78H), a substitution of methionine (M) for the wild type residue lysine (K) at amino acid position 1 (K6M), a substitution of leucine (L) for the wild type residue serine (S) at amino acid position 538 (S538L), a substitution of glutamine (Q) for the wild type residue leucine (L) at amino acid position 149 (L149Q), a substitution of valine (V) for the wild type residue leucine (L) at amino acid position 252 (L252V), a substitution of valine (V) for the wild type residue leucine (L) at amino acid position 674 (L674V), a substitution of valine (V) for the wild type residue alanine (A) at amino acid position 656 (A656V), a substitution of aspartic acid (D) for the wild type residue alanine (A) at amino acid position 731 (Y731D), a substitution of threonine (T) for the wild type residue alanine (A) at amino acid position 345 (A345T), a substitution of aspartic acid (D) for the wild type residue alanine (A) at amino acid position 244 (Y244D), a substitution of tryptophan (W) for the wild type residue cysteine (C) at amino acid position 576 (C576W), a substitution of lysine (K) for the wild type residue asparagine (N) at amino acid position 640 (N640K), a substitution of lysine (K) for the wild type residue asparagine (N) at amino acid position 675 (N675K), a substitution of tyrosine (Y) for the wild type residue aspartic acid (D) at amino acid position 579 (D579Y), a substitution of isoleucine (I) for the wild type residue asparagine (N) at amino acid position 693 (N693I), and/or a substitution of lysine (K) for the wild type residue asparagine (N) at amino acid position 693 (N693K).

Other mutations of EZH2 can include: a frameshift at amino acid position 730, 391, 461, 441, 235, 254, 564, 662, 715, 405, 685, 64, 73, 656, 718, 374, 592, 505, 730, or 363 or the corresponding nucleotide position of the nucleic acid sequence; a deletion of glutamic acid (E) and leucine (L) at amino acid positions 148 and 149 or a nonsense mutation at amino acid position 733, 25, 317, 62, 553, 328, 58, 207, 123, 63, 137, or 60.

In certain embodiments, the therapeutically effective amount of the EZH2 inhibitor is an amount sufficient to sensitize the subject to a treatment by administration of the one or more additional treatment modalities, e.g., simultaneously with, subsequent to, or prior to the administration of the EZH2 inhibitor. In certain embodiments, the therapeutically effective amount of the EZH2 inhibitor is an amount sufficient to sensitize the subject to a subsequent treatment by administration of the one or more additional treatment modalities. In certain embodiments, the amount of the one or more additional treatment modalities that is therapeutically effective is smaller than the amount of the same treatment modalities that is therapeutically effective in a subject not administered with the EZH2 inhibitor. In certain embodiments, the amount of the one or more additional treatment modalities that is therapeutically effective is smaller than the amount of the same treatment modalities that is therapeutically effective in a subject not sensitized with the EZH2 inhibitor, e.g., simultaneously with, subsequent to, or prior to the administration of the one or more additional treatment modalities.

In other aspects, the disclosure features methods of treating a malignant rhabdoid tumor (MRT), rhabdoid tumor of the kidney (RTK), atypical teratoid/rhabdoid tumor (AT/RT), epithelioid malignant peripheral nerve sheath tumor, myoepithelial carcinoma, and/or renal medullary carcinoma by administering to a subject in need thereof an EZH2 inhibitor in an amount sufficient to sensitize the subject to a treatment with one or more additional treatment modalities.

In yet other aspects, the disclosure features methods of inhibiting or decreasing growth, viability, survival, or proliferation of a cancer cell comprising (1) contacting the cell with (a) an effective amount of EZH2 inhibitor, and (b) one or more second agents, or (2) contacting the cell with an effective amount of EZH2 inhibitor and exposing the cell to a radiation, wherein the cancer cell is an atypical teratoid rhabdoid tumor cell or a malignant rhabdoid tumor cell.

Any of the above aspects and embodiments can be combined with any other aspect or embodiment.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the disclosure, some exemplary, non-limiting suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

BRIEF DESCRIPTION OF DRAWINGS

The patent or application file contains at least one drawing executed in color. Copies of this patent or patent application publication with color drawing(s) will be provided by the Office upon request and payment of the necessary fee.

The above and further features will be more clearly appreciated from the following detailed description when taken in conjunction with the accompanying drawings.

FIGS. 1A and 1B illustrate the suggested functions of PRC2-EZH2 and an antagonistic interaction between PRC2 and SWI/SNF. FIG. 1A is a schematic showing antagonism of polycomb target expression by SWI/SNF and PRC2, demonstrating how perturbations in SWI/SNF activity may lead to oncogenesis via imbalanced PRC2 activity. FIG. 1B is a schematic representation of the epigenetic roles of SMARCB1 (INI1) in promoter activation, occupancy and enhancer modification. The SWI/SNF complex modulates gene expression by antagonism of the PRC2 complex. Chromatin antagonizing effects of EZH2 may be therapeutically targeted by tazemetostat.

FIG. 2A illustrates the pretreatment model; FIG. 2B illustrates the co-treatment model.

(FIG. 3A) CHLA-266 cells derived at diagnosis from 30 month old female with atypical rhabdoid tumor (AT/RT) who had not received prior therapy, from tumor located in the posterior fossa; (FIG. 3B) BT-12 cells derived at diagnosis from 2 month old Caucasian female with stage 4 AT/RT who had not received prior therapy, from primary solid tumor located in the posterior fossa; (FIG. 3C) A204 cells derived from 1 year old female with a malignant rhabdoid tumor (MRT) which was originally incorrectly designated as a rhabdomyosarcoma; (FIG. 3D) G401 cells derived from 3 month old Caucasian male with a rhabdoid tumor of the kidney; (FIG. 3E) INI1-positive tonsil stains used as positive control.

FIGS. 5A-5D are a set of graphs illustrating synergy of doxorubicin with tazemetostat in BT-12 cells grown in the pretreatment model described in Example 3. FIG. 5A is the dose matrix for the in vitro assay. FIG. 5B shows the Loewe excess matrix for the combination of doxorubicin with tazemetostat. FIG. 5C shows the isobologram for the combination of doxorubicin with tazemetostat. FIG. 5D is a combination index plot (Chou-Talalay plot, Fa-CI plot) for the combination of doxorubicin with tazemetostat.

FIG. 6A is the dose matrix for the in vitro assay. FIG. 6B shows the Loewe excess matrix for the combination of doxorubicin with tazemetostat. FIG. 6C shows the isobologram for the combination of doxorubicin with tazemetostat. FIG. 6D is a combination index plot (Chou-Talalay plot, Fa-CI plot) for the combination of doxorubicin with tazemetostat.

FIGS. 10A-10D are a series of graphs illustrating synergy of tazemetostat with additional agents in G401 cells. The graphs depict the effect (fa) as a function of concentration of (FIG. 10A) doxorubicin, (FIG. 10B) vincristine, (FIG. 10C) alisertib and (FIG. 10D) entinostat at various concentrations of tazemetostat as indicated in the graphs. The concentrations of the additional agents are represented on a logarithmic scale.

FIGS. 12A and 12B are a series of graphs demonstrating reduction in clonogenic survival of atypical rhabdoid tumor (AT/RT) cell lines by X-ray irradiation at 2 Gy, following 7-day priming with tazemetostat at concentrations between 0.12 and 10.00 μM. FIG. 12A shows the results of a proliferation study in BT-12 cells (left) and CHLA-266 cells (right). FIG. 12B shows the results of a clonogenic survival study in BT-12 cells (left) and CHLA-266 cells (right).

DETAILED DESCRIPTION OF THE DISCLOSURE

Figure 1A:
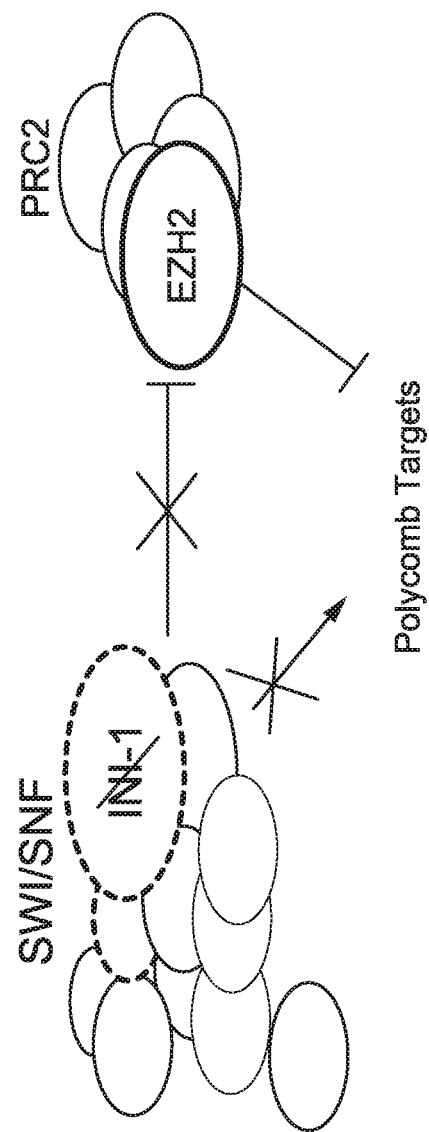
Figure 2B:
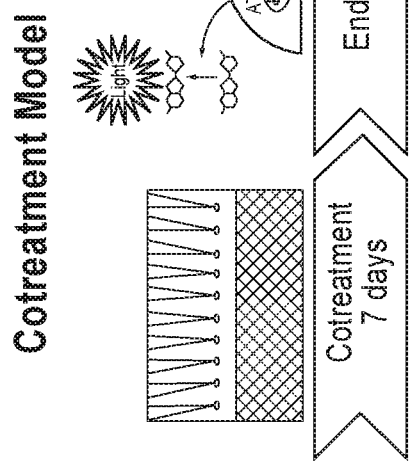
FIGS. 2A and 2B are a pair of schematic diagrams depicting the experimental procedures of Example 3.
Figure 2A:
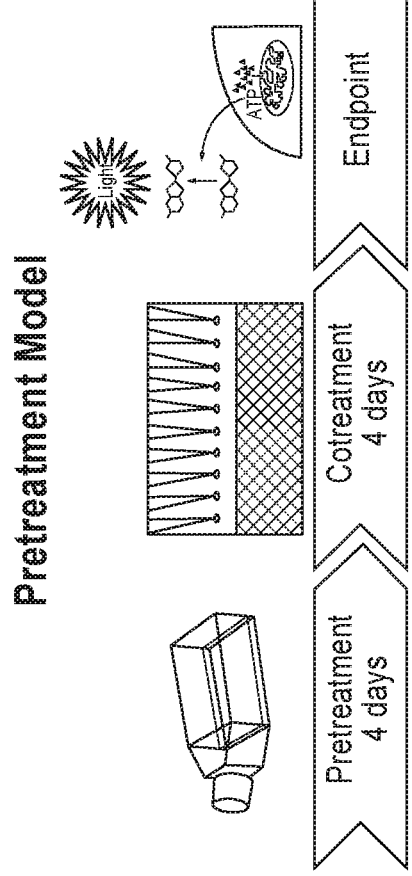
Figure 3B:
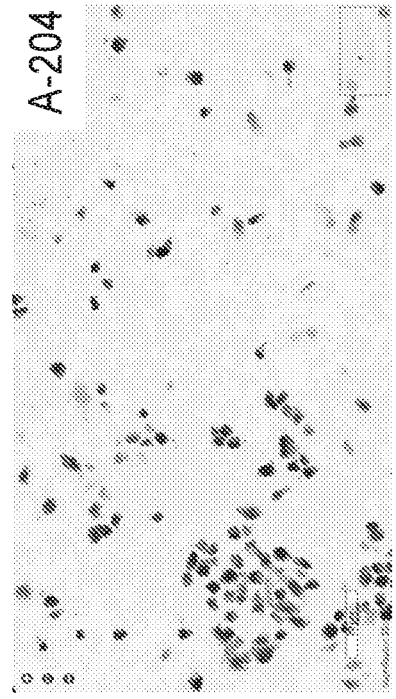
FIGS. 3A-3E are a series of H&E stains, showing absence of staining for INI-1 in rhabdoid tumor derived cell lines.
Figure 3D:
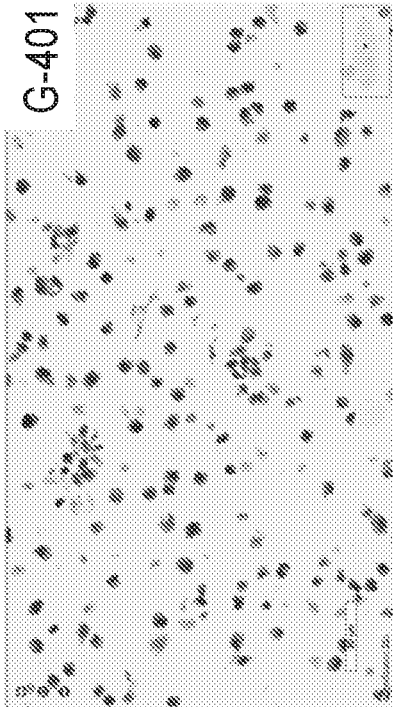
Figure 3A:
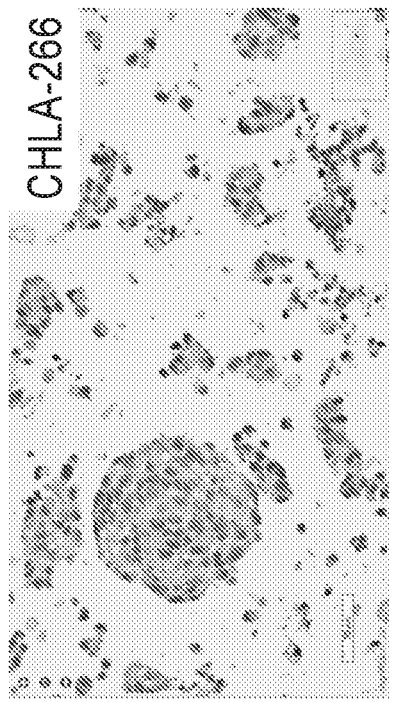
Figure 3C:
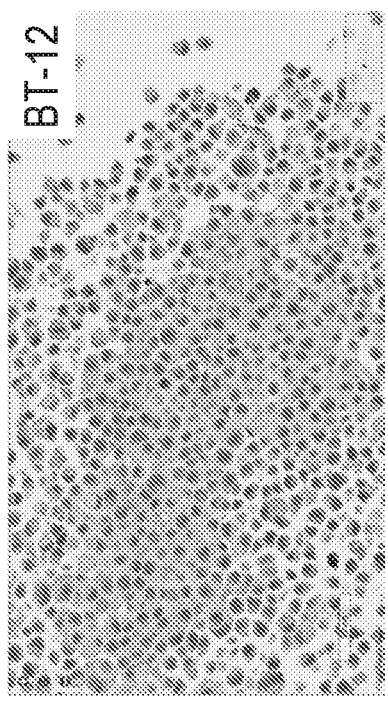
Figure 3E:
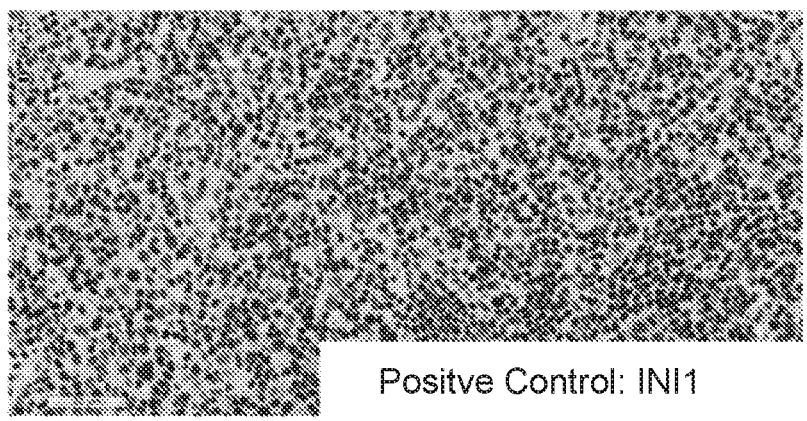

Histone methyltransferases (HMTs) play a crucial role in the regulation of gene expression. In particular, HMTs are involved in the regulation of cellular division and of cellular differentiation. HMTs mediate the methylation of histones associated with particular genes. Depending on the amino acid residues that are methylated, the methylation event can either signal a silencing event or an activation event for the associated gene. Examples of a silencing mark include the trimethylation of H3K27; whereas, trimethylation of H3K4 results in a gene activating signal. Many cell cycle check point regulators and tumor suppressor genes exist in a "bivalent" state, wherein these contain both activating histone modifications (e.g. H3K27me3) and suppressing histone modifications (e.g. H3K4me3). Genes in a bivalent state are poised to undergo either activation or suppression depending on external factors. EZH2 regulates bivalent genes involved in B-cell differentiation and maturation, including CDKN1, PRDM1, and IRF4.

EZH2 is a histone methyltransferase that is the catalytic subunit of the PRC2 complex which catalyzes the mono-through tri-methylation of lysine 27 on histone H3 (H3-K27). Histone H3-K27 trimethylation is a mechanism for suppressing transcription of specific genes that are proximal to the site of histone modification. This trimethylation is known to be a cancer marker with altered expression in cancer, such as prostate cancer (see, e.g., U.S. Patent Application Publication No. 2003/0175736; incorporated herein by reference in its entirety). Other studies provided evidence for a functional link between dysregulated EZH2 expression, transcriptional repression, and neoplastic transformation. Varambally et al. (2002) *Nature* 419(6907):624-9 Kleer et al. (2003) *Proc Natl Acad Sci USA* 100(20):11606-11.

EZH2 methylation activity plays an important role in the regulation and activation of germinal center B-cells. EZH2 protein levels increase following the activation of B-cells. Following activation, B-cells take residence in the germinal center of lymphoid organs, wherein somatic hypermutation occurs, a process associated with the repression of anti-apoptotic genes and check point regulators. EZH2 methylating events target genes that are involved in B-cell proliferation, differentiation and maturation, including CDKN1A (role in cellular proliferation), PRDM1 (role in B-cell differentiation) and IRF4 (role in B-cell differentiation).

Genetic alterations within the EZH2 gene are associated with altered histone methylation patterns. For example, certain point mutations in EZH2 are associated with altered methylation of H3K4 in DLBCL; furthermore, chromosomal translocation and fusion, SSX:SS18, is associated with altered H3K27 methylation in synovial sarcoma. EZH2 mutations leading to the conversion of amino acid Y641 (equivalent to Y646, catalytic domain), to either F, N, H, S or C results in hypertrimethylation of H3K27 and drives lymphomagenesis. Additional genetic alterations that affect the methylation of H3K27 include EZH2 SET-domain mutations, overexpression of EZH2, overexpression of other PRC2 subunits, loss of function mutations of histone acetyl transferases (HATs), and loss of function of MLL2. Cells that are heterozygous for EZH2 Y646 mutations result in hypertrimethylation of H3K27 relative to cells that are homozygous wild-type (WT) for the EZH2 protein, or to cells that are homozygous for the Y646 mutation.

EPZ-6438 (Compound (A), tazemetostat) is a small molecule inhibitor of EZH2, the catalytic subunit of the polycomb repressive complex 2 that methylates H3K27. Hypertrimethylation of H3K27 (H3K27Me3) appears tumorigenic in various malignancies, including subsets of Non-Hodgkin Lymphoma (NHL) with mutant EZH2. Inhibition of H3K27Me3 with EPZ-6438 leads to killing of EZH2 mutant lymphoma cells and other EZH2 inhibitors show activity in models of mutant and WT EZH2 NHL. In addition, tumors with loss of INI1, a subunit of the SWI-SNF chromatin remodeling complex, appeared dependent on EZH2. EPZ-6438 was shown to induce apoptosis and differentiation of INI1-deleted malignant rhabdoid tumor (MRT) models in vitro and in MRT xenograft-bearing mice.

This disclosure is based on, at least in part, discovery that Enhancer of Zeste Homolog 2 (EZH2) inhibitors may effectively treat cancer(s), for example cancer(s) that are characterized by aberrant H3-K27 methylation.

Some aspects of the present disclosure relate to a method for treating or preventing a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma. The method comprises administering to a subject in need thereof (a) a first agent in a therapeutically effective amount, wherein the first agent comprises an EZH2 inhibitor, and (b) one or more second agents in a therapeutically effective amount.

Other aspects of the present disclosure relate to a method for treating or preventing a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma. The method comprises administering to a subject in need thereof (a) a first agent in a therapeutically effective amount, wherein the first agent comprises an EZH2 inhibitor, and (b) one or more second agents in a therapeutically effective amount. In other aspects, the present disclosure relates to a method for treating a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma comprising administering to a subject in need thereof (a) a first agent in a therapeutically effective amount, wherein the first agent comprises an EZH2 inhibitor, and (b) one or more second agents in a therapeutically effective amount.

Other aspects of the present disclosure relate to a method for treating or preventing malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma. The method comprises administering to a subject in need thereof (a) a first agent in a therapeutically effective amount, wherein the first agent comprises an EZH2 inhibitor, and (b) radiation therapy in a therapeutically effective amount. In other aspects, the present disclosure relates to a method for treating malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma comprising administering to a subject in need thereof (a) a first agent in a therapeutically effective amount, wherein the first agent comprises an EZH2 inhibitor, and (b) radiation therapy in a therapeutically effective amount, wherein the malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma is selected from rhabdoid tumor of the kidney (RTK), atypical teratoid/rhabdoid tumor (ATRT), epithelioid malignant peripheral nerve sheath tumor, myoepithelial carcinoma, and renal medullary carcinoma.

Other aspects of the present disclosure relate to a method for treating or preventing malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma. The method comprises administering to a subject in need thereof (a) a first agent in a therapeutically effective amount, wherein the first agent comprises an EZH2 inhibitor, and (b) radiation therapy in a therapeutically effective amount. In other aspects, the present disclosure relates to a method for treating malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma comprising administering to a subject in need thereof (a) a first agent in a therapeutically effective amount, wherein the first agent comprises an EZH2 inhibitor, and (b) radiation therapy in a therapeutically effective amount.

Other aspects of the present disclosure relate to a first agent for use in the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with one or more additional treatment modalities, wherein the first agent comprises an EZH2 inhibitor.

Other aspects of the present disclosure relate to a first agent for use as a medicament for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with one or more additional treatment modalities, wherein the first agent comprises an EZH2 inhibitor.

Other aspects of the present disclosure relate to the use of a first agent in the manufacture of a medicament for treating a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with one or more additional treatment modalities, wherein the first agent comprises an EZH2 inhibitor.

Other aspects of the present disclosure relate to a first agent for use in combination with one or more additional treatment modalities in the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, wherein the first agent comprises an EZH2 inhibitor.

Other aspects of the present disclosure relate to the use of a first agent as a medicament for combinational therapy with one or more additional treatment modalities for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, wherein the first agent comprises an EZH2 inhibitor.

Other aspects of the present disclosure relate to the use of a first agent in a combinational therapy with one or more additional treatment modalities for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, wherein the first agent comprises an EZH2 inhibitor.

Other aspects of the present disclosure relate to a first agent for use in the manufacture of a medicament for combinational therapy with one or more additional treatment modalities for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, wherein the first agent comprises an EZH2 inhibitor.

Other aspects of the present disclosure relate to a product comprising a first agent and one or more additional treatment modalities as a combined preparation for simultaneous, separate or sequential use in the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma, wherein the first agent comprises an EZH2 inhibitor.

Other aspects of the present disclosure relate to a kit comprising (a) a pharmaceutical composition comprising a first agent, and (b) a pharmaceutical composition comprising one or more additional treatment modalities, wherein the first agent comprises an EZH2 inhibitor.

In some embodiments, the present disclosure relates to one or more therapeutic agents for use in the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with an EZH2 inhibitor.

In some embodiments, the present disclosure relates to one or more therapeutic agents for use as a medicament for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with an EZH2 inhibitor.

In some embodiments, the present disclosure relates to the use of one or more therapeutic agents in the manufacture of a medicament for treating a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with an EZH2 inhibitor.

In some embodiments, the present disclosure relates to one or more therapeutic agents for use in combination with an EZH2 inhibitor in the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the present disclosure relates to the use of one or more therapeutic agents as a medicament for combinational therapy with an EZH2 inhibitor for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the present disclosure relates to the use of one or more therapeutic agents in a combinational therapy with an EZH2 inhibitor for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the present disclosure relates to one or more therapeutic agents for use in the manufacture of a medicament for combinational therapy with an EZH2 inhibitor for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the present disclosure relates to a product comprising one or more therapeutic agents and an EZH2 inhibitor as a combined preparation for simultaneous, separate or sequential use in the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the present disclosure relates to a kit comprising (a) a pharmaceutical composition comprising one or more therapeutic agents, and (b) a pharmaceutical composition comprising an EZH2 inhibitor.

In some embodiments, the present disclosure relates to one or more therapeutic agents for use in the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with an EZH2 inhibitor and radiation therapy.

In some embodiments, the present disclosure relates to one or more therapeutic agents for use as a medicament for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with an EZH2 inhibitor and radiation therapy.

In some embodiments, the present disclosure relates to the use of one or more therapeutic agents in the manufacture of a medicament for treating a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with an EZH2 inhibitor and radiation therapy.

In some embodiments, the present disclosure relates to one or more therapeutic agents for use in combination with an EZH2 inhibitor and radiation therapy in the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the present disclosure relates to the use of one or more therapeutic agents as a medicament for combinational therapy with an EZH2 inhibitor and radiation therapy for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the present disclosure relates to the use of one or more therapeutic agents in a combinational therapy with an EZH2 inhibitor and radiation therapy for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the present disclosure relates to one or more therapeutic agents for use in the manufacture of a medicament for combinational therapy with an EZH2 inhibitor and radiation therapy for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the one or more therapeutic agents are selected from doxorubicin, cytarabine, vincristine, everolimus, alisertib, topotecan, etoposide, carboplatin, entinostat, panobinostat, romidepsin, palbociclib, abemaciclib, selumetinib, trametinib and combinations thereof.

In some embodiments, the present disclosure relates to an EZH2 inhibitor for use in the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with one or more second therapeutic agents and radiation therapy.

In some embodiments, the present disclosure relates to an EZH2 inhibitor for use as a medicament for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with one or more second therapeutic agents and radiation therapy.

In some embodiments, the present disclosure relates to the use of an EZH2 inhibitor in the manufacture of a medicament for treating a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with one or more second therapeutic agents and radiation therapy.

In some embodiments, the present disclosure relates to an EZH2 inhibitor for use in combination with one or more second therapeutic agents and radiation therapy in the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the present disclosure relates to the use of an EZH2 inhibitor as a medicament for combinational therapy with one or more second therapeutic agents and radiation therapy for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the present disclosure relates to the use of an EZH2 inhibitor in a combinational therapy with one or more second therapeutic agents and radiation therapy for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the present disclosure relates to an EZH2 inhibitor for use in the manufacture of a medicament for combinational therapy with one or more second therapeutic agents and radiation therapy for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the present disclosure relates to radiation therapy for use in the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with an EZH2 inhibitor.

In some embodiments, the present disclosure relates to radiation therapy for use as a medicament for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with an EZH2 inhibitor.

In some embodiments, the present disclosure relates to radiation therapy for use in combination with an EZH2 inhibitor in the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the present disclosure relates to the use of radiation therapy in a combinational therapy with an EZH2 inhibitor for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the present disclosure relates to radiation therapy for use in the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with an EZH2 inhibitor and one or more second therapeutic agents.

In some embodiments, the present disclosure relates to radiation therapy for use as a medicament for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma by co-administration with an EZH2 inhibitor and one or more second therapeutic agents.

In some embodiments, the present disclosure relates to radiation therapy for use in combination with an EZH2 inhibitor and one or more second therapeutic agents in the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the present disclosure relates to the use of radiation therapy in a combinational therapy with an EZH2 inhibitor and one or more second therapeutic agents for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma.

In some embodiments, the one or more second therapeutic agents are selected from doxorubicin, cytarabine, vincristine, everolimus, alisertib, topotecan, etoposide, carboplatin, entinostat, panobinostat, romidepsin, palbociclib, abemaciclib, selumetinib, trametinib and combinations thereof.

Other aspects of the present disclosure relate to a method for treating or preventing a malignant rhabdoid tumor (MRT).

Other aspects of the present disclosure relate to a method for treating or preventing a rhabdoid tumor of the kidney (RTK). In other aspects, the present disclosure relates to a method for treating or preventing an atypical teratoid/rhabdoid tumor (ATRT).

Other aspects of the present disclosure relate to a method for treating or preventing an epithelioid malignant peripheral nerve sheath tumor. In other aspects, the present disclosure relates to a method for treating or preventing a myoepithelial carcinoma. Other aspects of the present disclosure relate to a method for treating or preventing a renal medullary carcinoma.

Other aspects of the present disclosure relate to a method for treating or preventing a malignant rhabdoid tumor (MRT), wherein the malignant rhabdoid tumor is INI-1 negative.

Other aspects of the present disclosure relate to a method for treating or preventing a rhabdoid tumor of the kidney (RTK), wherein the rhabdoid tumor of the kidney is INI1-negative. In other aspects, the present disclosure relates to a method for treating or preventing an atypical teratoid/rhabdoid tumor (ATRT), wherein the atypical teratoid/rhabdoid tumor is INI-1 negative.

Other aspects of the present disclosure relate to a method for treating or preventing an epithelioid malignant peripheral nerve sheath tumor, wherein the epithelioid malignant peripheral nerve sheath tumor is INI-1 negative. In other aspects, the present disclosure relates to a method for treating or preventing a myoepithelial carcinoma, wherein the myoepithelial carcinoma is INI1-negative. Other aspects of the present disclosure relate to a method for treating or preventing a renal medullary carcinoma, wherein the renal medullary carcinoma is INI1-negative.

In some embodiments, the EZH2 inhibitor is administered orally.

In some embodiments, the subject is a human being.

In some embodiments, the subject is younger than 18 years. In certain embodiments, in any method described herein, the subject is an adult patient aged 18 years or older.

In certain embodiments, in any method described herein, the subject is a pediatric patient aged 12 months or younger (e.g., between 3 and 12 months old).

In certain embodiments, in any method described herein, the subject is a subject older than 12 months but younger than 18 years old.

In any method described herein, the subject can be a pediatric (non-adult) patient aged 3 months to 18 years.

In any of the above aspects or embodiments, the disclosure also relates to methods for detecting levels of histone methylation, e.g., H3K27 trimethylation, in a skin biopsy. Histone methylation is detected prior to initiation of treatment, while the subject is receiving treatment, and/or after treatment has concluded.

In some embodiments, an EZH2 inhibitor of the disclosure may have the following Formula I:

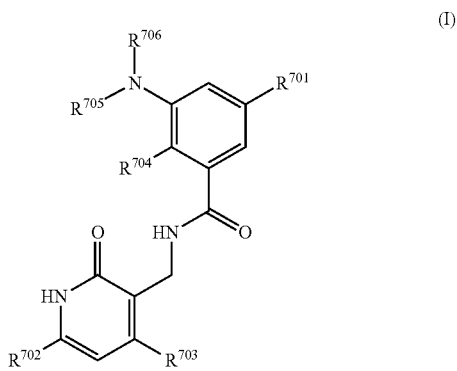

or a pharmaceutically acceptable salt thereof; wherein
$R^{701}$ is H, F, $OR^{707}$, $NHR^{707}$, —(C≡C)—$(CH_2)_{n7}$—$R^{708}$, phenyl, 5- or 6-membered heteroaryl, $C_{3-8}$ cycloalkyl, or 4-7 membered heterocycloalkyl containing 1-3 heteroatoms, wherein the phenyl, 5- or 6-membered heteroaryl, $C_{3-8}$ cycloalkyl or 4-7 membered heterocycloalkyl each independently is optionally substituted with one or more groups selected from halo, $C_{1-3}$ alkyl, OH, O—$C_{1-6}$ alkyl, NH—$C_{1-6}$ alkyl, and, $C_{1-3}$ alkyl substituted with $C_{3-8}$ cycloalkyl or 4-7 membered heterocycloalkyl containing 1-3 heteroatoms, wherein each of the O—$C_{1-6}$ alkyl and NH—$C_{1-6}$ alkyl is optionally substituted with hydroxyl, O—$C_{1-3}$ alkyl or NH—$C_{1-3}$ alkyl, each of the O—$C_{1-3}$ alkyl and NH—$C_{1-3}$ alkyl being optionally further substituted with O—$C_{1-3}$ alkyl or NH—$C_{1-3}$ alkyl;

each of $R^{702}$ and $R^{703}$, independently is H, halo, $C_{1-4}$ alkyl, $C_{1-6}$ alkoxyl or $C_6$-$C_{10}$ aryloxy, each optionally substituted with one or more halo;

each of $R^{704}$ and $R^{705}$, independently is $C_{1-4}$ alkyl;

$R^{706}$ is cyclohexyl substituted by $N(C_{1-4}$ alkyl$)_2$ wherein one or both of the $C_{1-4}$ alkyl is substituted with $C_{1-6}$ alkoxy; or $R^{706}$ is tetrahydropyranyl;

$R^{707}$ is $C_{1-4}$ alkyl optionally substituted with one or more groups selected from hydroxyl, $C_{1-4}$ alkoxy, amino, mono- or di-$C_{1-4}$ alkylamino, $C_{3-8}$ cycloalkyl, and 4-7 membered heterocycloalkyl containing 1-3 heteroatoms, wherein the $C_{3-8}$ cycloalkyl or 4-7 membered heterocycloalkyl each independently is further optionally substituted with $C_{1-3}$ alkyl;

$R^{708}$ is $C_{1-4}$ alkyl optionally substituted with one or more groups selected from OH, halo, and $C_{1-4}$ alkoxy, 4-7 membered heterocycloalkyl containing 1-3 heteroatoms, or O—$C_{1-6}$ alkyl, wherein the 4-7 membered heterocycloalkyl can be optionally further substituted with OH or $C_{1-6}$ alkyl; and $n_7$ is 0, 1 or 2.

For example, $R^{706}$ is cyclohexyl substituted by $N(C_{1-4}$ alkyl$)_2$ wherein one of the $C_{1-4}$ alkyl is unsubstituted and the other is substituted with methoxy.

For example, $R^{706}$ is

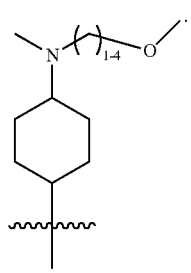

In some embodiments, an EZH2 inhibitor of the disclosure may have the following Formula II:

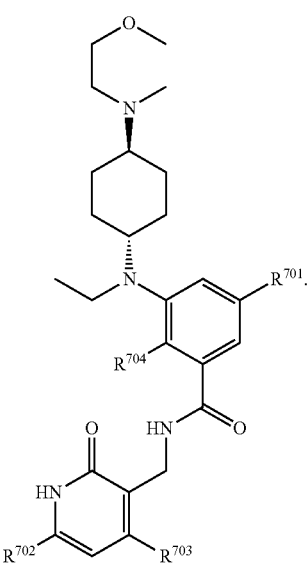

For example, $R^{702}$ is methyl or isopropyl and $R^{703}$ is methyl or methoxyl.

For example, $R^{704}$ is methyl.

For example, $R^{701}$ is $OR^{707}$ and $R^{707}$ is $C_{1-3}$ alkyl optionally substituted with $OCH_3$ or morpholine.

For example, $R^{701}$ is H or F.

For example, $R^{701}$ is tetrahydropyranyl, phenyl, pyridyl, pyrimidyl, pyrazinyl, imidazolyl, or pyrazolyl, each of which is optionally substituted with methyl, methoxy, ethyl substituted with morpholine, or —$OCH_2CH_2OCH_3$.

For example, $R^{708}$ is morpholine, piperidine, piperazine, pyrrolidine, diazepane, or azetidine, each of which is optionally substituted with OH or $C_{1-6}$ alkyl.

For example, $R^{708}$ is morpholine

For example, $R^{708}$ is piperazine substituted with $C_{1-6}$ alkyl.

For example, $R^{708}$ is methyl, t-butyl or $C(CH_3)_2OH$.

In some embodiments, an EZH2 inhibitor of the disclosure may have the following Formula III:

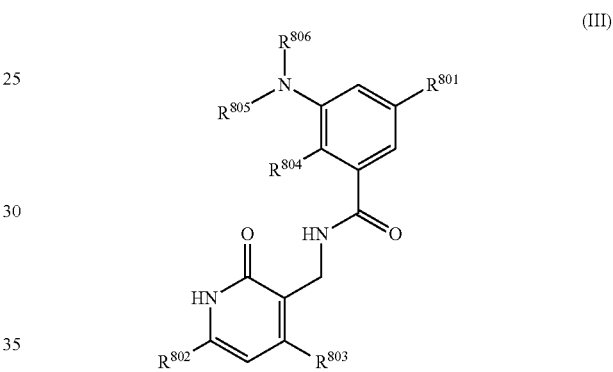

or a pharmaceutically acceptable salt thereof.

In this formula:

$R^{801}$ is $C_{1-6}$ alkyl, $C_{2-6}$ alkenyl, $C_{2-6}$ alkynyl, $C_{3-8}$ cycloalkyl, 4-7 membered heterocycloalkyl containing 1-3 heteroatoms, phenyl or 5- or 6-membered heteroaryl, each of which is substituted with O—$C_{1-6}$ alkyl-$R_x$ or NH—$C_{1-6}$ alkyl-$R_x$, wherein $R_x$ is hydroxyl, O—$C_{1-3}$ alkyl or NH—$C_{1-3}$ alkyl, and $R_x$ is optionally further substituted with O—$C_{1-3}$ alkyl or NH—$C_{1-3}$ alkyl except when $R_x$ is hydroxyl; or $R^{801}$ is phenyl substituted with -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is optionally substituted 4- to 12-membered heterocycloalkyl; and $R^{801}$ is optionally further substituted;

each of $R^{802}$ and $R^{803}$, independently is H, halo, $C_{1-4}$ alkyl, $C_{1-6}$ alkoxyl or $C_6$-$C_{10}$ aryloxy, each optionally substituted with one or more halo;

each of $R^{804}$ and $R^{805}$, independently is $C_{1-4}$ alkyl; and $R^{806}$ is -$Q_x$-$T_x$, wherein $Q_x$ is a bond or $C_{1-4}$ alkyl linker, $T_x$ is H, optionally substituted $C_{1-4}$ alkyl, optionally substituted $C_3$-$C_8$ cycloalkyl or optionally substituted 4- to 14-membered heterocycloalkyl.

For example, each of $Q_x$ and $Q_2$ independently is a bond or methyl linker, and each of $T_x$ and $T_2$ independently is tetrahydropyranyl, piperidinyl substituted by 1, 2, or 3 $C_{1-4}$ alkyl groups, or cyclohexyl substituted by $N(C_{1-4}$ alkyl$)_2$ wherein one or both of the $C_{1-4}$ alkyl is optionally substituted with $C_{1-6}$ alkoxy;

For example, $R^{806}$ is cyclohexyl substituted by $N(C_{1-4}$ alkyl$)_2$ or $R^{806}$ is tetrahydropyranyl.

For example, $R^{806}$ is

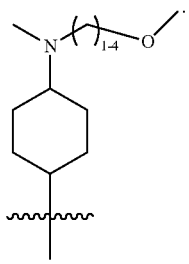

For example, $R^{801}$ is phenyl or 5- or 6-membered heteroaryl substituted with $O-C_{1-6}$ alkyl-$R_x$, or $R^{801}$ is phenyl substituted with $CH_2$-tetrahydropyranyl.

An EZH2 inhibitor of the disclosure may have the following Formula IVa or IVb:

(IVa)

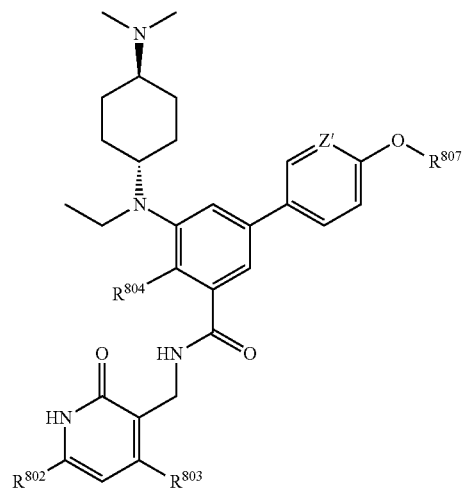

(IVb)

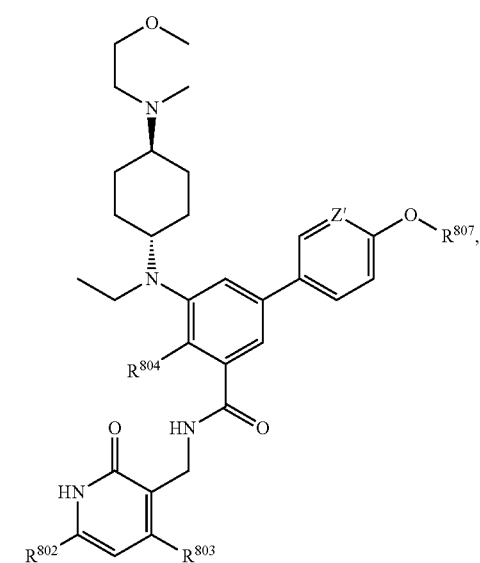

wherein Z' is CH or N, and $R^{807}$ is $C_{2-3}$ alkyl-$R_x$.

For example, $R^{807}$ is $-CH_2CH_2OH$, $-CH_2CH_2OCH_3$, or $-CH_2CH_2OCH_2CH_2OCH_3$.

For example, $R^{802}$ is methyl or isopropyl and $R^{803}$ is methyl or methoxyl.

For example, $R^{804}$ is methyl.

An EZH2 inhibitor of the disclosure may have the following Formula (V):

(V)

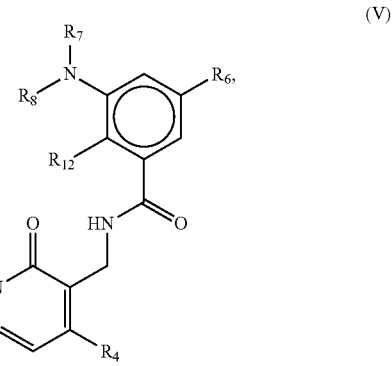

or a pharmaceutically acceptable salt or ester thereof.

In this formula:

$R_2$, $R_4$ and $R_{12}$ are each, independently $C_{1-6}$ alkyl;

$R_6$ is $C_6$-$C_{10}$ aryl or 5- or 6-membered heteroaryl, each of which is optionally substituted with one or more $-Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is H, halo, cyano, $-OR_a$, $-R_aR_b$, $-(NR_aR_bR_c)^+A^-$, $-C(O)R_a$, $-C(O)OR_a$, $-C(O)NR_aR_b$, $-R_bC(O)R_a$, $-R_bC(O)OR_a$, $-S(O)_2R_a$, $-S(O)_2NR_aR_b$, or $R_{S2}$, in which each of $R_a$, $R_b$, and $R_c$, independently is H or $R_{S3}$, $A^-$ is a pharmaceutically acceptable anion, each of $R_{S2}$ and $R_{S3}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S2}$, $R_{S3}$, and the 4 to 12-membered heterocycloalkyl ring formed by $R_a$ and $R_b$, is optionally substituted with one or more $-Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, $-S(O)_2R_d$, $-NR_dR_e$, and $-C(O)NR_dR_e$, each of $R_d$ and $R_e$ independently being H or $C_1$-$C_6$ alkyl, or $-Q_3$-$T_3$ is oxo; or any two neighboring $-Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, $C(O)O-C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is $-Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, $-OR_f$, $-C(O)R_f$, $-C(O)OR_f$, $-C(O)NR_fR_g$, $-C(O)NR_fOR_g$, $-R_fC(O)R_g$, $-S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S4}$ and $R_{S5}$ is optionally substituted with one or more -$Q_5$-$T_5$, wherein $Q_5$ is a bond, C(O), C(O)N$R_k$, N$R_k$C(O), S(O)$_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_q$$R_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo; and $R_8$ is H, halo, hydroxyl, COOH, cyano, $R_{S6}$, O$R_{S6}$, or COO$R_{S6}$, in which $R_{S6}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring having 0 to 2 additional heteroatoms, and the 4 to 11-membered heterocycloalkyl ring formed by $R_7$ and $R_8$ is optionally substituted with one or more -$Q_6$-$T_6$, wherein $Q_6$ is a bond, C(O), C(O)N$R_m$, N$R_m$C(O), S(O)$_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_p$$R_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo.

For example, $R_6$ is $C_6$-$C_{10}$ aryl or 5- or 6-membered heteroaryl, each of which is optionally, independently substituted with one or more -$Q_2$-$T_2$, wherein $Q_2$ is a bond or $C_1$-$C_3$ alkyl linker, and $T_2$ is H, halo, cyano, —O$R_a$, —$R_a$$R_b$, —(N$R_a$$R_b$$R_c$)$^+$A$^-$, —C(O)N$R_a$$R_b$, —$R_b$C(O)$R_a$, —S(O)$_2$$R_a$, or $R_{S2}$, in which each of $R_a$ and $R_b$, independently is H or $R_{S3}$, each of $R_{S2}$ and $R_{S3}$, independently, is $C_1$-$C_6$ alkyl, or $R_a$ and $R_b$, together with the N atom to which they are attached, form a 4 to 7-membered heterocycloalkyl ring having 0 or 1 additional heteroatom, and each of $R_{S2}$, $R_{S3}$, and the 4 to 7-membered heterocycloalkyl ring formed by $R_a$ and $R_b$, is optionally, independently substituted with one or more -$Q_3$-$T_3$, wherein $Q_3$ is a bond or $C_1$-$C_3$ alkyl linker and $T_3$ is selected from the group consisting of halo, $C_1$-$C_6$ alkyl, 4 to 7-membered heterocycloalkyl, O$R_a$, —S(O)$_2$$R_a$, and —N$R_d$$R_e$, each of $R_d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S.

In some embodiments, an EZH2 inhibitor of the disclosure may have the following Formula (VIa):

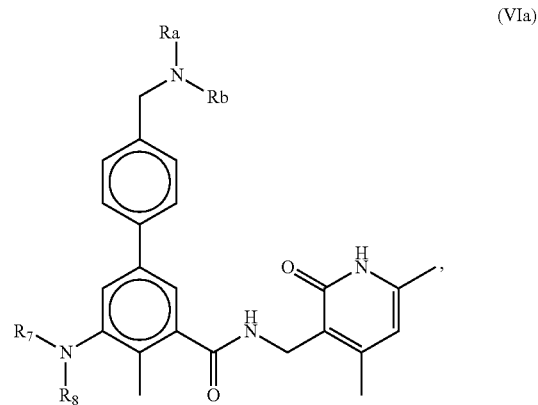

(VIa)

or a pharmaceutically acceptable salts or esters thereof, wherein $R_7$, $R_8$, $R_a$, and $R_b$ are defined herein.

The compounds of Formula (VIa) can include one or more of the following features:

For example, each of $R_a$ and $R_b$ independently is H or $C_1$-$C_6$ alkyl optionally substituted with one or more -$Q_3$-$T_3$.

For example, one of $R_a$ and $R_b$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, morpholinyl, 1,4-diazepanyl, 1,4-oxazepanyl, 2-oxa-5-azabicyclo[2.2.1]heptanyl, 2,5-diazabicyclo[2.2.1]heptanyl, and the like) and the ring is optionally substituted with one or more -$Q_3$-$T_3$.

For example, $R_a$ and $R_b$, together with the N atom to which they are attached, form azetidinyl, pyrrolidinyl, imidazolidinyl, pyrazolidinyl, oxazolidinyl, isoxazolidinyl, triazolidinyl, tetrahydrofuranyl, piperidinyl, 1,2,3,6-tetrahydropyridinyl, piperazinyl, or morpholinyl, and the ring is optionally substituted with one or more -$Q_3$-$T_3$.

For example, one or more -$Q_3$-$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, O$R_d$, COO$R_d$, —S(O)$_2$$R_d$, or —N$R_d$$R_e$.

For example, each of $R_d$ and $R_e$ independently being H or $C_1$-$C_6$ alkyl.

For example, $R_7$ is $C_3$-$C_8$ cycloalkyl or 4 to 7-membered heterocycloalkyl, each optionally substituted with one or more -$Q_5$-$T_5$.

For example, $R_7$ is piperidinyl, tetrahydropyran, tetrahydro-2H-thiopyranyl, cyclopentyl, cyclohexyl, pyrrolidinyl, or cycloheptyl, each optionally substituted with one or more -$Q_5$-$T_5$.

For example, $R_7$ is cyclopentyl cyclohexyl or tetrahydro-2H-thiopyranyl, each of which is optionally substituted with one or more -$Q_5$-$T_5$.

For example, $Q_5$ is NHC(O) and $T_5$ is $C_1$-$C_6$ alkyl or $C_1$-$C_6$ alkoxy, each For example, one or more -$Q_5$-$T_5$ are oxo.

For example, $R_7$ is 1-oxide-tetrahydro-2H-thiopyranyl or 1,1-dioxide-tetrahydro-2H-thiopyranyl.

For example, $Q_5$ is a bond and $T_5$ is amino, mono-$C_1$-$C_6$ alkylamino, di-$C_1$-$C_6$ alkylamino.

For example, $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 7-membered heterocycloalkyl.

For example, $R_8$ is H or $C_1$-$C_6$ alkyl which is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino.

For example, $R_8$ is H, methyl, or ethyl.

In some embodiments, the compound suitable for the methods disclosed herein is EPZ-6438 (tazemetostat):

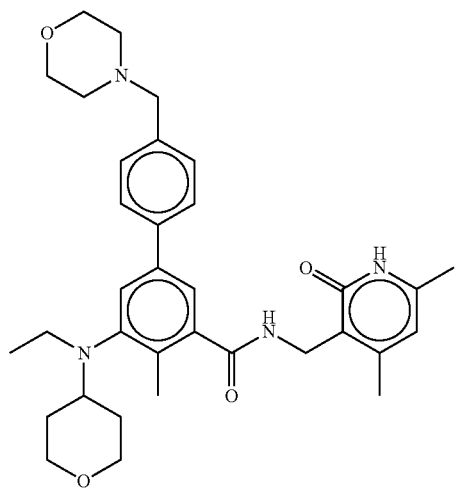

(A)

or a pharmaceutically acceptable salt thereof.

EPZ-6438 or a pharmaceutically acceptable salt thereof, as described herein, is potent in targeting both WT and mutant EZH2. EPZ-6438 is orally bioavailable and has high selectivity to EZH2 compared with other histone methyltransferases (i.e. >20,000 fold selectivity by Ki). Importantly, EPZ-6438 has target methyl mark inhibition that results in the killing of genetically defined cancer cells in vitro. Animal models have also shown sustained in vivo efficacy following inhibition of target methyl mark. Clinical trial results described herein also demonstrate the safety and efficacy of EPZ-6438.

In some embodiments, EPZ-6438 or a pharmaceutically acceptable salt thereof is administered to the subject at a dose of approximately 100 mg to approximately 3200 mg daily, such as about 100 mg BID to about 1600 mg BID (e.g., 100 mg BID, 200 mg BID, 400 mg BID, 800 mg BID, or 1600 mg BID), for treating a NHL. In some embodiments the dose is 800 mg BID.

In some embodiments, a compound (e.g., EZH2 inhibitor) that can be used in any methods presented here is:

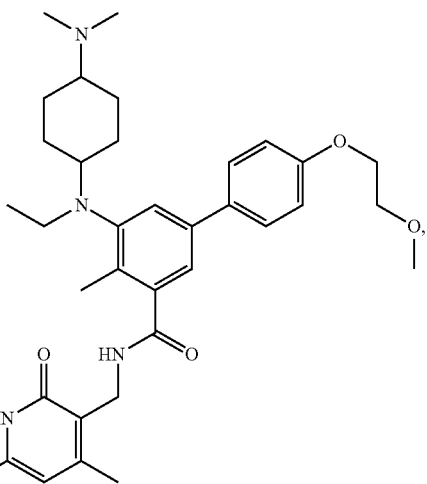

(B)

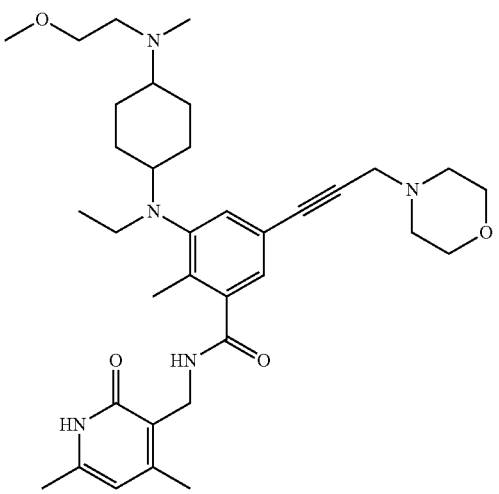

(C)

or

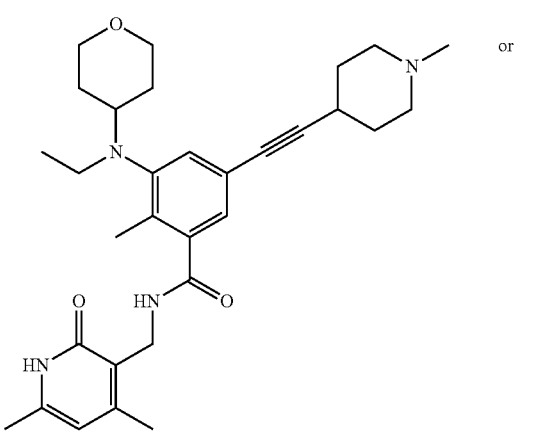

(D)

or

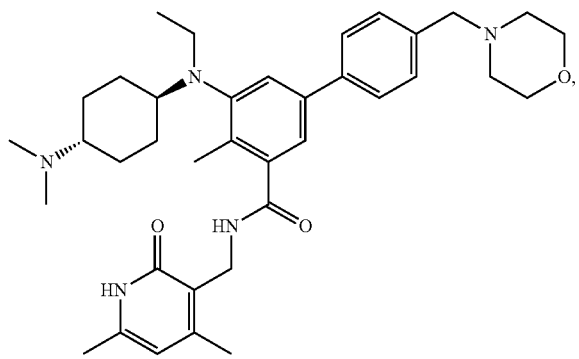

(E)

or stereoisomers thereof or pharmaceutically acceptable salts and solvates thereof.

In certain embodiments, a compound that can be used in any methods presented here is Compound F:

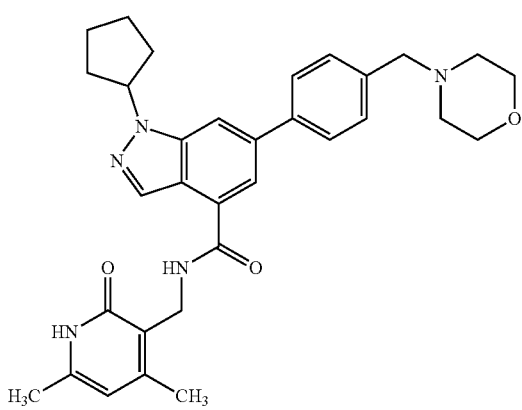

(F)

or pharmaceutically acceptable salts thereof.

In some embodiments, a compound (e.g., EZH2 inhibitor) that can be used in any methods presented here is GSK-126 having the following formula:

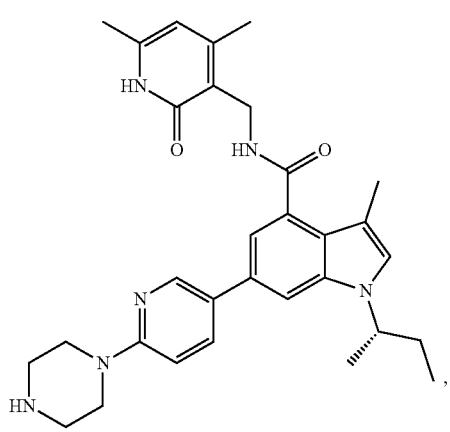 [SMILES: CC[C@H](C)n1cc(C)c2c(C(=O)NCc3c(C)cc(C)[nH]c3=O)cc(-c3ccc(N4CCNCC4)nc3)cc21]

stereoisomers thereof, or pharmaceutically acceptable salts or solvates thereof.

In certain embodiments, a compound that can be used in any methods presented here is Compound G:

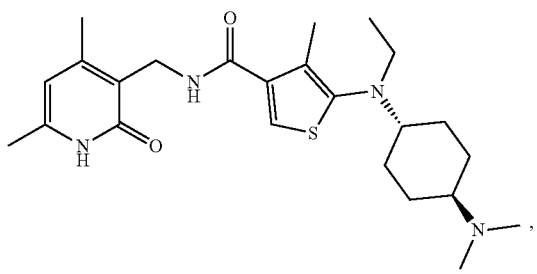

(G)

or stereoisomers thereof or pharmaceutically acceptable salts and solvates thereof.

In certain embodiments, a compound (e.g., EZH2 inhibitor) that can be used in any methods presented here is any of Compounds Ga-Gc:

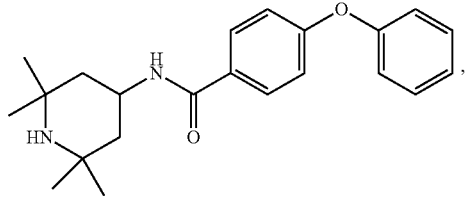

(Ga)

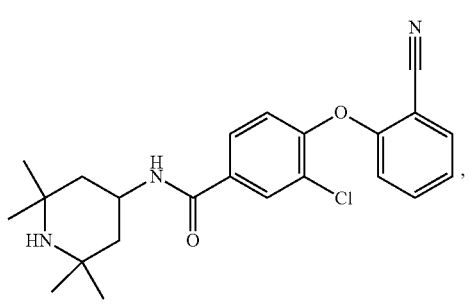

(Gb)

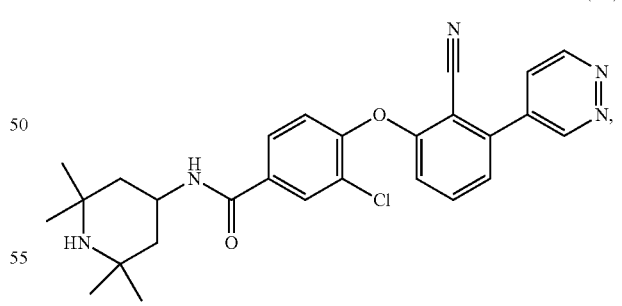

(Gc)

or a stereoisomer, pharmaceutically acceptable salt or solvate thereof.

In certain embodiments, a compound (e.g., EZH2 inhibitor) that can be used in any methods presented here is CPI-1205 or GSK343.

Additional suitable EZH2 inhibitors will be apparent to those skilled in the art. In some embodiments of the strategies, treatment modalities, methods, combinations, and compositions provided herein, the EZH2 inhibitor is an EZH2 inhibitor described in U.S. Pat. No. 8,536,179 (describing GSK-126 among other compounds and corresponding to WO 2011/140324), the entire contents of each of which are incorporated herein by reference.

In some embodiments of the strategies, treatment modalities, methods, combinations, and compositions provided herein, the EZH2 inhibitor is an EZH2 inhibitor described in PCT/US2014/015706, published as WO 2014/124418, in PCT/US2013/025639, published as WO 2013/120104, and in U.S. Ser. No. 14/839,273, published as US 2015/0368229, the entire contents of each of which are incorporated herein by reference.

In some embodiments, the compound disclosed herein is the compound itself, i.e., the free base or "naked" molecule. In another embodiment, the compound is a salt thereof, e.g., a mono-HCl or tri-HCl salt, mono-HBr or tri-HBr salt of the naked molecule.

Compounds disclosed herein that contain nitrogens can be converted to N-oxides by treatment with an oxidizing agent (e.g., 3-chloroperoxybenzoic acid (mCPBA) and/or hydrogen peroxides) to afford other compounds suitable for any methods disclosed herein. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds disclosed herein can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds disclosed herein may be depicted as different chiral isomers or geometric isomers. It should also be understood that when compounds have chiral isomeric or geometric isomeric forms, all isomeric forms are intended to be included in the scope of the disclosure, and the naming of the compounds does not exclude any isomeric forms.

Furthermore, the structures and other compounds discussed in this disclosure include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerization is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

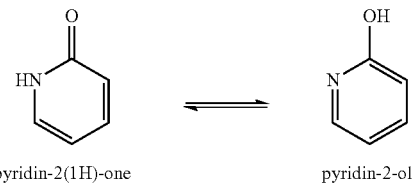

pyridin-2(1H)-one        pyridin-2-ol

It is to be understood that the compounds disclosed herein may be depicted as different tautomers. It should also be understood that when compounds have tautomeric forms, all tautomeric forms are intended to be included in the scope of the disclosure, and the naming of the compounds does not exclude any tautomer form.

The compounds disclosed herein include the compounds themselves, as well as their salts and their solvates, if applicable. A salt, for example, can be formed between an anion and a positively charged group (e.g., amino) on an aryl- or heteroaryl-substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an aryl- or heteroaryl-substituted benzene compound. Suitable cations include sodium ion, potassium ion, magnesium ion, calcium ion, and an ammonium cation such as tetramethylammonium ion. The aryl- or heteroaryl-substituted benzene compounds also include those salts containing quaternary nitrogen atoms. In the salt form, it is understood that the ratio of the compound to the cation or anion of the salt can be 1:1, or any ration other than 1:1, e.g., 3:1, 2:1, 1:2, or 1:3.

Additionally, the compounds disclosed herein, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds disclosed herein are aryl- or heteroaryl-substituted benzene compounds.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

In certain aspects, "combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A composition of the disclosure may comprise a compound of Formulae (I)-(VIa), or a pharmaceutically acceptable salt thereof, and one or more second agents, or pharmaceutically acceptable salts thereof. The disclosure provides for the administration of a compound of Formulae (I)-(VIa) or a pharmaceutically acceptable salt thereof, and one or more second agents, or pharmaceutically acceptable salts, as a co-formulation or separate formulations, wherein the administration of formulations is simultaneous, sequential, or in alternation. In certain embodiments, the one or more second agents can be one or more therapeutic agents that are recognized in the art as being useful to treat the disease or condition being treated by the composition of the disclosure. In some embodiments, the one or more second agents can be one or more therapeutic agents that are not recognized in the art as being useful to treat the disease or condition being treated by the composition of the disclosure. In one aspect, the one or more second agents can be one or more a therapeutic agents that impart a beneficial attribute to the composition of the disclosure (e.g., an agent that affects the viscosity of the composition). The beneficial attribute to the composition of the disclosure includes, but is not limited to, pharmacokinetic or pharmacodynamic co-action resulting from the combination of a compound of Formulae (I)-(VIa) and one or more second agents.

The therapeutic agents set forth below are for illustrative purposes and not intended to be limiting. The disclosure includes at least one other agent which may be a therapeutic agent selected from the lists below. The disclosure can include more than one second agents, e.g., two, three, four, or five other therapeutic agents such that the composition of the disclosure can perform its intended function.

In some embodiments, the other therapeutic agent is an anticancer agent. In some embodiments, the anticancer agent is a compound that affects histone modifications, such as an HDAC inhibitor (such as Zolinza® or Farydak®). In certain embodiments, an anticancer agent is selected from the group consisting of chemotherapeutics (such as 2CdA, 5-FU, 6-Mercaptopurine, 6-TG, Abraxane™, Accutane®, Actinomycin-D, Adriamycin®, Alimta®, Alkeran® all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Etopophos®, Fludara®, FUDR®, Gemzar®, Gleevec®, hexamethylmelamine, Hycamtin®, Hydrea®, Idamycin®, Ifex®, Imbruvica®, ixabepilone, Ixempra®, L-asparaginase, Leukeran®, liposomal Ara-C, L-PAM, Lysodren, mafosfamide, Marqibo®, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Toposar®, Treanda®, Trisenox®, Valstar®, Velban®, Vidaza™, vincristine sulfate, VM 26, Xeloda® and Zanosar®); biologics (such as Alpha Interferon, Bacillus Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™, Thalomid®, Tykerb®, Velcade® and Zevalin™); corticosteroids, (such as dexamethasone sodium phosphate, DeltaSone® and Delta-Cortef®); glucocorticoid receptor agonists (such as Baycadron®, Maxidex®, Ozurdex®, Econopred®, Omnipred®, or Millipred®); hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®); and radiopharmaceuticals (such as Iodotope®, Metastron®, Phosphocol® and Samarium SM-153); immunomodulatory drugs (such as Pomalyst®, Revlimid® and Thalidomid®); proteasome inhibitors (such as Kyprolis®, Ninlaro® and Velcade®); bcl-2 inhibitors (such as Venclexta®).

Exemplary glucocorticoid receptor agonists include but are not limited to, dexamethasone (Baycadron®, Maxidex®, Ozurdex®), methylprednisolone (Depo-Medrol®, Solu-Medrol®), or prednisolone (Econopred®, Omnipred®, Millipred®).

Exemplary immunomodulatory drugs include, but are not limited to, lenalidomide (Revlimid®), pomalidomide (Pomalyst®) and thalidomide (Thalidomid®);

Exemplary proteasome inhibitors, include but are not limited to, bortezomib (Velcade®), carfilzomib (Kyprolis®) and ixazomib (Ninlaro®), Exemplary Bcl-2 inhibitors include, but are not limited to, venetoclax (Venclexta®).

In some embodiments, the other therapeutic agent is a chemotherapeutic agent (also referred to as an anti-neoplastic agent or anti-proliferative agent), selected from the group including an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan®; Neosar®); chlorambucil (Leukeran®); melphalan (Alkeran®); carmustine (BiCNU®); busulfan (Busulfex®); lomustine (CeeNU®); dacarbazine (DTIC-Dome®); oxaliplatin (Eloxatin®); carmustine (Gliadel®); ifosfamide (Ifex®); mechlorethamine (Mustargen); busulfan (Myleran®); carboplatin (Paraplatin®); cisplatin (CDDP®; Platinol®); temozolomide (Temodar®); thiotepa (Thioplex®); bendamustine (Treanda®); or streptozocin (Zanosar®).

Exemplary antibiotics include, but are not limited to, doxorubicin (Adriamycin®); doxorubicin liposomal (Doxil®); mitoxantrone (Novantrone®); bleomycin (Blenoxane®); daunorubicin (Cerubidine®); daunorubicin liposomal (DaunoXome®); dactinomycin (Cosmegen®); epirubicin (Ellence®); idarubicin (Idamycin®); plicamycin (Mithracin®); mitomycin (Mutamycin®); pentostatin (Nipent®); or valrubicin (Valstar®).

Exemplary anti-metabolites include, but are not limited to, fluorouracil (Adrucil®); capecitabine (Xeloda®); hydroxyurea (Hydrea®); mercaptopurine (Purinethol®); pemetrexed (Alimta); fludarabine (Fludara®); nelarabine (Arranon®); cladribine (Cladribine Novaplus®); clofarabine (Clolar®); cytarabine (Cytosar-U®); decitabine (Dacogen®); cytarabine liposomal (DepoCyt®); hydroxyurea (Droxia®); pralatrexate (Folotyn®); floxuridine (FUDR®); gemcitabine (Gemzar®); cladribine (Leustatin®); fludarabine (Oforta®); methotrexate (MTX®; Rheumatrex®); methotrexate (Trexall®); thioguanine (Tabloid®); TS-1 or cytarabine (Tarabine PFS®).

Exemplary detoxifying agents include, but are not limited to, amifostine (Ethyol®) or mesna (Mesnex®).

Exemplary interferons include, but are not limited to, interferon alfa-2b (Intron A®) or interferon alfa-2a (Roferon-A®).

Exemplary polyclonal or monoclonal antibodies include, but are not limited to, trastuzumab (Herceptin®); ofatumumab (Arzerra®); bevacizumab (Avastin®); rituximab (Rituxan®); cetuximab (Erbitux®); panitumumab (Vectibix®); tositumomab/iodine131 tositumomab (Bexxar®); alemtuzumab (Campath®); ibritumomab (Zevalin®; In-111®; Y-90 Zevalin®); gemtuzumab (Mylotarg®); eculizumab (Solirisg) ordenosumab.

Exemplary EGFR inhibitors include, but are not limited to, gefitinib (Iressa); lapatinib (Tykerb®); cetuximab (Erbitux®); erlotinib (Tarceva®); panitumumab (Vectibix®); PKI-166; canertinib (CI-1033); matuzumab (Emd7200) or EKB-569.

Exemplary HER2 inhibitors include, but are not limited to, trastuzumab (Herceptin®); lapatinib (Tykerb®) or AC-480.

Histone Deacetylase Inhibitors include, but are not limited to, vorinostat (Zolinza®) and panobinostat (Farydak®).

Exemplary hormones include, but are not limited to, tamoxifen (Soltamox; Nolvadex®); raloxifene (Evista®); megestrol (Megace®); leuprolide (Lupron®; Lupron Depot®; Eligard®; Viadur®) ; fulvestrant (Faslodex®); letrozole (Femara®); triptorelin (Trelstar LA®; Trelstar Depot®) ; exemestane (Aromasin®) ; goserelin (Zoladex®) ; bicalutamide (Casodex®); anastrozole (Arimidex®); fluoxymesterone (Androxy®; Halotestin®); medroxyprogesterone (Provera®; Depo-Provera®); estramustine (Emcyt®); flutamide (Eulexin®); toremifene (Fareston®); degarelix (Firmagon®); nilutamide (Nilandron®); abarelix (Plenaxis®); or testolactone (Teslac®).

Exemplary mitotic inhibitors include, but are not limited to, paclitaxel (Taxol®; Onxol®; Abraxane®); docetaxel (Taxotere®); vincristine (Oncovin®; Vincasar PFS®); vinblastine (Velban®); etoposide (Toposar®; Etopophos®; VePesid®); teniposide (Vumon®); ixabepilone (Ixempra®); nocodazole; epothilone; vinorelbine (Navelbine®); camptothecin (CPT); irinotecan (Camptosar®); topotecan (Hycamtin®); amsacrine or lamellarin D (LAM-D).

Exemplary MTOR inhibitors include, but are not limited to, everolimus (Afinitor®) or temsirolimus (Torisel®); rapamune, ridaforolimus; or AP23573.

Exemplary VEGF/VEGFR inhibitors include, but are not limited to, bevacizumab (Avastin®); sorafenib (Nexavar®); sunitinib (Sutent®); ranibizumab; pegaptanib; or vandetinib.

Exemplary microtubule targeting drugs include, but are not limited to, paclitaxel, docetaxel, vincristine, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid®); azacitidine (Vidaza®); bortezomib (Velcade®) asparaginase (Elspar®); ibrutinib (Imbruvica®); levamisole (Ergamisol®); mitotane (Lysodren®); procarbazine (Matulane); pegaspargase (Oncaspar®); denileukin diftitox (Ontak®); porfimer (Photofrin®); aldesleukin (Proleukin®); lenalidomide (Revlimid®); bexarotene (Targretin®); thalidomide (Thalomid®); temsirolimus (Torisel®); arsenic trioxide (Trisenox®); verteporfin (Visudyn®); mimosine (Leucenol®); (1M tegafur—0.4 M 5-chloro-2,4-dihydroxypyrimidine-1 M potassium oxonate), or lovastatin.

In other aspects, the other therapeutic agent is a chemotherapeutic agent or a cytokine such as G-CSF (granulocyte colony stimulating factor).

In yet other aspects, the other therapeutic agents can be standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™), CHOP (cyclophosphamide, hydroxydaunorubicin, oncovin, and prednisone or prednisolone), R-CHOP (rituximab, cyclophosphamide, hydroxydaunorubicin, oncovin, prednisone or prednisolone), CVP (cyclophosphamide, vincristine, and prednisone), hyper-CVAD (hyperfractionated cyclophosphamide, vincristine, doxorubicin, and prednisone), or CMFP (cyclophosphamide, methotrexate, 5-fluorouracil and prednisone).

In other aspects, the other therapeutic agents can be an inhibitor of an enzyme, such as a receptor or non-receptor kinase. Receptor and non-receptor kinases are, for example, tyrosine kinases or serine/threonine kinases. Kinase inhibitors described herein are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Ab1), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-ß, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK, Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

Exemplary tyrosine kinase inhibitors include, but are not limited to, erlotinib (Tarceva®); gefitinib (Iressa®); imatinib (Gleevec®); sorafenib (Nexavar®); sunitinib (Sutent®); trastuzumab (Herceptin®); bevacizumab (Avastin®); rituximab (Rituxan®); lapatinib (Tykerb®); cetuximab (Erbitux®); panitumumab (Vectibix®); everolimus (Afinitor®); alemtuzumab (Campath®); gemtuzumab (Mylotarg®); temsirolimus (Torisel®); pazopanib (Votrient®); dasatinib (Sprycel®); nilotinib (Tasigna®); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888. More examples of the other therapeutic agents suitable to be used in combination with compounds of Formulae (I)-(VIa) or a pharmaceutically acceptable salt thereof are disclosed in co-pending U.S. Application No. 61/992,881 filed May 013, 2014 and International Application No. PCT/US2014/069167 filed Dec. 8, 2014, the contents of each of which are incorporated herein by reference in their entireties.

In other aspects, a composition disclosed herein, or a pharmaceutically acceptable salt, solvate, analog or derivative thereof, is administered in combination with radiation therapy. Radiation therapy can also be administered in combination with a composition disclosed herein and another chemotherapeutic agent described herein as part of a multiple agent therapy.

The disclosure provides methods for combination therapy in which a composition comprising a compound of Formulae (I)-(VIa) or a pharmaceutically acceptable salt thereof, and one or more second agents are administered to a subject in need for treatment of a disease or cancer. The combination therapy can also be administered to cancer cells to inhibit proliferation or induce cell death. In one aspect, a compound of Formulae (I)-(VIa) or a pharmaceutically acceptable salt thereof is administered subsequent to administration of the composition of the disclosure comprising a compound of Formulae (I)-(VIa) or a pharmaceutically acceptable salt thereof, and one or more second agents. In one aspect, a compound of Formulae (I)-(VIa) or a pharmaceutically acceptable salt thereof is administered prior to administration of the composition of the disclosure comprising a compound of Formulae (I)-(VIa) or a pharmaceutically acceptable salt thereof, and one or more second agents. In one aspect, a compound of Formulae (I)-(VIa) or a pharmaceutically acceptable salt thereof is administered subsequent to administration of one or more second agents, such that the second agents are administered either in a single composition or in two or more compositions, e.g. administered simultaneously, sequentially, or in alternation. In one aspect, a compound of Formulae (I)-(VIa) or a pharmaceutically acceptable salt thereof is administered prior to administration of one or more therapeutic agents, such that the second agents are administered either in a single composition or in two or more compositions, e.g. administered simultaneously, sequentially, or in alternation.

In some embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with (e.g., at the same time as, in temporal proximity to, or in overlapping time periods with the administration of) one or more therapeutic agents which are standard of care agents for treating a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma. Exemplary standard of care agents and treatment modalities for the treatment of a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma a are described herein and additional suitable standard of care agents and treatment modalities will be apparent to the skilled artisan based on the present disclosure or will otherwise be known in the art. For example, in some aspects of the present disclosure, methods and treatment modalities for a malignant rhabdoid tumor (MRT), a rhabdoid tumor of the kidney (RTK), an atypical teratoid/rhabdoid tumor (AT/RT), an epithelioid malignant peripheral nerve sheath tumor, a myoepithelial carcinoma, and/or a renal medullary carcinoma are provided in which a compound of Formulae (I)-(VIa) or a pharmaceutically acceptable salt thereof, or a composition comprising a compound of Formulae (I)-(VIa) or a pharmaceutically acceptable salt thereof, is administered in combination with doxorubicin, cytarabine, vincristine, everolimus, alisertib, topotecan, etoposide, carboplatin, entinostat, panobinostat, romidepsin, palbociclib, abemaciclib, selumetinib, trametinib or combinations thereof. In some embodiments, the compound of Formulae (I)-(VIa) is tazemetostat.

In some embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with two, three, four, five or more additional therapeutic agents. In one aspect, a compound of Formulae (I)-(VIa) or a pharmaceutically acceptable salt thereof, or a composition comprising a compound of Formulae (I)-(VIa) or a pharmaceutically acceptable salt thereof, is administered in combination with two additional therapeutic agents.

In some embodiments, standard of care agents and treatment modalities include, for example, first line treatment agents and treatment modalities, second, third, and fourth line treatment agents and modalities, maintenance treatment agents and modalities, and 4+ line treatment agents and modalities.

In one aspect, a compound of Formulae (I)-(VIa) or a pharmaceutically acceptable salt thereof, or a composition comprising a compound of Formulae (I)-(VIa) or a pharmaceutically acceptable salt thereof, is administered in combination with doxorubicin, cytarabine, vincristine, everolimus, alisertib, topotecan, etoposide, carboplatin, entinostat, panobinostat, romidepsin, palbociclib, abemaciclib, selumetinib, trametinib or combinations thereof. In some embodiments, the compound of Formulae (I)-(VIa) is tazemetostat.

In some embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with a general chemotherapeutic agent. In further embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with doxorubicin. In some embodiments, a compound of Formulae (I)-(VIa) or a pharmaceutically acceptable salt thereof, or a composition comprising a compound of Formulae (I)-(VIa) or a pharmaceutically acceptable salt thereof is administered in combination with an anti-metabolite. In further embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with cytarabine. In some embodiments, a compound of Formulae (I)-(VIa) or a pharmaceutically acceptable salt thereof, or a composition comprising a compound of Formulae (I)-(VIa) or a pharmaceutically acceptable salt thereof is administered in combination with a microtubule targeting drug. In further embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with paclitaxel, docetaxel, or vincristine. In some embodiments, a compound of Formulae (I)-(VIa) or a pharmaceutically acceptable salt thereof, or a composition comprising a compound of Formulae (I)-(VIa) or a pharmaceutically acceptable salt thereof is administered in combination with a serine/threonine kinase inhibitor. In further embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with everolimus. In some embodiments, a compound of Formulae (I)-(VIa) or a pharmaceutically acceptable salt thereof, or a composition comprising a compound of Formulae (I)-(VIa) or a pharmaceutically acceptable salt thereof is administered in combination with an aurora A kinase inhibitor. In further embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with alisertib. In some embodiments, a compound of Formulae (I)-(VIa) or a pharmaceutically acceptable salt thereof, or a composition comprising a compound of Formulae (I)-(VIa) or a pharmaceutically acceptable salt thereof is administered in combination with a topoisomerase inhibitor. In further embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with topotecan or etoposide. In some embodiments, a compound of Formulae (I)-(VIa) or a pharmaceutically acceptable salt thereof, or a composition comprising a compound of Formulae (I)-(VIa) or a pharmaceutically acceptable salt thereof is administered in combination with DNA binding or crosslinking agent. In further embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with carboplatin. In some embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with an HDAC inhibitor. In further embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with entinostat, panobinostat, or romidepsin. In some embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with a CDK inhibitor. In further embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with palbociclib and abemaciclib. In some embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with a MEK inhibitor. In further embodiments, a compound of Formulae (I)-(VIa) or a pharmaceutically acceptable salt thereof, or a composition comprising a compound of Formulae (I)-(VIa) or a pharmaceutically acceptable salt thereof, is administered in combination with selumetinib and trametinib. In some embodiments, the compound of Formulae (I)-(VIa) is tazemetostat.

The disclosure further provides methods for combination therapy in which an EZH2 inhibitor, e.g., tazemetostat or a pharmaceutically acceptable salt thereof, and doxorubicin are administered to a subject in need for treatment of a disease or cancer. In some embodiments, the disclosure provides methods for combination therapy in which an EZH2 inhibitor, e.g., tazemetostat or a pharmaceutically acceptable salt thereof, and cytarabine are administered to a subject in need for treatment of a disease or cancer. In some embodiments, the disclosure provides methods for combination therapy in which an EZH2 inhibitor, e.g., tazemetostat or a pharmaceutically acceptable salt thereof, and vincristine are administered to a subject in need for treatment of a disease or cancer. In some embodiments, the disclosure provides methods for combination therapy in which an EZH2 inhibitor, e.g., tazemetostat or a pharmaceutically acceptable salt thereof, and everolimus are administered to a subject in need for treatment of a disease or cancer. In some embodiments, the disclosure provides methods for combination therapy in which an EZH2 inhibitor, e.g., tazemetostat or a pharmaceutically acceptable salt thereof, and alisertib are administered to a subject in need for treatment of a disease or cancer. In some embodiments, the disclosure provides methods for combination therapy in which an EZH2 inhibitor, e.g., tazemetostat or a pharmaceutically acceptable salt thereof, and topotecan are administered to a subject in need for treatment of a disease or cancer. In some embodiments, the disclosure provides methods for combination therapy in which an EZH2 inhibitor, e.g., tazemetostat or a pharmaceutically acceptable salt thereof, and etoposide are administered to a subject in need for treatment of a disease or cancer. In some embodiments, the disclosure provides methods for combination therapy in which an EZH2 inhibitor, e.g., tazemetostat or a pharmaceutically acceptable salt thereof, and carboplatin are administered to a subject in need for treatment of a disease or cancer. In some embodiments, the disclosure provides methods for combination therapy in which an EZH2 inhibitor, e.g., tazemetostat or a pharmaceutically acceptable salt thereof, and entinostat are administered to a subject in need for treatment of a disease or cancer. In some embodiments, the disclosure provides methods for combination therapy in which an EZH2 inhibitor, e.g., tazemetostat or a pharmaceutically acceptable salt thereof, and panobinostat are administered to a subject in need for treatment of a disease or cancer. In some embodiments, the disclosure provides methods for combination therapy in which an EZH2 inhibitor, e.g., tazemetostat or a pharmaceutically acceptable salt thereof, and romidepsin are administered to a subject in need for treatment of a disease or cancer. In some embodiments, the disclosure provides methods for combination therapy in which an EZH2 inhibitor, e.g., tazemetostat or a pharmaceutically acceptable salt thereof, and palbociclib are administered to a subject in need for treatment of a disease or cancer. In some embodiments, the disclosure provides methods for combination therapy in which an EZH2 inhibitor, e.g., tazemetostat or a pharmaceutically acceptable salt thereof, and abemaciclib are administered to a subject in need for treatment of a disease or cancer. In some embodiments, the disclosure provides methods for combination therapy in which an EZH2 inhibitor, e.g., tazemetostat or a pharmaceutically acceptable salt thereof, and selumetinib are administered to a subject in need for treatment of a disease or cancer. In some embodiments, the disclosure provides methods for combination therapy in which an EZH2 inhibitor, e.g., tazemetostat or a pharmaceutically acceptable salt thereof, and trametinib are administered to a subject in need for treatment of a disease or cancer. In some embodiments, the disclosure provides methods for combination therapy in which an EZH2 inhibitor, e.g., tazemetostat or a pharmaceutically acceptable salt thereof, and X-ray irradiation are administered to a subject in need for treatment of a disease or cancer. In one aspect, the disease or cancer to be treated is a malignant rhabdoid tumor (MRT). In other aspects, the disease or cancer to be treated is a rhabdoid tumor of the kidney (RTK). In other aspects, the disease or cancer to be treated is an atypical teratoid/rhabdoid tumor (AT/RT). In other aspects, the disease or cancer to be treated is an epithelioid malignant peripheral nerve sheath tumor. In other aspects, the disease or cancer to be treated is a myoepithelial carcinoma. In other aspects, the disease or cancer to be treated is a renal medullary carcinoma.

In certain embodiments, "combination therapy" is intended to embrace administration of these therapeutic agents in a sequential manner, wherein each therapeutic agent is administered at a different time, as well as administration of these therapeutic agents, or at least two of the therapeutic agents concurrently, or in a substantially simultaneous manner. Simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected is administered by intravenous injection while the one or more second agents of the combination are administered orally. Alternatively, for example, all therapeutic agents are administered orally or all therapeutic agents are administered by intravenous injection. Therapeutic agents may also be administered in alternation.

In certain aspects of the invention, the combination therapies featured in the disclosure can result in a synergistic effect in the treatment of a disease or cancer. A "synergistic effect" is defined as where the efficacy of a combination of therapeutic agents is greater than the sum of the effects of any of the agents given alone. A synergistic effect may also be an effect that cannot be achieved by administration of any of the compounds or other therapeutic agents as single agents. The synergistic effect may include, but is not limited to, an effect of treating cancer by reducing tumor size, inhibiting tumor growth, or increasing survival of the subject. The synergistic effect may also include reducing cancer cell viability, inducing cancer cell death, and inhibiting or delaying cancer cell growth.

In certain aspects of the invention "combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In other aspects, a composition of the disclosure, or a pharmaceutically acceptable salt, solvate, analog or derivative thereof, are administered in combination with radiation therapy. Radiation therapy can also be administered in combination with a composition of the disclosure and another therapeutic agent described herein as part of a multiple agent therapy.

In some embodiments, combination therapy is be achieved by administering two or more treatment modalities, e.g., a compound of Formulae (I)-(VIa) and one or more second agents as described herein, wherein the compound of Formulae (I)-(VIa) is formulated and administered separately from the one or more second agents. In some embodiments, combination treatment is achieved by administering two or more agents in a single formulation. Other combinations are also encompassed by combination therapy. For example, two agents can be formulated together and administered in conjunction with a separate formulation containing a third agent. While, in some embodiments, the two or more agents in the combination therapy can be administered simultaneously, they need not be. For example, administration of a first agent (or combination of agents) can precede administration of one or more second agents (e.g., a combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

In some embodiments, a first agent (e.g. an EZH2 inhibitor, e.g., a compound of Formulae (I)-(VIa)) and one or more additional treatment modalities are administered in temporal proximity (e.g., a compound of Formulae (I)-(VIa) and the one or more additional treatment modalities can be administered simultaneously or sequentially). Accordingly, the present disclosure provides a method of treating or preventing a disease comprising administering a first agent (e.g. an EZH2 inhibitor, e.g., a compound of Formulae (I)-(VIa)) and one or more additional treatment modalities in temporal proximity.

In some embodiments, "temporal proximity" means that administration of one treatment modality (e.g., a first agent, e.g., an EZH2 inhibitor) occurs within a time period before or after the administration of another treatment modality (e.g., one more or second therapeutic agents or radiation therapy), such that the therapeutic effect of the one treatment modality overlaps with the therapeutic effect of the other treatment modality. In some embodiments, the therapeutic effect of the one treatment modality completely overlaps with the therapeutic effect of the other treatment modality. In some embodiments, "temporal proximity" means that administration of one treatment modality (e.g., one more or second therapeutic agents or radiation therapy), occurs within a time period before or after the administration of another treatment modality, such that there is a synergistic or sensitizing effect between one treatment modality and the another treatment modality. "Temporal proximity" may vary according to various factors, including but not limited to, the age, gender, weight, genetic background, medical condition, disease history, and treatment history of the subject to which the treatment modalities are to be administered; the disease or condition to be treated or ameliorated; the therapeutic outcome to be achieved; the dosage, dosing frequency, and dosing duration of the treatment modalities; the pharmacokinetics and pharmacodynamics of the treatment modalities; and the route(s) through which the treatment modalities are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one treatment modality can occur in temporal proximity to a single administration of another treatment modality. In some embodiments, temporal proximity may change during a treatment cycle or within a dosing regimen.

In some embodiments, the administration schedules of the two or more agents, e.g., a compound of Formulae (I)-(VIa) and one or more second agents as described herein, differs. For example, in some embodiments, the first agent, e.g., an EZH2 inhibitor as provided herein, is administered daily, e.g., twice daily at a dose between 100 mg and 1600 mg, and one or more second agents, e.g., an anti-cancer agent provided herein is/are administered once per week, once every two weeks, once every three weeks, or once every four weeks. In some embodiments, one agent, e.g., the EZH2 inhibitor is administered continuously over a treatment period, e.g., daily (e.g., BID), for a period of one month, two months, three months, four months, etc., while one or more second agents, e.g., an anti-cancer agent provided herein, is/are administered during this time period in sequential treatment periods with intermittent non-treatment periods, e.g., two weeks of treatment followed by one week of non-treatment. Combination treatment can be achieved in such embodiments, by having at least one treatment period of one agent overlap with at least one treatment period of the other agent.

In one aspect, the disclosure provides methods for sensitizing or priming a subject to administration of a treatment modality. In some embodiments, a subject is sensitized or primed for responding to a treatment modality by administering an EZH2 inhibitor. Thus, in one aspect, an EZH2 inhibitor is administered to a subject prior to the administration of a treatment modality, resulting in the sensitization or priming of the subject. Consequently the subject is more sensitive to the treatment modality. The EZH2 inhibitor may be a compound of Formulae (I)-(VIa). For example, the EZH2 inhibitor is tazemetostat. In some embodiments, the treatment modality is one or more therapeutic agent. For example the treatment modality may comprise administering doxorubicin, cytarabine, vincristine, everolimus, alisertib, topotecan, etoposide, carboplatin, entinostat, panobinostat, romidepsin, palbociclib, abemaciclib, selumetinib, or trametinib, or a combination thereof. In another embodiment, the treatment modality is radiation therapy. For example the treatment modality may comprise exposure to X-ray irradiation.

In certain embodiments, the therapeutically effective amount of the second agent, is lowered due to the sensitizing effect of the EZH2 inhibitor. In some embodiments, the therapeutically effective amount of doxorubicin, cytarabine, vincristine, everolimus, alisertib, topotecan, etoposide, carboplatin, entinostat, panobinostat, romidepsin, palbociclib, abemaciclib, selumetinib, or trametinib, or a combination thereof, is lowered due to the sensitizing effect of the EZH2 inhibitor.

In certain embodiments, the therapeutically effective amount of radiation therapy is lowered due to the sensitizing effect of the EZH2 inhibitor. In some embodiments, the therapeutically effective amount of X-ray radiation is lowered due to the sensitizing effect of the EZH2 inhibitor.

In certain embodiments, the therapeutically effective amount of the EZH2 inhibitor is an amount sufficient to sensitize the subject to a treatment by administration of the one or more additional treatment modalities, e.g., simultaneously with, subsequent to, or prior to the administration of the EZH2 inhibitor. In certain embodiments, the therapeutically effective amount of the EZH2 inhibitor is an amount sufficient to sensitize the subject to a subsequent treatment by administration of the one or more additional treatment modalities. In certain embodiments, the amount of the one or more additional treatment modalities that is therapeutically effective is smaller than the amount of the same treatment modalities that is therapeutically effective in a subject not administered with the EZH2 inhibitor. In certain embodiments, the amount of the one or more additional treatment modalities that is therapeutically effective is smaller than the amount of the same treatment modalities that is therapeutically effective in a subject not sensitized with the EZH2 inhibitor, e.g., simultaneously with, subsequent to, or prior to the administration of the one or more additional treatment modalities.

In other aspects, the disclosure features a method of treating a malignant rhabdoid tumor (MRT), rhabdoid tumor of the kidney (RTK), atypical teratoid/rhabdoid tumor (AT/RT), epithelioid malignant peripheral nerve sheath tumor, myoepithelial carcinoma, and/or renal medullary carcinoma by administering to a subject in need thereof an EZH2 inhibitor in an amount sufficient to sensitize the subject to a treatment with one or more additional treatment modalities.

In some embodiments, sensitizing a subject includes inducing sensitivity to treatment with a standard of care treatment, or another agents, or a combination of agents in a subject having a cancer that is resistant or refractory to treatment with said standard of care treatment or another agents, or combination of agents. In some embodiments, sensitizing a subject includes increasing the efficacy of a standard of care treatment, or another agents, or a combination of agents. In some embodiments, sensitizing may be achieved by administering the standard of care treatment, other agents, or combination of agents in combination with an EZH2 inhibitor. For example sensitizing is achieved by administering an EZH2 inhibitor prior to the treatment with standard of care treatment, or another agents, or a combination of agents, or, sensitizing is achieved by administering an EZH2 inhibitor concurrently with the treatment with standard of care treatment, or another agents, or a combination of agents. In some embodiments, sensitizing a subject may include that a lower dose of a standard of care treatment, or another agents, or a combination of agents could be administered when used in combination with an EZH2 inhibitor. In some embodiments, sensitizing may include that inhibition of proliferation of diseased cells is increased. For example inhibition of proliferation is increased by 5%, 10% 15%, 20%, 25%, 30%, 50%, 75%, 90% or more as compared to the standard of care treatment, or treatment with agents, or treatment with a combination of agents without administration of an EZH2 inhibitor. In further embodiments, sensitizing may result in an improvement in the clinical response of a patient to the combination treatment, e.g., in a complete response (CR) in a patient who showed only partial response (PR), stable disease (SD), or progressive disease (PD), in response to standard of care treatment, or treatment with agents, or treatment with a combination of agents without administration of an EZH2 inhibitor. In further embodiments, sensitizing may result in an improvement in the clinical response of a patient to the combination treatment, e.g., in a complete response (CR) or a partial response (PR) in a patient who showed only stable disease (SD), or progressive disease (PD) in response to standard of care treatment, or treatment with agents, or treatment with a combination of agents without administration of an EZH2 inhibitor. In further embodiments sensitizing may result in an improvement in the clinical response of a patient to the combination treatment, e.g., in a complete response (CR), partial response (PR), or stable disease (SD), in a patient who showed progressive disease (PD) in response to standard of care treatment, or treatment with agents, or treatment with a combination of agents without administration of an EZH2 inhibitor. The terms complete response (CR), partial response (PR), stable disease (SD), and progressive disease (PD) are well known in the art (see, e.g., Eisenhauer et al. New response evaluation criteria in solid tumors: Revised RECIST guideline (version 1.1), EUROPEAN JOURNAL OF CANCER 45 (2009) 228-247, at page 232 and 233, section 4.3—"response criteria", the entire contents of which are incorporated herein by reference), and one or ordinary skill in the art will be aware of how to classify clinical responses according to these criteria.

In yet other aspects, the disclosure features a method of inhibiting or decreasing growth, viability, survival, or proliferation of a cancer cell comprising (1) contacting the cell with (a) an effective amount of EZH2 inhibitor, and (b) one or more second agents, or (2) contacting the cell with an effective amount of EZH2 inhibitor and exposing the cell to a radiation, wherein the cancer cell is an atypical teratoid rhabdoid tumor cell or a malignant rhabdoid tumor cell.

A "pharmaceutical composition" is a formulation containing a compound in a form suitable for administration to a subject. A compound disclosed herein and one or more other therapeutic agents described herein each can be formulated individually or in multiple pharmaceutical compositions in any combinations of the active ingredients. Accordingly, one or more administration routes can be properly elected based on the dosage form of each pharmaceutical composition. Alternatively, a compound disclosed herein and one or more other therapeutic agents described herein can be formulated as one pharmaceutical composition.

In some embodiments, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In some embodiments, the active compound is mixed under sterile conditions with a pharmaceutically acceptable carrier, and with any preservatives, buffers, or propellants that are required.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition disclosed herein is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A composition disclosed herein can be administered to a subject in many of the well-known methods currently used for chemotherapeutic treatment. For example, for treatment of cancers, a compound disclosed herein is injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

In certain embodiments the therapeutically effective amount of each pharmaceutical agent used in combination will be lower when used in combination in comparison to monotherapy with each agent alone. Such lower therapeutically effective amount could afford for lower toxicity of the therapeutic regimen.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity is determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

In some embodiments, the cancer treated with the combination of an EZH2 inhibitor and one or more second treatment modalities is advanced, refractory or resistant cancer, e.g., refractory or resistant to treatment with a standard-of-care treatment of with the one or more second treatment modalities in the absence of the EZH2 inhibitor.

In some embodiments, the cancer treated with the combination of an EZH2 inhibitor and one or more second treatment modalities cancer is an INI1-deficient tumor. INI1 is a critical component of the SWI/SNF regulatory complex, a chromatin remodeler that acts in opposition to EZH2. INI1-negative tumors have altered SWI/SNF function, resulting in aberrant and oncogenic EZH2 activity. This activity can be targeted by small molecule inhibitors of EZH2 such as tazemetostat. INI1-negative tumors are generally aggressive and are poorly served by current treatments. For example, current treatment of MRT, a well-studied INI1-negative tumor, consists of surgery, chemotherapy and radiation therapy, which are associated with limited efficacy and significant treatment-related morbidity.

In some embodiments, the subject is human.

In some embodiments, the cancer is characterized by aberrant H3-K27 methylation.

In some embodiments, the compound disclosed herein or a pharmaceutically acceptable salt thereof is administered orally for at least 7, 14, 21, 28, 35, 42, 47, 56, or 64 days.

In certain embodiments, the administration is a continuous administration without a drug holiday. For example, the compound disclosed herein or a pharmaceutically acceptable salt thereof is administered orally, for 28 days in a 28-day cycle. In other embodiments, the compound is administered with a drug holiday. For example, a compound disclosed herein or a pharmaceutically acceptable salt thereof is orally administered, e.g., for 21 days of a 28-day cycle with a 7-day drug holiday per cycle.

In some embodiments, said single dose ranges from about 100 mg to about 1600 mg.

In some embodiments, a single dose of a compound disclosed herein or a pharmaceutically acceptable salt thereof is 100, 200, 400, 800 or 1600 mg.

In some embodiments, said therapeutically effective amount is a single 800 mg dose, wherein said single dose provides a mean AUC(0-12) bioequivalent to a mean AUC (0-12) of from about 7798 ng*hr/ml to about 9441 ng*hr/ml.

In some embodiments, said therapeutically effective amount is a single 1600 mg dose, wherein said single dose provides a mean AUC(0-12) bioequivalent to a mean AUC (0-12) of from about 15596 ng*hr/ml to about 18882 ng*hr/ml.

In some embodiments, said therapeutically effective amount is a single 800 mg dose, wherein said single dose provides a mean $C_{max}$ bioequivalent to a mean $C_{max}$ of from about 1730 ng/ml to about 2063 ng/ml.

In some embodiments, said therapeutically effective amount is a single 1600 mg dose, wherein said single dose provides a mean $C_{max}$ bioequivalent to a mean $C_{max}$ of from about 3460 ng/ml to about 4125 ng/ml.

In some embodiments, said administering comprises administering orally a dosage form to the subject, twice per day or three times per day.

In some embodiments, said single dose provides a median $T_{max}$ of from about 1 hour to about 2 hours.

In some embodiments, said oral dosage form or formulation comprises an amount of therapeutic agent equivalent to about 25 mg to about 200 mg of EPZ-6438 per unit dose.

In some embodiments, said oral dosage form or formulation provides an dissolution rate of at least about 90%, or at least about 80%, or at least about 70% in dissolution medium (pH1.2, 37±0.5° C.) within 60 minutes from the onset of dissolution study using the Apparatus 2 (Paddle Apparatus, paddle speed; 50 rpm) according to the procedure for immediate-release dosage form in 6.10 Dissolution test of JP16 or <711> Dissolution of USP37.

In some embodiments, said oral dosage form or formulation provides an dissolution rate of at least about 90%, or at least about 80%, or at least about 70% in dissolution medium (pH1.2, 37±0.5° C.) within 45 minutes from the onset of dissolution study using the Apparatus 2 (Paddle Apparatus, paddle speed; 50 rpm) according to the procedure for immediate-release dosage form in 6.10 Dissolution test of JP16 or <711> Dissolution of USP37.

In some embodiments, said oral dosage form or formulation provides an dissolution rate of at least about 90%, or at least about 80%, or at least about 70% in dissolution medium (pH1.2, 37±0.5° C.) within 30 minutes from the onset of dissolution study using the Apparatus 2 (Paddle Apparatus, paddle speed; 50 rpm) according to the procedure for immediate-release dosage form in 6.10 Dissolution test of JP16 or <711> Dissolution of USP37.

In some embodiments, said oral dosage form or formulation provides an dissolution rate of at least about 80%, or at least about 75%, or at least about 70%, or at least about 60% in dissolution medium (pH4.5 acetate buffer, 37±0.5° C.) within 60 minutes from the onset of dissolution study using the Apparatus 2 (Paddle Apparatus, paddle speed; 50 rpm) according to the procedure for immediate-release dosage form in 6.10 Dissolution test of JP16 or <711> Dissolution of USP37.

In some embodiments, said oral dosage form or formulation comprises sodium starch glycolate or carmellose or a combination thereof as pharmaceutically acceptable carrier or excipient.

Other compounds suitable for the methods of the disclosure are described in U.S. Publication 20120264734, the contents of which are hereby incorporated by reference in their entireties. Further, Compound (A) is suitable for administration as part of a combination therapy with one or more other therapeutic agents or treatment modality, suitable to be administered together, sequentially, or in alternation.

In some embodiments, Compound (A) or a pharmaceutically acceptable salt thereof is administered to the subject at a dose of approximately 100 mg to approximately 3200 mg daily, such as about 100 mg BID to about 1600 mg BID (e.g., 100 mg BID, 200 mg BID, 400 mg BID, 800 mg BID, or 1600 mg BID), for treating INI1-negative tumor (e.g., rhabdoid tumor of the kidney (RTK), atypical teratoid/rhabdoid tumor (ATRT), epithelioid malignant peripheral nerve sheath tumor, myoepithelial carcinoma, and renal medullary carcinoma).

The use of the articles "a", "an", and "the" herein are to be construed to cover both the singular and the plural, unless otherwise indicated herein or clearly contradicted by context. For example, the term "a disintegrant" refers to one or more disintegrants included in or suitable for use in the formulation described herein. Similarly, the term "a therapeutic agent" refers to one or more therapeutic agents included in or suitable for use in the formulation described herein. For example, the formulation described herein can include Compound (A) alone as the therapeutic agent or active ingredient or include a mixture of Compound (A) and another compound (e.g., HBr salt of Compound (A) or another anti-cancer drug). The terms "comprising", "having", "including", and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of."

The concentration of the therapeutic agent in the formulation is expressed as equivalent to a certain amount of Compound (A). As used herein, the term "equivalent" amount or weight percentage refers to the quantity of the drug substance that is adjusted as per potency adjustment factor, a value derived for the assay value obtained from Compound (A). Methods for determining the equivalent amount are well known in the art (see, e.g., http://www.fda.gov/downloads/Drugs/ . . . /Guidances/ucm070246.pdf).

The term "about", "approximately", or "approximate", when used in connection with a numerical value, means that a collection or ranger of values is included. For example, "about X" includes a range of values that are ±10%, ±5%, ±2%, ±1%, ±0.5%, ±0.2%, or ±0.1% of X, where X is a numerical value. In addition, "about X" may also include a range of X±0.5, X±0.4, X±0.3, X±0.2, or X±0.1, where X is a numerical value. In some embodiments, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present disclosure. Furthermore, so-called metabolite which is produced by degradation of the present compound in vivo is included in the scope of the present disclosure.

Furthermore, the structures and other compounds discussed in this disclosure include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The term "crystal polymorphs", "polymorphs" or "crystalline forms" means crystal structures in which a compound (or a salt or solvate thereof) can crystallize in different crystal packing arrangements, all of which have the same elemental composition. Different crystal forms usually have different XRPD patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Compounds of the disclosure may be crystalline, semi-crystalline, non-crystalline, amorphous, mesomorphous, etc.

Additionally, the compounds or crystalline forms of the present disclosure, for example, the salts of the compounds or crystalline forms, can exist in either hydrated or unhydrated (the anhydrous) form or as solvates with other solvent molecules. Nonlimiting examples of hydrates include hemihydrates, monohydrates, dihydrates, trihydrates, etc. Nonlimiting examples of solvates include ethanol solvates, acetone solvates, etc.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hemihydrate is formed by the combination of one molecule of water with more than one molecule of the substance in which the water retains its molecular state as $H_2O$.

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

As used herein, a "subject" is interchangeable with a "subject in need thereof", both of which refer to a subject having a disorder in which EZH2-mediated protein methylation plays a part, or a subject having an increased risk of developing such disorder relative to the population at large. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In some embodiments, the mammal is a human. A subject in need thereof can be one who has been previously diagnosed or identified as having cancer or a precancerous condition. A subject in need thereof can also be one who has (e.g., is suffering from) cancer or a precancerous condition. Alternatively, a subject in need thereof can be one who has an increased risk of developing such disorder relative to the population at large (i.e., a subject who is predisposed to developing such disorder relative to the population at large). A subject in need thereof can have a precancerous condition. A subject in need thereof has an INI1-negative tumor.

INI1 is a regulatory complex that opposes the enzymatic function of EZH2. Due to a variety of genetic alterations, INI1 loses its regulatory function. As a result, EZH2 activity is misregulated, causing EZH2 to play a driving, oncogenic role in a set of genetically defined cancers that include rhabdoid tumor of the kidney (RTK), atypical teratoid/rhabdoid tumor (ATRT), epithelioid malignant peripheral nerve sheath tumor, myoepithelial carcinoma, and renal medullary carcinoma.

A subject in need thereof can have refractory or resistant cancer (i.e., cancer that doesn't respond or hasn't yet responded to treatment). The subject may be resistant at start of treatment or may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In a preferred embodiment, the subject has cancer or a cancerous condition.

In certain embodiments, in any method described herein, the subject is an adult patient aged 18 years or older.

In certain embodiments, in any method described herein, the subject is a pediatric patient aged 12 months or younger (e.g., between 3 and 12 months old).

In certain embodiments, in any method described herein, the subject is a subject older than 12 months but younger than 18 years old.

In any method described herein, the subject can be a pediatric (non-adult) patient aged 3 months to 18 years.

As used herein, "treating" or "treat" describes the management and care of a patient for the purpose of combating a disease, condition, or disorder and includes the administration of a compound of the present disclosure, or a pharmaceutically acceptable salt, prodrug, metabolite, polymorph or solvate thereof, to alleviate the symptoms or complications of a disease, condition or disorder, or to eliminate the disease, condition or disorder. The term "treat" can also include treatment of a cell in vitro or an animal model.

A compound of the present disclosure, or a pharmaceutically acceptable salt, prodrug, metabolite, polymorph or solvate thereof, can or may also be used to prevent a relevant disease, condition or disorder, or used to identify suitable candidates for such purposes. As used herein, "preventing," "prevent," or "protecting against" describes reducing or eliminating the onset of the symptoms or complications of such disease, condition or disorder.

The methods and uses described herein may include steps of detecting the presence or absence of one or more EZH2 mutations in a sample from a subject in need thereof prior to and/or after the administration of a compound or composition described herein to the subject. By "sample" it means any biological sample derived from the subject, includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively samples can be obtained by the physician according to routine practice in the art.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, New York (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using aspects of the disclosure.

The present disclosure also provides pharmaceutical compositions comprising one or more active compounds (e.g., Compound (A) or a salt thereof) in combination with at least one pharmaceutically acceptable excipient or carrier.

In some embodiments, the pharmaceutical composition is in bulk or in unit dosage form. The term "unit dosage form" as used herein refers to physically discrete units suited as unitary dosages for the subject to be treated; each unit containing a predetermined quantity of active compound calculated to produce the desired therapeutic effect in association with the required pharmaceutical carrier. The unit dosage form is any of a variety of forms, including, for example, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In some embodiments, the active compound is mixed under sterile conditions with a pharmaceutically acceptable carrier, and with any preservatives, buffers, or propellants that are required.

In some embodiments, the unit dosage form is an oral dosage form. In some embodiments, the unit dosage form is a tablet. In some embodiments, the unit dosage form is an oral suspension. In some embodiments, the unit dosage form is an oral suspension and the subject is a pediatric subject.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient. For example, a pharmaceutically acceptable excipient used for the formulation of the disclosure can be a diluent or inert carrier, a lubricant, a binder, or a combination thereof. The pharmaceutically acceptable excipient used for the formulation of the disclosure can further include a filler, an anti-microbial agent, an antioxidant, an anti-caking agent, a coating agent, or a mixture thereof.

Examples of pharmaceutically acceptable excipients include, but are not limited to binders, fillers, disintegrants, lubricants, anti-microbial agents, antioxidant, and coating agents.

Exemplary binders include, but are not limited to corn starch, potato starch, other starches, gelatin, natural and synthetic gums such as acacia, xanthan, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone (e.g., povidone, crospovidone, copovidone, etc.), methyl cellulose, Methocel, pre-gelatinized starch (e.g., STARCH 1500® and STARCH 1500 LM®, sold by Colorcon, Ltd.), hydroxypropyl cellulose, hydroxypropyl methyl cellulose, microcrystalline cellulose (FMC Corporation, Marcus Hook, Pa., USA), Emdex, Plasdone, or mixtures thereof, FILLERS: talc, calcium carbonate (e.g., granules or powder), dibasic calcium phosphate, tribasic calcium phosphate, calcium sulfate (e.g., granules or powder), microcrystalline cellulose, powdered cellulose, dextrates, kaolin, mannitol, silicic acid, sorbitol, starch, pre-gelatinized starch, dextrose, fructose, honey, lactose anhydrate, lactose monohydrate, lactose and aspartame, lactose and cellulose, lactose and microcrystalline cellulose, maltodextrin, maltose, mannitol, microcrystalline cellulose & guar gum, molasses, sucrose, or mixtures thereof.

Exemplary disintegrants include, but are not limited to: agar-agar, alginic acid, calcium carbonate, microcrystalline cellulose, croscarmellose sodium, crospovidone, polacrilin potassium, sodium starch glycolate (such as Explotab), potato or tapioca starch, other starches, pre-gelatinized starch, clays, other algins, other celluloses, gums (like gellan), low-substituted hydroxypropyl cellulose, ploypl-asdone, or mixtures thereof.

Exemplary lubricants include, but are not limited to: calcium stearate, magnesium stearate, mineral oil, light mineral oil, glycerin, sorbitol, mannitol, polyethylene glycol, other glycols, compritol, stearic acid, sodium lauryl sulfate, sodium stearyl fumarate (such as Pruv), vegetable based fatty acids lubricant, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Degussa Corp., Plano, Tex. USA), a pyrogenic silicon dioxide (CAB-O-SIL, Cabot Co., Boston, Mass. USA), or mixtures thereof.

Exemplary anti-caking agents include, but are not limited to: calcium silicate, magnesium silicate, silicon dioxide, colloidal silicon dioxide, talc, or mixtures thereof.

Exemplary antimicrobial agents include, but are not limited to: benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, or mixtures thereof.

Exemplary antioxidants include, but are not limited to: ascorbic acid, BHA, BHT, EDTA, or mixture thereof.

Exemplary coating agents include, but are not limited to: sodium carboxymethyl cellulose, cellulose acetate phthalate, ethylcellulose, gelatin, pharmaceutical glaze, hydroxypropyl cellulose, hydroxypropyl methylcellulose (hypromellose), hydroxypropyl methyl cellulose phthalate, methylcellulose, polyethylene glycol, polyvinyl acetate phthalate, shellac, sucrose, titanium dioxide, carnauba wax, microcrystalline wax, gellan gum, maltodextrin, methacrylates, microcrystalline cellulose and carrageenan or mixtures thereof.

The formulation described herein can also include other excipients and categories thereof including but not limited to Pluronic®, Poloxamers (such as Lutrol® and Poloxamer 188), ascorbic acid, glutathione, protease inhibitors (e.g. soybean trypsin inhibitor, organic acids), pH lowering agents, creams and lotions (like maltodextrin and carrageenans); materials for chewable tablets (like dextrose, fructose, lactose monohydrate, lactose and aspartame, lactose and cellulose, maltodextrin, maltose, mannitol, microcrystalline cellulose and guar gum, sorbitol crystalline); parenterals (like mannitol and povidone); plasticizers (like dibutyl sebacate, plasticizers for coatings, polyvinylacetate phthalate); powder lubricants (like glyceryl behenate); spheres for coating (like sugar spheres); spheronization agents (like glyceryl behenate and microcrystalline cellulose); suspending/gelling agents (like carrageenan, gellan gum, mannitol, microcrystalline cellulose, povidone, sodium starch glycolate, xanthan gum); sweeteners (like aspartame, aspartame and lactose, dextrose, fructose, honey, maltodextrin, maltose, mannitol, molasses, sorbitol crystalline, sorbitol special solution, sucrose); wet granulation agents (like calcium carbonate, lactose anhydrous, lactose monohydrate, maltodextrin, mannitol, microcrystalline cellulose, povidone, starch), caramel, carboxymethylcellulose sodium, cherry cream flavor and cherry flavor, citric acid anhydrous, citric acid, confectioner's sugar, D&C Red No. 33, D&C Yellow #10 Aluminum Lake, disodium edetate, ethyl alcohol 15%, FD&C Yellow No. 6 aluminum lake, FD&C Blue #1 Aluminum Lake, FD&C Blue No. 1, FD&C blue no. 2 aluminum lake, FD&C Green No. 3, FD&C Red No. 40, FD&C Yellow No. 6 Aluminum Lake, FD&C Yellow No. 6, FD&C Yellow No. 10, glycerol palmitostearate, glyceryl monostearate, indigo carmine, lecithin, mannitol, methyl and propyl parabens, mono ammonium glycyrrhizinate, natural and artificial orange flavor, pharmaceutical glaze, poloxamer 188, Polydextrose, polysorbate 20, polysorbate 80, polyvidone, pregelatinized corn starch, pregelatinized starch, red iron oxide, saccharin sodium, sodium carboxymethyl ether, sodium chloride, sodium citrate, sodium phosphate, strawberry flavor, synthetic black iron oxide, synthetic red iron oxide, titanium dioxide, and white wax.

In certain embodiments, the formulation of the disclosure is a solid oral dosage form that may optionally be treated with coating systems (e.g. Opadry® fx film coating system) to be coated with for example Opadry® blue (OY-LS-20921), Opadry® white (YS-2-7063), Opadry® white (YS-1-7040), and black ink (S-1-8 106).

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician.

The pharmaceutical compositions of the present disclosure containing active compounds may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms disclosed herein are dictated by and directly dependent on the unique characteristics of the active compound and the particular therapeutic effect to be achieved.

In therapeutic applications, the dosages of the EZH2 inhibitor compounds described herein, or the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In some aspects, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active Compound (A) and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds in the formulation of the present disclosure are capable of further forming salts. All of these forms are also contemplated within the scope of the claimed disclosure.

As used herein, "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In some embodiments, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound disclosed herein, or a pharmaceutically acceptable salt, solvate, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound disclosed herein, or a pharmaceutically acceptable salt, solvate, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleomorphism.

As used herein, the term "selectively" means tending to occur at a higher frequency in one population than in another population. The compared populations can be cell populations. Preferably, a compound disclosed herein, or a pharmaceutically acceptable salt or solvate thereof, acts selectively on a cancer or precancerous cell but not on a normal cell. Preferably, a compound disclosed herein, or a pharmaceutically acceptable salt or solvate thereof, acts selectively to modulate one molecular target (e.g., a target protein methyltransferase) but does not significantly modulate another molecular target (e.g., a non-target protein methyltransferase). The disclosure also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A composition disclosed herein does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound disclosed herein, or a pharmaceutically acceptable salt or solvate thereof, demonstrates a minimum of a fourfold differential, preferably a tenfold differential, more preferably a fifty fold differential, in the dosage required to achieve a biological effect. Preferably, a compound disclosed herein, or a pharmaceutically acceptable salt or solvate thereof, demonstrates this differential across the range of inhibition, and the differential is exemplified at the $IC_{50}$, i.e., a 50% inhibition, for a molecular target of interest.

Administering a composition disclosed herein to a cell or a subject in need thereof can result in modulation (i.e., stimulation or inhibition) of an activity of a protein methyltransferase of interest.

Administering a compound disclosed herein, e.g., a composition comprising any compound disclosed herein or pharmaceutically acceptable salt thereof, and one or more other therapeutic agents, such as prednisone, to a cell or a subject in need thereof results in modulation (i.e., stimulation or inhibition) of an activity of an intracellular target (e.g., substrate). Several intracellular targets can be modulated with the compounds disclosed herein, including, but not limited to, protein methyltransferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., Proc Natl Acad Sci USA. 100(5): 2674-8, 2003. In some aspects, cell death occurs by apoptosis.

Preferably, an effective amount of a composition disclosed herein, or a pharmaceutically acceptable salt or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In some aspects, cell death occurs by apoptosis.

Contacting a cell with a composition disclosed herein, or a pharmaceutically acceptable salt or solvate thereof, can induce or activate cell death selectively in cancer cells. Administering to a subject in need thereof a compound disclosed herein, or a pharmaceutically acceptable salt or solvate thereof, can induce or activate cell death selectively in cancer cells. Contacting a cell with a composition disclosed herein, or a pharmaceutically acceptable salt or solvate thereof, can induce cell death selectively in one or more cells affected by a cell proliferative disorder. Preferably, administering to a subject in need thereof a composition disclosed herein, or a pharmaceutically acceptable salt or solvate thereof, induces cell death selectively in one or more cells affected by a cell proliferative disorder.

The present disclosure relates to a method of treating or preventing cancer by administering a composition disclosed herein, or a pharmaceutically acceptable salt or solvate thereof, to a subject in need thereof, where administration of the composition disclosed herein, or a pharmaceutically acceptable salt or solvate thereof, results in one or more of the following: prevention of cancer cell proliferation by accumulation of cells in one or more phases of the cell cycle (e.g. G1, G1/S, G2/M), or induction of cell senescence, or promotion of tumor cell differentiation; promotion of cell death in cancer cells via cytotoxicity, necrosis or apoptosis, without a significant amount of cell death in normal cells, antitumor activity in animals with a therapeutic index of at least 2. As used herein, "therapeutic index" is the maximum tolerated dose divided by the efficacious dose.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

Unless specifically stated or obvious from context, as used herein, the term "or" is understood to be inclusive.

Unless otherwise clear from the context, all numerical values provided herein are modified by the term "about."

Malignant Rhabdoid Tumors (MRT) and Atypical Teratoid Rhabdoid Tumors

Malignant Rhabdoid Tumors (MRT) and Atypical Teratoid Rhabdoid Tumors (AT/RT) are typically pediatric cancers which are rare and aggressive with extremely high unmet medical need. At a molecular level MRT and AT/RT tumors are almost universally characterized by loss of the INI1 protein (also known as SNF5 or SMARCB1), a component of the Switch Sucrose Non-fermentable (SWI/SNF) multimeric chromatin modifying complex. In many cell types, the SWI/SNF complex and the PRC2 complex have an antagonistic relationship in the regulation of tumor suppressor genes, cell cycle checkpoints, hedgehog and myc pathway genes, among others (see Wilson et al. *Cancer Cell*. 2010, 18, 316-28; incorporated herein by reference in its entirety). This explicated the possibility of a novel treatment modality for these tumors, based on inhibition of EZH2—the catalytic subunit of PRC2.

Tazemetostat (EPZ-6438) is a potent and orally bioavailable small molecule inhibitor of EZH2 currently in phase 2 clinical trials in adult patients with non-Hodgkin lymphoma, INI1-negative tumors and mesothelioma. Dependency of IND-negative tumors on EZH2 catalytic activity was demonstrated in preclinical models of MRT, where robust tumor regressions were induced with tazemetostat treatment (see Knutson et al. *Proc Natl Acad Sci* 2013, 110, 7922-7; incorporated herein by reference in its entirety). Consistent with this, tazemetostat demonstrated activity in relapsed or refractory patients with IND-negative tumors enrolled in the adult phase 1 clinical trial. Furthermore in phase 2 clinical trials in adult patients with non-Hodgkin lymphoma, INI1-negative tumors and mesothelioma and in phase 1 clinical trials in pediatric patients with INI1 negative tumors, tazemetostat elicited strong antiproliferative response in AT/RT cell lines characterized by loss of INI-1 protein.

Therapies for MRT and AT/RT are comprised of cytotoxic chemotherapy which may or may not be administered in the context of stem cell transplant, in addition to surgical resection and radiation therapy. In support of combination clinical scenarios including EZH2 inhibition in this setting, we sought to explore the antiproliferative effects of combining tazemetostat with current small molecule treatment therapies in cell line models of AT/RT and MRT. Synergistic activity was observed when tazemetostat was combined with individual components of chemotherapeutic regimens and targeted therapies such as vincristine, doxorubicin, alisertib and HDAC inhibitors. For example, in vitro studies performed using a panel of AT/RT and MRT cell lines to understand the effect of tazemetostat in combination chemotherapy uncovered synergistic interactions with doxorubicin, topotecan and vincristine. EZH2 inhibition also enhanced the antiproliferative effect of emerging targeted therapies such as alisertib, entinostat and RAS pathway inhibitors Further, the effects of ionizing radiation together with tazemetostat treatment were investigated. Application of X-ray irradiation concomitantly or after tazemetostat treatment, induced robust antiproliferative activity and reduction in clonogenic potential of both AT/RT cell lines. For example, priming AT/RT cell lines with tazemetostat for seven days prior to X-ray irradiation resulted in a dramatic decrease in cell proliferation and clonogenic potential compared to the effect of the single agents.

Taken together these results suggested that pharmacological inhibition of EZH2 enhances the activity of other therapies and may have advantage over monotherapy in INI1-negative cancers supporting the therapeutic potential and potential to extend the utility of current treatment of combination regimens that include tazemetostat in these tumors.

EXAMPLES

Example 1

INI1 is a critical component of the SWI/SNF regulatory complex, a chromatin remodeler that acts in opposition to EZH2. INI1-negative tumors have altered SWI/SNF function, resulting in aberrant and oncogenic EZH2 activity. This activity can be targeted by small molecule inhibitors of EZH2 such as tazemetostat. INI1-negative tumors are generally aggressive and are poorly served by current treatments. For example, current treatment of MRT, a well-studied INI1-negative tumor, consists of surgery, chemotherapy and radiation therapy, which are associated with limited efficacy and significant treatment-related morbidity.

The adult phase 2 multicenter study will enroll up to 90 patients in three cohorts. The first cohort will be comprised of patients with malignant rhabdoid tumor (MRT), rhabdoid tumor of the kidney (RTK) and atypical teratoid/rhabdoid tumor (ATRT). The second cohort will be comprised of patients with other INI1-negative tumors including epithelioid sarcoma, epithelioid malignant peripheral nerve sheath tumor, extraskeletal myxoid chondrosarcoma, myoepithelial carcinoma, and renal medullary carcinoma. The third cohort will be comprised of patients with synovial sarcoma. Dosing in all three cohorts will be at the recommended phase 2 dose of 800 mg twice per day (BID) with a tablet formulation. The primary endpoint is overall response rate (ORR) for patients with INI1-negative tumors and progression-free survival (PFS) for patients with synovial sarcoma. Secondary endpoints include duration of response, overall survival (OS), PFS for patients with INI1-negative tumors, safety and pharmacokinetics (PK).

The pediatric phase 1 multicenter study will enroll approximately 40 patients in a dose escalation design, followed by dose expansion, with an oral suspension of tazemetostat. The study will enroll subjects with INI1-negative tumors or synovial sarcoma. INI1-negative tumors include MRT, ATRT, RTK, and other INI1-negative tumors as previously described. The primary endpoint of study is safety with the objective of establishing the recommended phase 2 dose in pediatric patients. Secondary endpoints include PK, ORR, duration of response, PFS and OS.

Example 2

Figure 4A:
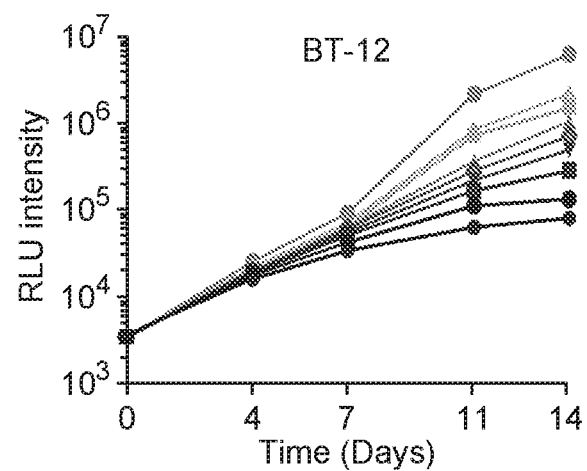
FIGS. 4A and 4B are a pair of graphs illustrating time and dose dependent antiproliferative activity of tazemetostat in (FIG. 4A) BT-12 cells and (FIG. 4B) CHLA-266 cells. Cell viability was measured in a luminescent cell viability assay and is represented by luminescence counts.
Figure 4B:
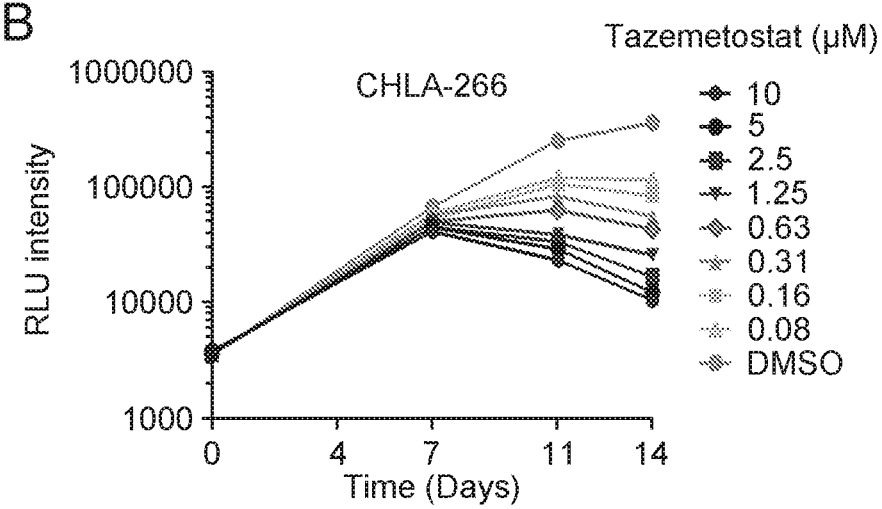
Figure 5C:
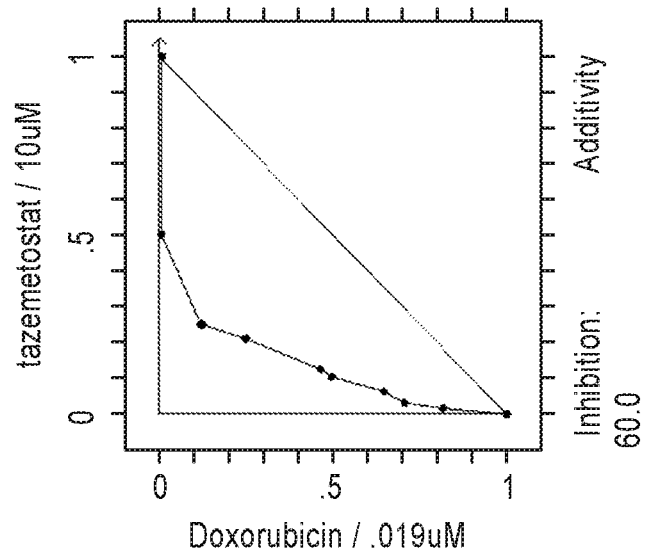
Figure 5D:
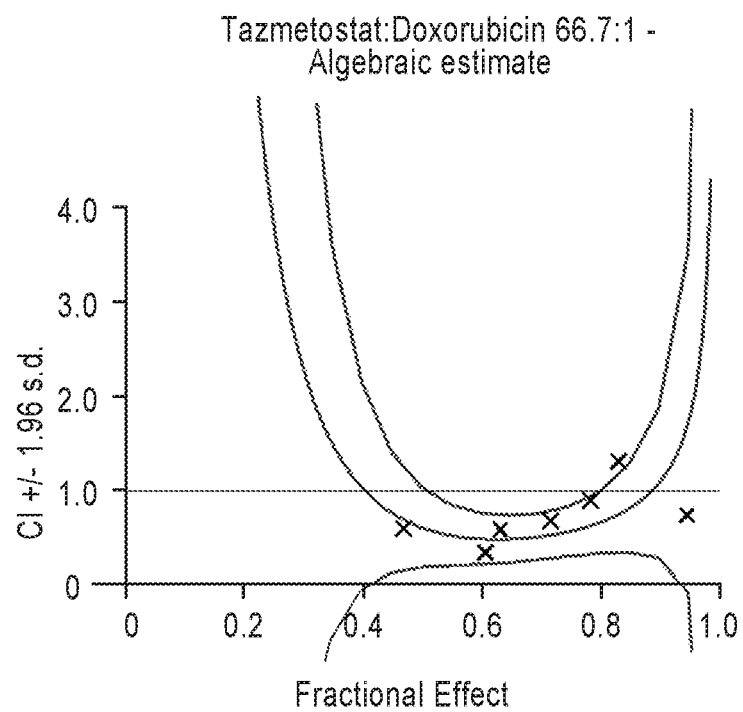
Figure 6A:
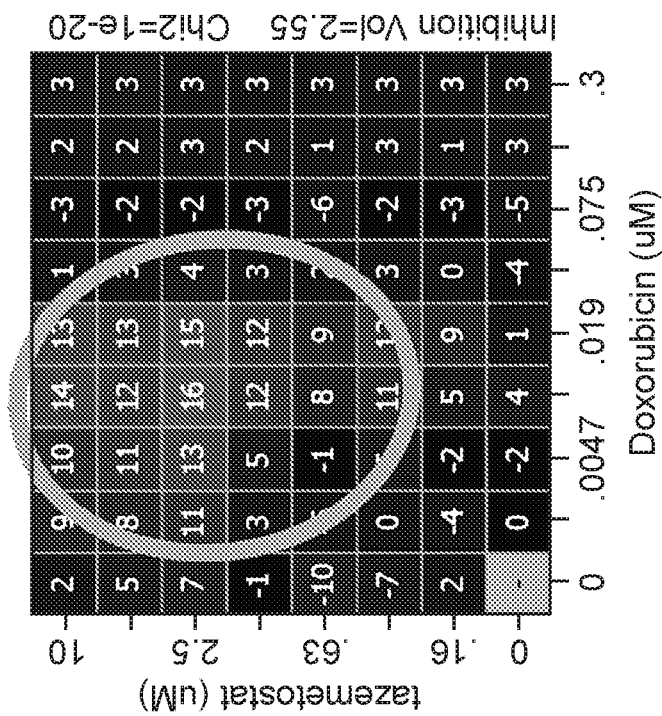
FIGS. 6A-6D are a set of graphs illustrating synergy of doxorubicin with tazemetostat in CHLA-266 cells grown in the pretreatment model described in Example 3.
Figure 6B:
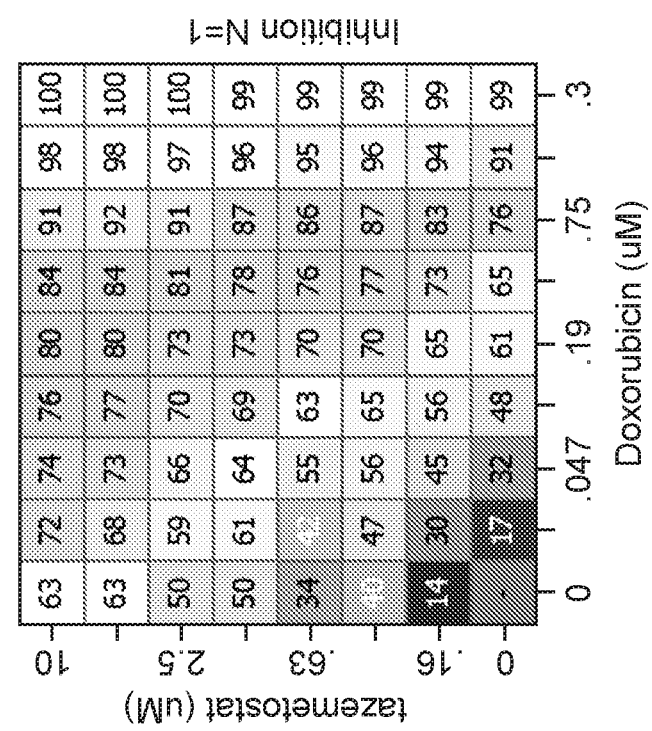
Figure 6C:
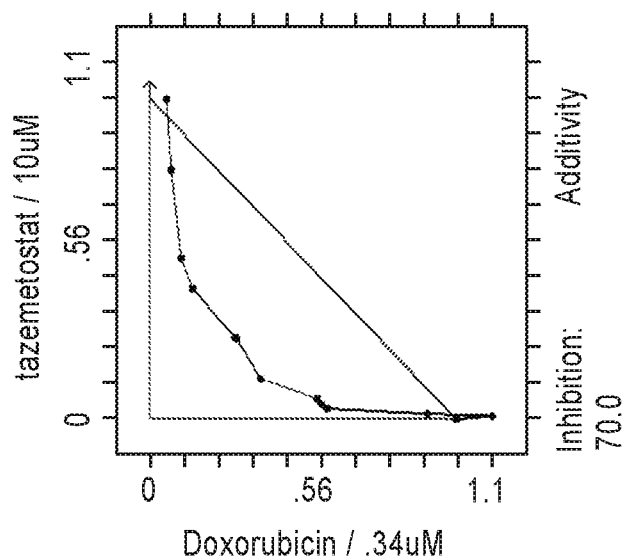
Figure 6D:
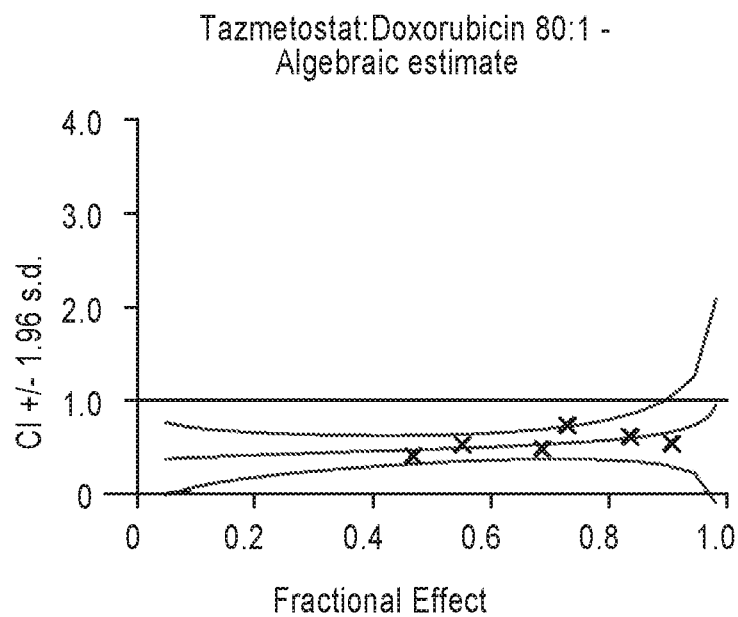
Figure 7A:
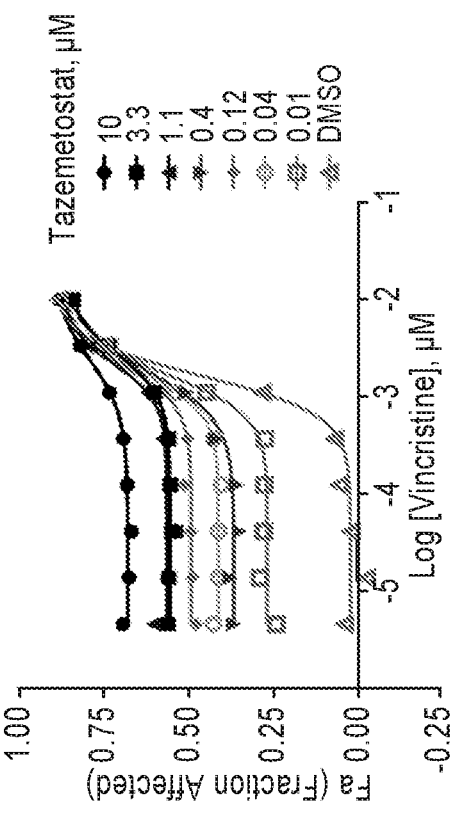
FIGS. 7A-7D are a series of graphs illustrating synergy of tazemetostat with additional agents in BT-12 cells. The graphs depict the effect (fa) as a function of concentration of (FIG. 7A) doxorubicin, (FIG. 7B) vincristine, (FIG. 7C) alisertib and (FIG. 7D) entinostat at various concentrations of tazemetostat as indicated in the graphs. The concentrations of the additional agents are represented on a logarithmic scale.
Figure 7B:
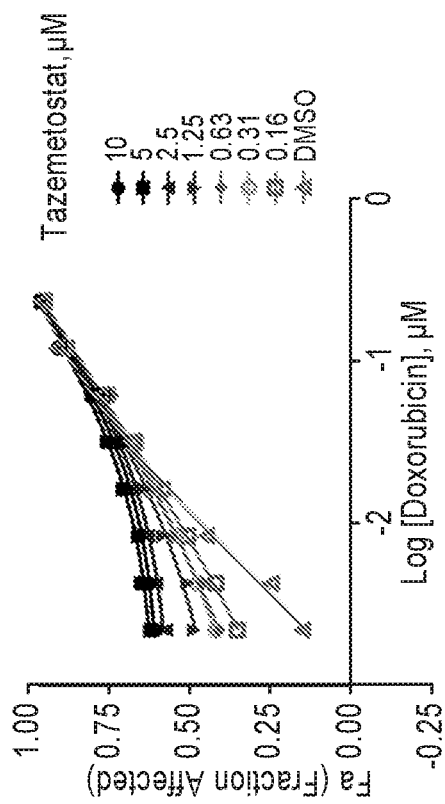
Figure 7C:
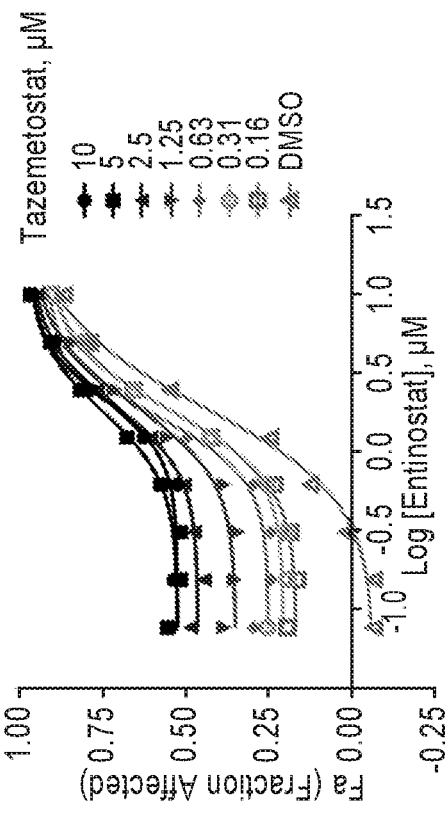
Figure 7D:
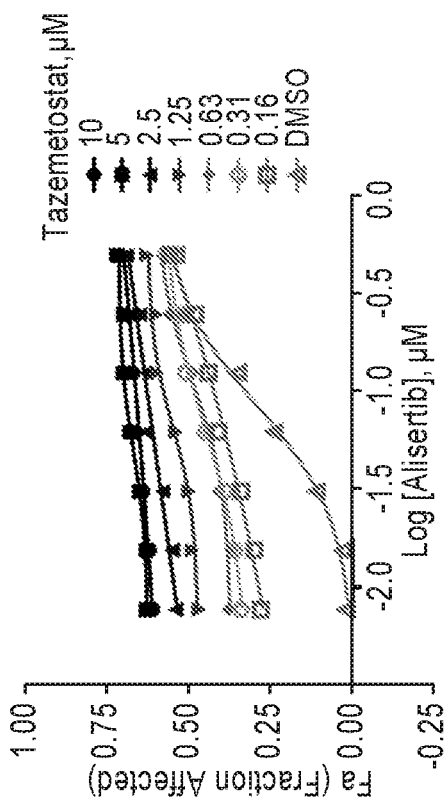
Figure 8A:
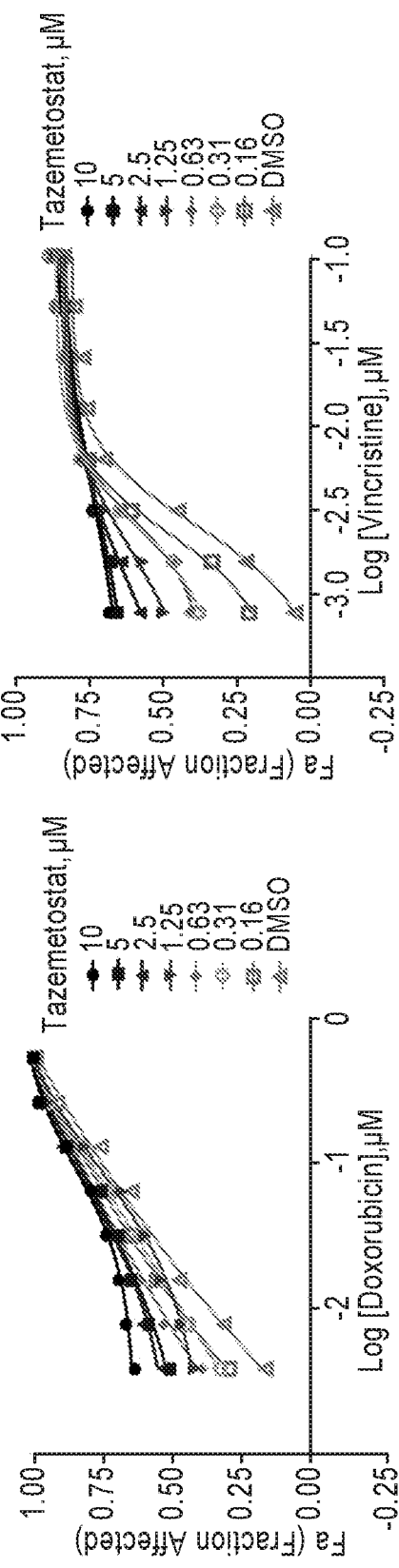
FIGS. 8A-8D are a series of graphs illustrating synergy of tazemetostat with additional agents in CHLA-266 cells. The graphs depict the effect (fa) as a function of concentration of (FIG. 8A) doxorubicin, (FIG. 8B) vincristine, (FIG. 8C) alisertib and (FIG. 8D) entinostat at various concentrations of tazemetostat as indicated in the graphs. The concentrations of the additional agents are represented on a logarithmic scale.
Figure 8B:
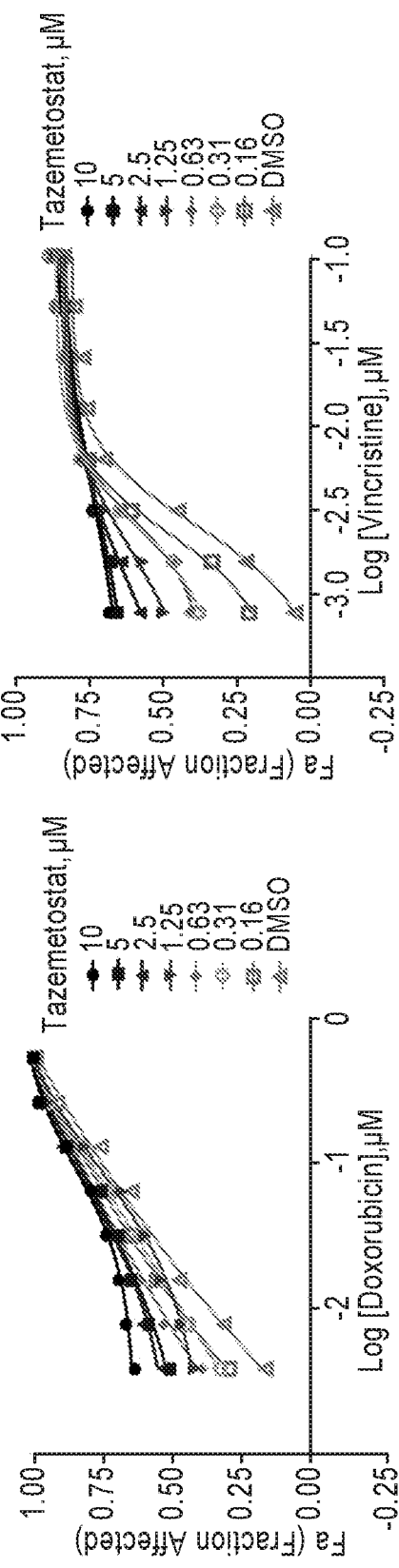
Figure 8D:
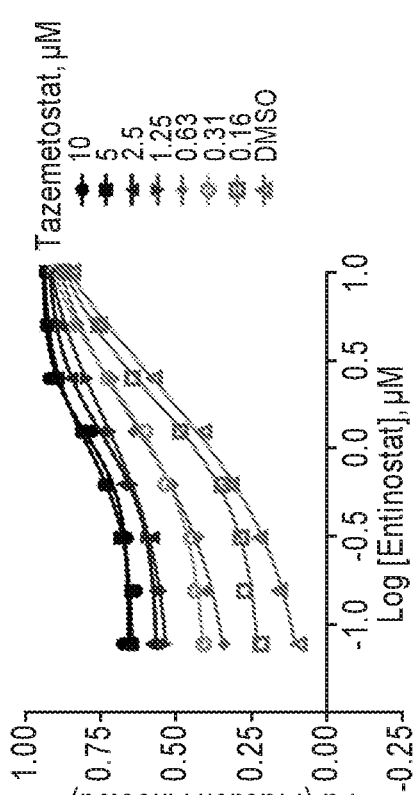
Figure 8C:
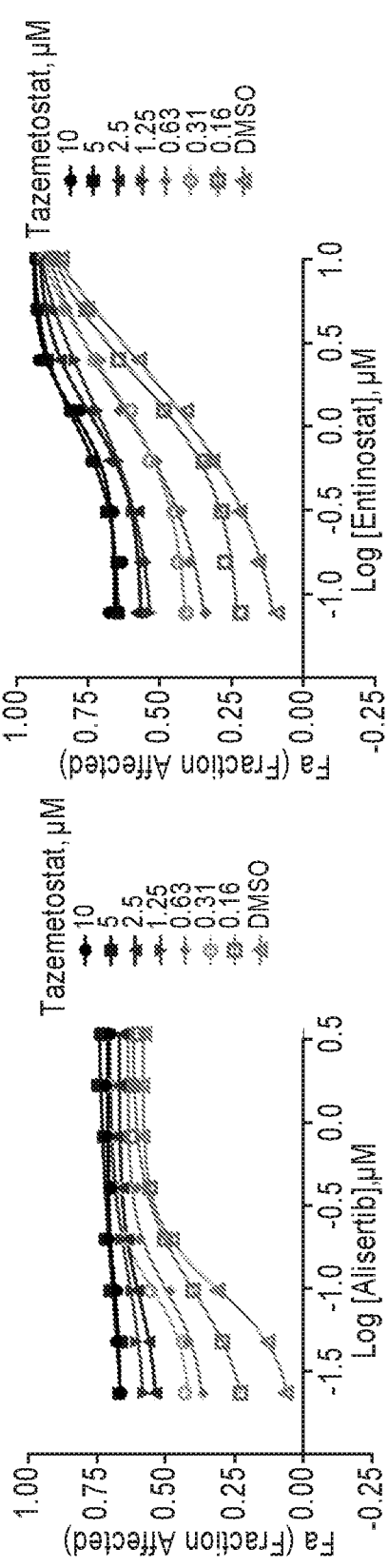
Figure 9A:
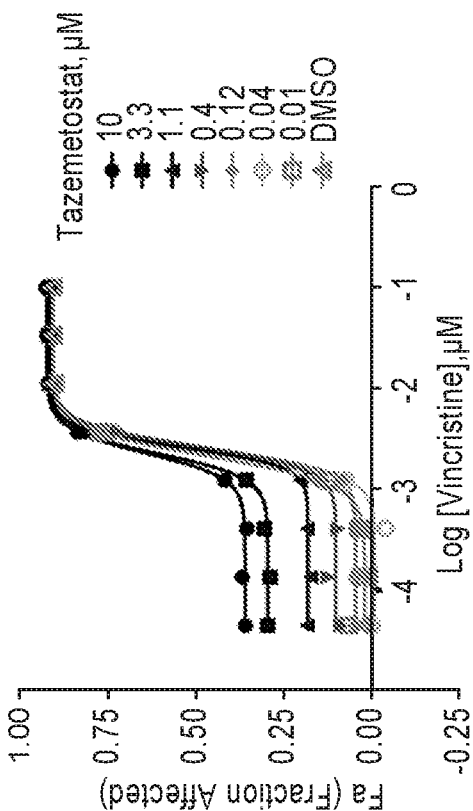
FIGS. 9A-9D are a series of graphs illustrating synergy of tazemetostat with additional agents in A204 cells. The graphs depict the effect (fa) as a function of concentration of (FIG. 9A) doxorubicin, (FIG. 9B) vincristine, (FIG. 9C) alisertib and (FIG. 9D) entinostat at various concentrations of tazemetostat as indicated in the graphs. The concentrations of the additional agents are represented on a logarithmic scale.
Figure 9B:
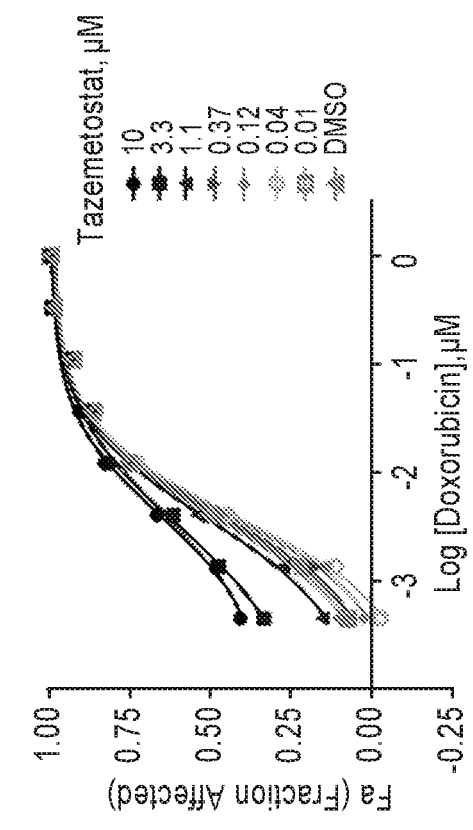
Figure 9C:
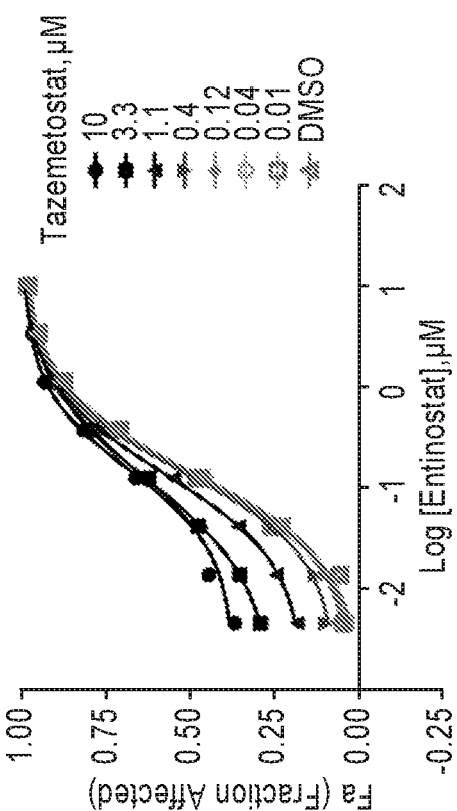
Figure 9D:
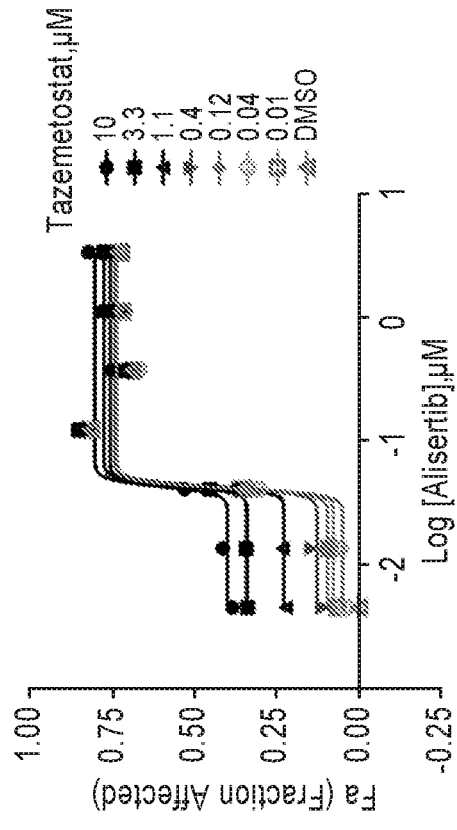

Antiproliferative Activity of Tazemetostat in Atypical Teratoid Rhabdoid Tumor Cell Lines Two atypical teratoid rhabdoid tumor cell lines were grown in 2D culture and incubated with either DMSO or tazemetostat at concentrations of 0.08, 0.16, 0.31, 0.63, 1.25, 2.5, 5, and 10 μM. Cell viability was assessed by measuring cellular adenosine triphosphate (ATP) in a luminescent cell viability assay on days 4, 6, 7, 11, and 15 and cells were split and replated at the original seeding density on day 7. The results are summarized in FIG. 4. Time and dose dependent increases in cell death were observed. Long term proliferation $IC_{50}$ values for malignant rhabdoid tumor (MRT) cell lines were previously determined as 135 nM and 1000 nM for G401 and A204 cell lines, respectively (see Knutson et al, *Proc Natl Acad Sci.* 2013, 110, 7922-7; incorporated herein by reference in its entirety).

Example 3

Combination Studies of Tazemetostat with Other Agents

Pretreatment Model: Two atypical teratoid rhabdoid tumor (AT/RT) cell lines, BT-12 and CHLA-266 were grown in individual flasks with increasing concentrations of tazemetostat for four days. Cells were then washed and plated to 96 well plates containing standard agents alone, and in combination with tazemetostat, and grown for an additional four days. Quantification of proliferation through measurement of cellular adenosine triphosphate (ATP) was performed in a luminescent cell viability assay. Proliferation data was read for luminescence. Calculations of synergy were performed using the Loewe Volume (Chalice Software) and Fa-CI plots were generated with Calcusyn.

Co-treatment Model: Two malignant rhabdoid tumor (MRT) cell lines, A-204 and G401 were directly plated to 96 well plates containing standard agents alone, and in combination with tazemetostat, and grown for seven days. Quantification of proliferation through measurement of cellular adenosine triphosphate (ATP) was performed in a luminescent cell viability assay. Proliferation data was read for luminescence.

The results of the combination study of tazemetostat with other therapies in the pretreatment and co-treatment models described above are summarized in Table 1 and FIGS. 5-10.

TABLE 1

Combination treatment with tazemetostat in AT/RT cell lines

| Compound | Target Class/Mechanism | BT-12 | CHLA-266 | G401 | A204 |
|---|---|---|---|---|---|
| Doxorubicin | DNA intercalation | Synergy | Synergy | Additive | Additive |
| Cytarabine/Ara-C | DNA damaging | Synergy | Additive | Additive | Additive |
| Vincristine | Microtubule depolymerization inhibition | Synergy | Synergy | Synergy at higher fa | Synergy |
| Everolimus | mTOR inhibitor | Synergy | Synergy | Additive | Additive |
| Alisertib | Aurora A Kinase inhibitor | Synergy | Synergy | Additive | Additive |
| Topotecan | Topoisomerase inhibitor | Synergy | Synergy | Synergy | Additive |
| Etoposide | Topoisomerase inhibitor | Additive | Additive | Synergy | Additive |
| Carboplatin | DNA binding/crosslinking agent | Additive | Additive | Slight Synergy | Additive |
| Entinostat | HDAC inhibitor | Synergy | Synergy | Synergy | Additive |
| Panobinostat | HDAC inhibitor | Synergy | Additive | Synergy | Additive |
| Romidepsin | HDAC inhibitor | Additive | Synergy | Synergy | Additive |
| palbociclib | CDK4/6 inhibitor | Synergy | Synergy | Synergy | Additive |
| abemaciclib | CDK4/6 inhibitor | Synergy | Synergy | Additive | Additive |
| selumetinib | MEK inhibitor | Synergy | Synergy | ND | ND |
| trametinib | MEK inhibitor | Synergy | Synergy | Synergy | Additive |

Example 4

Combination Studies of Tazemetostat with X-Ray Irradiation

Figure 11A:
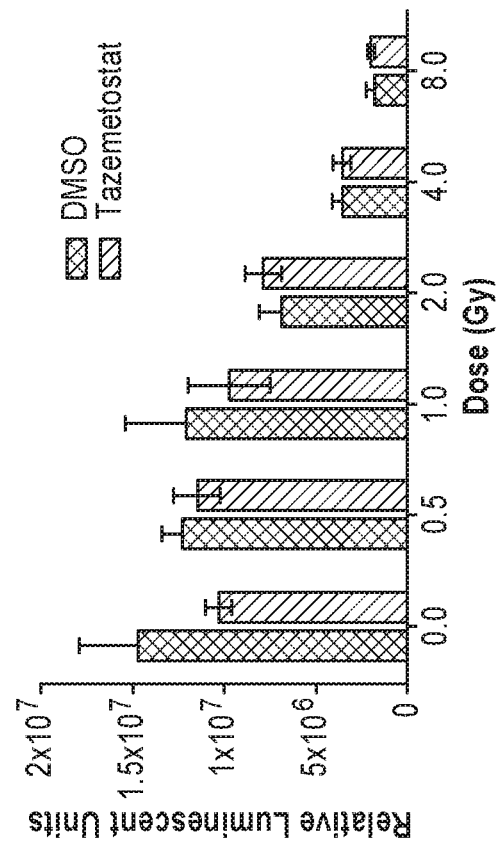
FIGS. 11A and 11B show the effect of tazemetostat treatment following X-ray irradiation on cell proliferation in a BT-12 cell line. Proliferation was quantified through cellular adenosine triphosphate (ATP) in a luminescent cell viability assay. The Figure compares the cell viability in terms of relative luminescence units in plates incubated with tazemetostat to that in plates incubated with DMSO following X-ray irradiation at levels from 0 to 8 Gy (FIG. 11A) immediately after irradiation and (FIG. 11B) after 7 days of incubation.
Figure 11B:
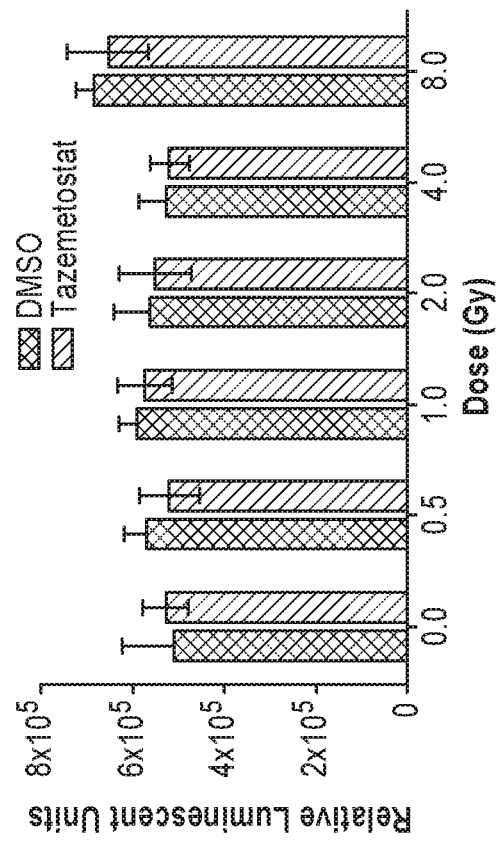

X-ray radiation followed by tazemetostat treatment: BT-12 Cells were treated with increasing levels of radiation from 0 to 8 Gy. Cells were immediately harvested and seeded to 96 well plates containing 10 μM Tazemetostat. Plated were incubated for seven days and quantification of proliferation through measurement of cellular adenosine triphosphate (ATP) was performed in a luminescent cell viability assay. The results of this experiment are summarized in FIG. 11.

Tazemetostat pre-treatment followed by X-ray irradiation: BT-12 Cells were pretreated with tazemetostat for 7 days, followed by X-ray irradiation at 2 Gy or Mock treatment, and seeded for a 7 day proliferation assay (FIG. 12, panel A) or 11 day clonogenic assay (FIG. 12, panel B) in absence of tazemetostat. Antagonism was not found with tazemetostat priming for 7 days in vitro.

Antagonism was not found when X-ray irradiation followed tazemetostat priming for 7 days in vitro. X-ray irradiation induced a time and dose dependent reduction in cell proliferation. A combination benefit was found when cells were irradiated immediately prior to treatment with tazemetostat. Furthermore a reduction in clonogenic survival of atypical teratoid rhabdoid tumor (AT/RT) cells was observed when cells were primed with tazemetostat for seven days prior to X-ray irradiation.

The disclosure can be embodied in other specific forms without departing from the spirit or essential characteristics thereof. The foregoing embodiments are therefore to be considered in all respects illustrative rather than limiting on the disclosure described herein. Scope of the disclosure is thus indicated by the appended claims rather than by the foregoing description, and all changes that come within the meaning and range of equivalency of the claims are intended to be embraced therein.

What is claimed is:

1. A method for treating a malignant rhabdoid tumor (MRT) or an atypical teratoid/rhabdoid tumor (AT/RT) comprising administering to a subject:

(a)

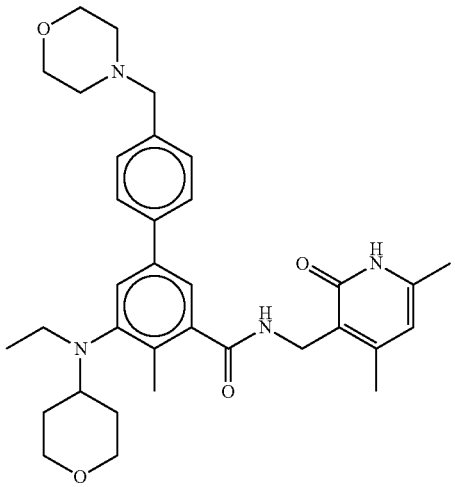

(tazemetostat), or a pharmaceutically acceptable salt thereof, and (b) panobinostat.

2. The method of claim 1, wherein panobinostat is administered prior to the tazemetostat or the pharmaceutically acceptable salt thereof.

3. The method of claim 1, wherein tazemetostat, or the pharmaceutically acceptable salt thereof, is administered prior to panobinostat.

4. A method for treating a malignant rhabdoid tumor (MRT) or an atypical teratoid/rhabdoid tumor (AT/RT), comprising sensitizing a subject, wherein the sensitizing comprises administering to the subject:

(a)

(a)

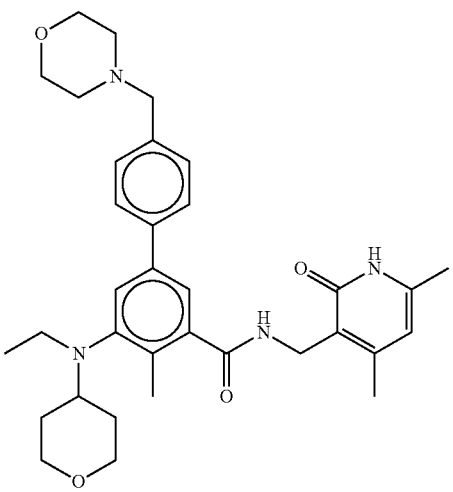

(tazemetostat), or a pharmaceutically acceptable salt thereof, and (b) panobinostat.

5. The method of claim 1, wherein the method is for treating a malignant rhabdoid tumor (MRT).

6. The method of claim 1, wherein the method is for treating an atypical teratoid/rhabdoid tumor (AT/RT).

7. The method of claim 4, wherein the method is for treating a malignant rhabdoid tumor (MRT).

8. The method of claim 4, wherein the method is for treating an atypical teratoid/rhabdoid tumor (AT/RT).

* * * * *